United States Patent [19]

Yosizato et al.

[11] Patent Number: 5,414,118
[45] Date of Patent: May 9, 1995

[54] DIAMINOUREA COMPOUND AND PROCESS FOR PRODUCTION THEREOF AND HIGH HEAT RESISTANT POLYURETHANEUREA AND PROCESS FOR PRODUCTION THEREOF

[75] Inventors: Akihiko Yosizato; Satoshi Furubeppu, both of Moriyama, Japan

[73] Assignee: Asahi Kasei Kogyo Kabushiki Kaisha, Osaka, Japan

[21] Appl. No.: 176,503

[22] Filed: Dec. 30, 1993

Related U.S. Application Data

[63] Continuation of Ser. No. 956,014, Dec. 9, 1992, abandoned.

[30] Foreign Application Priority Data

Apr. 12, 1991 [JP] Japan ................. 3-106496
Jul. 22, 1991 [JP] Japan ................. 3-204540
Oct. 8, 1991 [JP] Japan ................. 3-260784

[51] Int. Cl.$^6$ ................. C07C 275/06; C07C 275/28; C07C 273/00
[52] U.S. Cl. ................. 564/51; 564/48; 564/50; 564/61; 564/64
[58] Field of Search ................. 564/50, 51, 57, 61, 564/64, 48, 56

[56] References Cited

U.S. PATENT DOCUMENTS

| | | | |
|---|---|---|---|
| 4,404,390 | 9/1983 | Atland et al. | 548/263 |
| 4,950,789 | 8/1990 | Barron | 564/22 |
| 4,994,611 | 2/1991 | Ruckes et al. | 564/50 |

FOREIGN PATENT DOCUMENTS

| | | | |
|---|---|---|---|
| 1793125 | 1/1972 | Germany . | |
| 46-4795 | 11/1971 | Japan . | |
| 50107211 | 2/1974 | Japan . | |
| 59-64621 | 4/1984 | Japan . | |
| 3-48652 | 3/1991 | Japan . | |
| 3-135950 | 6/1991 | Japan . | |
| 739068 | 6/1980 | U.S.S.R. | 564/50 |
| 8400376 | 2/1984 | WIPO . | |

OTHER PUBLICATIONS

Kryuchov et al., the Synthesis of Polyurethane Ureas with a Specific MWD of thir Rigid Segments, Polymer Science USSR, vol. 23, No. 11, 1981 pp. 2715-2721.
Kryuchkov et al., Preparing Poly(urethaneureas) in a Solution, Chemical Abstracts, vol. 94, No. 8, 23 Feb. 1981, Columbus, OH., Abstract No. 48271g, p. 37, column 2.
Melissaris et al., J. of Appl. Polym. Sci., vol. 39, 2657-2672, 1987.

*Primary Examiner*—Shailendra Kumar
*Attorney, Agent, or Firm*—Finnegan, Henderson, Farabow, Garrett & Dunner

[57] ABSTRACT

A diaminourea compound having the formula (I);

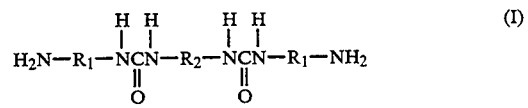

wherein $R_1$ and $R_2$ are independently a straight or branched alkylene group having 2 to 8 carbon atoms, an alicyclic alkylene group having 6 to 15 carbon atoms, a phenylene group, a $C_1$-$C_4$ alkyl-substituted phenylene group, a $C_1$-$C_4$ mono- or di-alkylene substituted phenylene group, or a methanediphenylene group, and a production process thereof as well as a high heat resistant polyurethaneurea derived therefrom and a production process thereof.

2 Claims, 37 Drawing Sheets

DIAMINOUREA COMPOUND AND PROCESS FOR PRODUCTION THEREOF AND HIGH HEAT RESISTANT POLYURETHANEUREA AND PROCESS FOR PRODUCTION THEREOF

This application is a continuation of application Ser. No. 07/956,014, filed Dec. 9, 1992, now abandoned.

TECHNICAL FIELD

The present invention relates to a novel diaminourea compound useful as a chain extender of a shaped article (for example, elastic fiber and film) of a high heat resistant polyurethaneurea and a high molecular weight-providing additive or a curing agent of an epoxy resin, and a process for the production of the same and further relates to a polyurethaneurea superior in heat resistance in which the novel diaminourea compound is used as a chain extender and a process for the production of the same and to a process for production of a polyurethaneurea superior in heat resistance in which the diaminourea compound is used as a high molecular weight-providing additive.

BACKGROUND ART

Organic diamines are generally used for chain extenders of polyurethaneurea, intermediate materials for resins, curing agents for the manufacture of epoxy resins, etc., but there has been no example of a diamine having active hydrogen at the two ends thereof and having a structure including two or more urea groups. The diaminourea compound of the present invention is a novel substance not yet disclosed in any reference and is structured with two urea groups in a molecule, as expressed by chemical formula (I), and amino groups at its two ends. When trying to synthesize this compound, the method in which one end of the diamine compound is reacted with the two ends of the diisocyanate compound to form a diaminourea compound, while urea groups are formed, may be considered. However, in a method where a diisocyanate compound is added dropwise little by little into an excess of diamine compound, the active amino groups of the reaction product react with the unreacted isocyanate groups to become higher molecular weight and it becomes difficult to remove the same as a monomer. Therefore, up to now, the physical properties and the usefulness have not been known.

In general, polyurethaneurea is obtained by causing a reaction of an excess molar amount of diisocyanate with an organic diol to synthesize an intermediate polymer with isocyanate groups at the two ends and then adding thereto an organic diamine as a chain extender to increase the molecular weight. Since an excess molar amount of the diisocyanate compound is reacted with the organic diol, the intermediate polymer (that having isocyanate groups at two ends thereof, which is called "prepolymer" hereinbelow) is comprised of an organic diol connected by the diisocyanate compound and unreacted diisocyanate compound. By adding an organic diamine there and causing a reaction between the amino groups and isocyanate groups, hard segments with urea groups are formed. The hard segments in the polymer form a hard domain by intermolecular hydrogen bonding of the urea groups. This becomes a cross-linking point for the polymer as a whole and has a major effect on the heat resistance of the polyurethaneurea.

At this time, the size of the hard segments has a distribution due to the presence of the unreacted diisocyanate compound. The minimum unit of the hard segments is formed when the prepolymer is directly connected with the added diamine compound, without being taken out by the unreacted diisocyanate compound. The structure thereof is that two molecules of the diisocyanate compound are connected with one molecule of a diamine compound (where the two molecules of the diisocyanate compound are the diisocyanate compound at the ends of the prepolymer). At this time, there are two urea groups in the structure of the minimum construction unit of the hard segment (i.e., "U2 hard" hereinbelow). The next large constitution unit next to U2 hard is that obtained by connecting the prepolymer with two molecules of the diamine compounds having one molecule of an intermediate unreacted diisocyanate compound connected therebetween, which has a structure of three molecules of the diisocyanated compound connected with two molecules of the diamine compound. At this time, there are four urea groups in the hard segment (i.e., "U4 hard" hereinbelow). Similarly, there are hard segments with successively higher molecular weights (i.e., "U6 hard", "U7 hard" . . . hereinbelow). In the coventional production method of polyurethaneurea, the minimum constitution unit of U2 hard occupies the major part of the total hard segments.

In order to improve the heat resistance of the polyurethaneurea, it is considered to introduce a greater number of urea groups in the hard segments and raise the hydrogen bonding force between molecules by making the average molecular weight of the hard segments higher. That is, the ratio of the U2 hard having a weaker intermolecule hydrogen bond force is made smaller and the ratios of the U4 hard, U6 hard . . . having a relatively high hydrogen bond force is made larger. More specifically, a diisocyanate compound is further added to the intermediate polymer and the chain is extended by a diamine compound in an equivalent amount to the isocyanate group. In this case, however, relatively high molecular weight hard segments such as U6 hard, U8 hard . . . are also formed. When the hard segments are made high molecular weight in such a way, since the solubility of U6 hard, U8 hard in a solvent is low, the viscosity stability of the polymer stock solution over time becomes poorer, when the hard segments form hard domains, and, in the worst case, gelation occurs. That is, there were limits to the control of the molecular weight of the hard segments with such a method.

In this way, with regards to the control of the molecular weight of the hard segments, which has a major effect on the heat resistant properties of the polyurethaneurea polymer, up until now the distribution of the molecular weight has not been controlled. Only the average molecular weight has been controlled and only within a limited range.

As a chain extender of a polyurethaneurea polymer, use has been made of compound including a urea group similar to the diaminourea compound according to the present invention. As an example, there has been disclosed a process for production of a heat resistant polyurethaneurea elastomer using the following formula (VI):

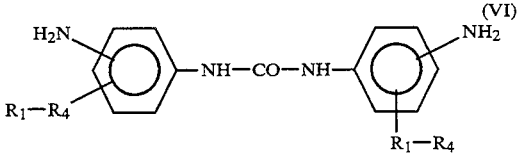

wherein $R_1$, $R_2$, $R_3$, and $R_4$ each independently represent hydrogen or a $C_1$ to $C_6$ alkyl group, and the amino group in the formula is at the meta position and/or para position with respect to the urea (Japanese Unexamined Patent Publication (Kokai) No. 1-110520). The diaminodiphenylurea compound having the above formula (VI), however, has a low solubility in a solvent at room temperature, so when using this compound as a chain extender during the production of a polymer, a homogeneous polymerization reaction cannot be expected. Further, in the case of the above-mentioned diaminodiphenylurea compound, there is one urea group in the structure of the molecule and therefore the heat resistance cannot be said to be fully sufficient.

As a compound resembling the compound of the present invention, there is the compound having the formula (VII):

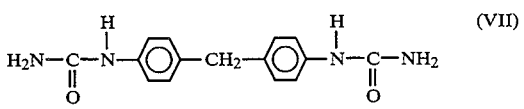

This compound is shown as an intermediate, in Japanese Unexamined Patent Publication (Kokai) No. 3-27351, in the production of methylenediphenylenediisocyanate and polymethylenepolyphenylenepoly(isocyanate), but since the two ends are not amino groups, but are urea groups, the reactivity is low and so this is not suitable to use as a chain extender, additive for imparting high molecular weight, curing agents, etc.

As another method for improving the heat resistance, attempts have been made in the past to make the polyurethaneurea higher in molecular weight. When just using a high viscosity stock solution increased in molecular weight during the production of a polymer (polymerization), the pressure in the pipes increases during the feeding of the solution to the molding process, the spinning stringiness becomes lower, the yarn often breaks in the spinning chimney, and other problems occur. As a method of solving these problems, the method of spinning a polymer stock solution obtained by a polymerization reaction of an intermediate polymer with an isocyanate end and an excess amount of a bifunctional and monofunctional compound having active hydrogen and the method of after-treatment of the yarn by heat to increase the molecular weight have been proposed (Japanese Examined Patent Publication (Kokoku) No. 40-3717, Japanese Examined Patent Publication (Kokoku) No.47-13789, Japanese Unexamined Patent Publication (Kokai) No. 60-14623, and Japanese Unexamined Patent Publication (Kokai) No. 60-173117). Even in these arts, however, as described on page 3 in Japanese Unexamined Patent Publication (Kokai) No. 1-170648, the viscosity of the polymer stock solution increase over time in the storage tank or feed pipes and lacks stability, so stable production was difficult. Therefore, an attempt was described of adding and mixing a low molecular weight compound (as a specific typical example, the reaction product between one mole of 4,4'-diphenylmethanediisocyanate and two moles of dialkylamine, that is, the compound having the formula (VIII): N,N-(methylenedi-4,1-phenylene)bis(-diethyl)-urea) to polyurethaneurea and performing heat treatment to convert to a high molecular weight (Japanese Unexamined Patent Publication (Kokai) No. 59-129257 and Japanese Unexamined Patent Publication (Kokai) No. 1-170648)

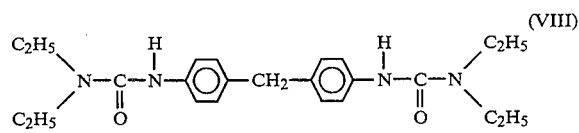

However, a polyurethaneurea shaped article made by the known art using a compound having the formula (VIII) was unsatisfactory in the following points:

(1) The effect of improvement of the elastic functions and heat resistance is still insufficient.
(2) The knot strength is low.
(3) During spinning, the yarn often breaks inside the spinning chimney (stringiness of spinning stock solution is low).

Furthermore, the aromatic diurea compound having the chemical formula (VIII) of the known art, unlike with the following formula (I) of the present invention, does not have active hydrogen groups at the two end groups and is low in chemical activity. Therefore, these are not suitable as a chain extender of polyurethaneurea, additives for high polymerization, curing agents for epoxy resins, etc.

DISCLOSURE OF INVENTION

Accordingly, the objects of the present invention is to provide a novel diaminourea compound including active hydrogen at its two ends and two urea groups useful as a chain extender for high heat resistance polyurethaneurea and an additive for imparting a high molecular weight.

Other objects of the present invention are to produce the above-mentioned diaminourea compound in a high purity and high yield and to produce a high heat resistance polyurethaneurea using the same.

In accordance with the present invention, there is provided a diaminourea compound expressed by the formula (I):

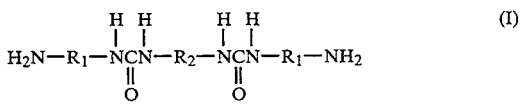

wherein $R_1$ and $R_2$ are independently a straight chain or branched alkylene group having 2 to 8 carbon atoms, an alicyclic alkylene group having 6 to 15 carbon atoms, a phenylene group, a $C_1$–$C_4$ alkyl-substituted phenylene group, a $C_1$–$C_4$ mono- or di-alkylene substituted phenylene group, or a methanediphenylene group.

In accordance with the present invention, there is also provided a process for the production of a diaminourea compound expressed by chemical formula (I) characterized in that a diurea compound expressed by the formula (II):

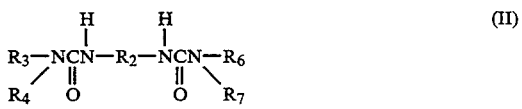

(II)

wherein, $R_3$, $R_4$, $R_6$, and $R_7$ independently represent a straight or branched alkyl groups having 1 to 4 carbon atoms, $R_2$ represents a straight or branched alkylene group having 2 to 8 carbon atoms, an alicyclic alkylene group having 6 to 15 carbon atoms, a phenylene group, a $C_1$-$C_4$ alkyl-substituted phenylene group, a $C_1$-$C_4$ mono- or di-alkylene substituted phenylene group, or a methanediphenylene group and a diamine compound having the formula (III)

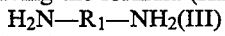

wherein $R_1$ represents a straight or branched alkylene group having 2 to 8 carbon atoms, an alicyclic alkylene group having 6 to 15 carbon atoms, a phenylene group, a $C_1$-$C_4$ alkyl-substituted phenylene group, a $C_1$-$C_4$ mono- or di-alkylene substituted phenylene group, or a methanediphenylene group are allowed to react.

In accordance with the present invention, there is further provided a process for production of a diaminourea compound having formula (I) characterized in that a diurethane compound expressed by the following chemical formula (IV):

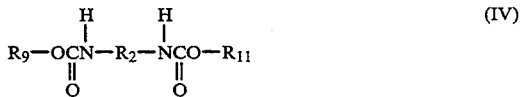

(IV)

wherein $R_9$ and $R_{11}$ independently represent a straight or branched alkyl group having 1 to 4 carbon atoms, cyclohexyl group, phenylene group, or straight or branched $C_1$-$C_4$ alkyl-substituted phenyl group, $R_2$ represents a straight or branched alkylene group having 2 to 8 carbon atoms, an alicyclic alkylene group having 6 to 15 carbon atoms, a phenylene group, a $C_1$-$C_4$ alkyl-substituted phenylene group, a $C_1$-$C_4$ mono- or di-alkylene substituted phenylene group, or a methanediphenylene group and a diamine compound having the formula (V)

(V)

wherein $R_1$ represents a straight or branched alkylene group having 2 to 8 carbon atoms, an alicyclic alkylene group having 6 to 15 carbon atoms, a phenylene group, a $C_1$-$C_4$ alkyl-substituted phenylene group, a $C_1$-$C_4$ mono- or di-alkylene substituted phenylene group, or a methanediphenylene group are allowed to react. In one embodiment of the invention, in the above formulas (I)-(V), $R_1$ is a straight chain or branched alkylene group having 2 to 8 carbon atoms and $R_2$ is a methanediphenylene group.

In accordance with the present invention, there is further provided a process for production of a polyurethaneurea comprised by allowing an excess molar amount of organic diisocyanate to react with a polymer diol having a number average molecular weight of 500 to 100,000 to synthesize an intermediate polymer having an isocyanate group at its ends, then allowing the intermediate polymer to react with a bifunctional diamine compound, wherein the diaminourea compound expressed by the formula (I) is used as a part or all of the said bifunctional diamine compound.

In accordance with the present invention, there is further provided a process for production of a polyurethaneurea by heat treatment of a compound obtaining by adding, in an amount satisfying the following equation, a diaminourea compound expressed by the formula (I) to a polyurethaneurea obtained by allowing a reaction of an excess molar amount of an organic diisocyanate with a polymer diol having a number average molecular weight of 500 to 100,000 to synthesize an intermediate polymer having an isocyanate group at its ends, then allowing the intermediate polymer to react with a bifunctional diamine compound and monofunctional amine compound.

$$0.005 \leq A/B \leq 3$$

wherein A is the molar amount added of the diaminourea compound expressed by the formula (I) and B is the molar amount of the monofunctional amine used for the production of the polyurethaneurea polymer.

In accordance with the present invention, there is further provided a polyurethaneurea wherein, when producing a polyurethaneurea by allowing a reaction of an excess molar amount of an organic diisocyanate with a polymer diol having a number average molecular weight of 500 to 100,000 to synthesize an intermediate polymer having an isocyanate group at its ends, then allowing a reaction of a bifunctional diamine compound with the intermediate polymer, the ratio of area of the peak corresponding to the hard segment having four urea groups, analyzed by the method set forth in the specification, out of the hard segments formed by the bifunctional diamine compound is at least 40 percent of the total.

BRIEF DESCRIPTION OF THE DRAWINGS

The present invention will be explained in detail with reference to the accompanying drawings wherein.

BEST MODE FOR CARRYING OUT THE INVENTION

Figure 1:
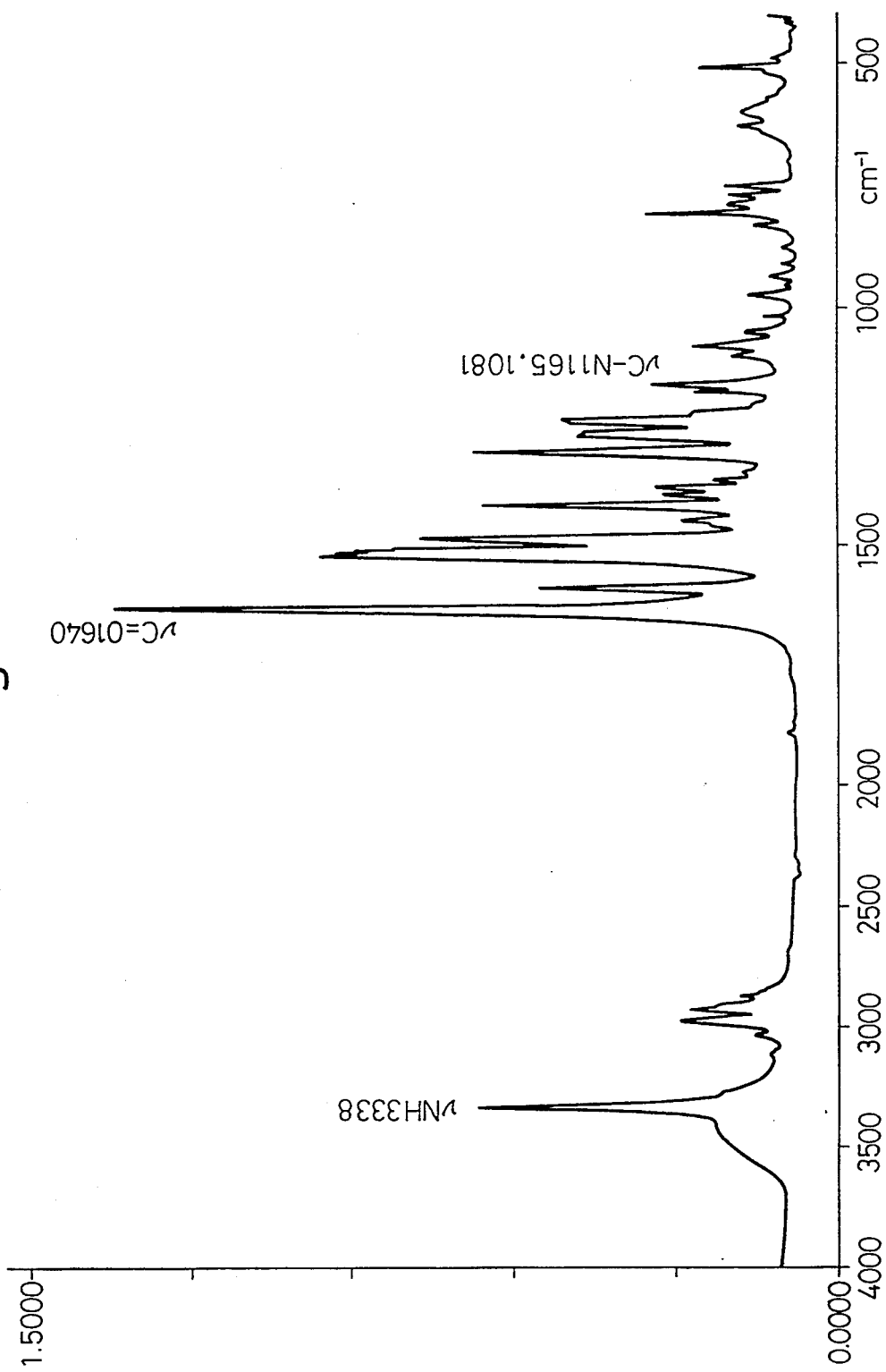
FIG. 1 is the infrared absorption spectrum of the compound (A)

The present inventors engaged in in-depth research on a novel chain extender for obtaining a high heat resistance polyurethaneurea and as a result discovered a novel diaminourea compound having highly reactive active hydrogen at the two end groups, thus completing at the present invention.

The typical examples of the diaminourea compounds according to the present invention are as follows:

Compound (1): N,N'-(methylenedi-4,1-phenylene)bis(2-(ethylamino)-urea)

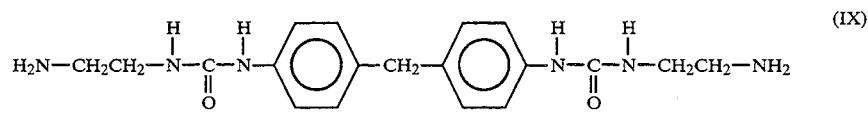
(IX)

Compound (2): N,N'-(methylenedi-4,1-phenylene)bis(2-(2-methylethylamino)-urea)

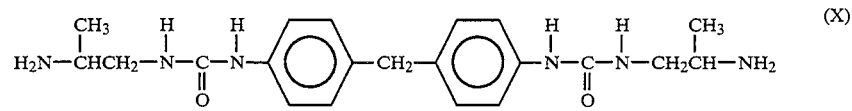
(X)

Compound (3): N,N'-(methylenedi-4,1-phenylene)bis(6-(hexylamino)-urea)

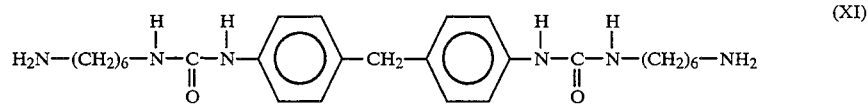
(XI)

The diaminourea compound having the formula (I) according to the present invention can be produced by the reaction between the diurea compound having the above-mentioned formula (II) or the diurethane compound having the above-mentioned formula (IV) and the diamine compound having the above-mentioned formula (III).

The diurea compound having the above-mentioned formula (II) or the diurethane compound having the above-mentioned formula (IV) may be easily produced by causing a reaction of two or more molar amounts of the respectively corresponding lower amines or lower alcohols or phenols with diisocyanates in the presence or absence of an inert solvent such as tetrahydrofuran or toluene.

As examples of the diisocyanates, mention may be made of 4,4'-diphenylmethane diisocyanate, tolylene diisocyanate, 1,5-naphthalene diisocyanate, tridine diisocyanate, hexamethylene diisocyanate, isophorone diisocyanate, p-phenylene diisocyanate, transcyclohexane 1,4-diisocyanate, xylylene diisocyanate, hydrogenated xylylene diisocyanate, hydrogenated methylenediphenyl diisocyanate, tetramethylxylylene diisocyanate, etc.

As examples of the lower amines, mention may be made of dimethylamine, diethylamine, methylethylamine, methylisopropylamine, ethylpropylamine, diisopropylamine, dibutylamine, and other low boiling point secondary amine compounds, etc., preferably dimethylamine, diethylamine, methylethylamine, and diisopropylamine.

As examples of the lower alcohols, mention may be made of methyl alcohol, ethyl alcohol, propyl alcohol, isopropyl alcohol, cyclohexanol, and other low boiling point alcohols or, as phenols, phenol, methylphenol, ethylphenol, butylphenol, and other straight chain or branched $C_1-C_4$ alkyl-substituted phenols, preferably methyl alcohol, ethyl alcohol, and phenol.

As examples of the diamine compounds of the compounds of the above-mentioned formula (III), mention may be made of ethylenediamine, 1,2-propylenediamine, 1,3-diaminopropane, 1,4-diaminobutane, 1,6-hexamethylenediamine, 2-methyl-1,5-pentanediamine, 1,8-octamethylenediamine, 1,2-bis-(3-aminopropoxy)ethane, 1,3-bis-(3-aminopropoxy)-2,2-dimethylpropane, xylenediamine, metaphenylenediamine, diaminodiphenylmethane, cyclohexyldiamine, isophoronediamine, diaminodicyclohexylmethane, bis(aminomethyl)cyclohexane, etc.

The process of production of the present invention may be produced by allowing a reaction of two or more molar amounts of the diamine having the above-mentioned formula (III) with the compound having the above-mentioned formula (II) or the above-mentioned chemical formula (IV) for an amine exchange reaction with the diamine.

The reaction of the compound of the above-mentioned formula (II) or the compound of the above-mentioned formula (IV) with the compound of the above-mentioned formula (III) generally is performed using as a solvent the diamine having the above-mentioned formula (III) and progresses well with heating. It is also possible to perform the reaction in the presence of a solvent inert to amino groups or isocyanate groups. In this case, as the solvent, use may be made of toluene, xylene, and other aromatic hydrocarbons, dimethylacetoamide, dimethylformamide, etc. The pressure at the time of the reaction may be under pressure, under a reduced pressure or under an atmospheric pressure. The reaction is preferably performed in an inert gas atmosphere, for example, a dry nitrogen atmosphere.

In general, the boiling point of the lower amine and lower alcohol eliminated from the diurea compound of the above-mentioned formula (II) or the diurethane compound of formula (IV) is preferably lower than the boiling point of the diamine of the above-mentioned formula (III) used for the amine exchange. In this case, if the reaction temperature is set higher than the boiling point of the eliminated lower amine or lower alcohol and near the boiling point of the diamine of the above-mentioned formula (III) for the amine exchange, the reaction will proceed well. While the reaction temperature is not necessarily set due to the type of the material, the type of the solvent, and other conditions, usually it is possible to select it from about 50° C. to 200° C. The starting point and ending point of the reaction can be confirmed by the distilled state (distillation temperature and theoretical distillation amount) of the lower amine or lower alcohol eliminated by the amine exchange reaction from the compound of the above-mentioned formula (II) or formula (IV).

To isolate the desired compound from the end reaction solution thus obtained, when the reaction product is dissolved in the solvent after the completion of reaction first any precipitate is filtered, the solvent in the filtrate is removed once by reduced pressure distillation, the residue is sufficiently washed by an organic solvent such as tetrahydrofuran (THF), and dried and the solvent is removed. The product can be optionally purified by, for example, recrystallization.

The novel diaminourea compound of the present invention obtained in this way has two urea groups in a molecule, so by using the diaminourea compound as a polymer chain extender, it is possible to form a strong intermolecular hydrogen bond between the polymer molecules in the polyurethaneurea and therefore greatly improve the heat resistance.

That is, the present inventors discovered the novel diaminourea compound as a result of in-depth research and discovered that by using this as a polymer chain extender, it is possible to increase crystallinity of the hard segments of the polyurethaneurea and form strong intermolecular physical cross-linking points. By this, the desired polyurethaneurea having small thermal fluid deformation of the polymer molecules and a heat setting rate and a superior heat resistance is produced.

That is, the present invention provides a process for production of a polyurethaneurea superior in heat resistance comprised by causing an excess molar amount of organic diisocyanate to react with a polymer diol of a number average molecular weight of 500 to 100,000 to synthesize an intermediate polymer having an isocyanate group at its end, then causing a reaction of a bifunctional diamine compound, said process for production of a polyurethaneurea characterized by the partial or entire use of the diaminourea compound having the formula (I) for the said bifunctional diamine compound.

The said diaminourea compound may be used as is as a high purity monomer or may be used mixed in with the polynuclear product expressed by the formula (XII) produced as a byproduct in the process of production without a detrimental effect on the properties of the polyurethaneurea:

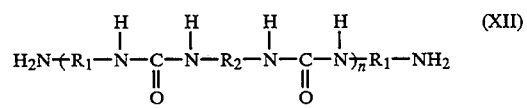

wherein $R_1$ and $R_2$ are independently a straight chain or branched alkylene group having 2 to 8 carbon atoms, an alicyclic alkylene group having 6 to 15 carbon atoms, a phenylene group, a $C_1-C_4$ alkyl-substituted phenylene group, a $C_1-C_4$ mono- di-alkylene substituted phenylene group, or a methanediphenylene group, and n is an integer of 2 or more.

The diamineurea compound has good solubility in the organic solvent, for example, dimethylacetoamide usable at the time of polymerization of the polyurethaneurea. For example, taking the example of compound (I), it dissolves at room temperature to an extent of about 20% by weight and enables a uniform polymerization reaction.

If, instead of the diaminourea compound expressed by the above-mentioned formula (I), use is made of an equal molar amount of a diisocyanate compound and organic diamine constituting the compound, the heat resistant polyurethaneurea of the present invention cannot be obtained.

As examples of a polymer diol having a number average molecular weight of 500 to 100,000 in the present invention, mention may be made of homopolymers or copolymers obtained by polymerization of ring-opening polymerizable monomers such as ethyleneoxide, propyleneoxide, tetrahydrofuran, methyltetrahydrofuran, oxetane, methyloxetane, dimethyloxetane, etc.; or polyetherdiols such as copolymers obtained by polymerization of ring-opening polymerizable monomers and compounds having 2 or more hydroxyl groups in a molecule such as straight chain or branched alkylene glycols with 2 to 10 carbon atoms, specifically, copolymers obtained by polymerization of, for example, tetrahydrofuran and neopentylglycol; polyesterdiols obtained from one or more types of dibasic acids selected from adipic acid, sebacic acid, maleic acid, itaconic acid, etc. and one or more glycol among straight chain or branched glycols having 2 to 10 carbon atoms such as ethyleneglycol, propylene glycol, 1,4-butane diol, hexamethylene glycol neopentylglycol, and glycols such as diethyleneglycol, 3-methyl-1,5-pentane diol, 2-methyl-1,8-octane diol, 1,9-nonane diol; poly-$\epsilon$-caprolactone diol, and polycarbonate diols, having 2 to 10 carbon atoms, using as a starting material straight chain or branched alkyleneglycols; polyetherester diols, polyethercarbonate diols; polyestercarbonate diols; and other homo or copolymers. Preferable examples are polyether diols, polyester diols, polycarbonate diols, polyester diols, polycarbonate diols with a number average molecular weight of 1000 to 20,000.

In the present invention, an excess molar amount of organic diisocyanate groups are made to react with the above-mentioned polymer diol to synthesize the intermediate polymer having isocyanate groups at its two end groups, i.e., the urethane prepolymer.

The excess molar amount as spoken of in the present invention refers to a ratio of the molar amount of the polymer diol used in the present invention and the molar amount of the organic diisocyanate of 1:1.1 to 1:3.0, preferably 1:1.3 to 1:2.5.

Normally, the reaction of the organic diisocyanate with the polymer diol is caused in the presence or absence of a solvent and at a reaction temperature of a suitable 0° C. to 100° C. so as to obtain a urethane prepolymer with isocyanate groups at its two ends. In this case, it is also possible to use a catalyst which promotes the urethane reaction, such as a stannous organic compound, or a negative catalyst comprised or an acid inorganic or organic compound which suppresses secondary reactions.

In this case, as the organic diisocyanate used, numerous compounds, including the following compounds, are known (Nikkan Kogyo Shimbumsha, "Polyurethane Resin Handbook, page 517): for example, m- and p-phenylene diisocyanate, 2,4 and 2,6-tolylene diisocyanate, m- and p-xylylene diisocyanate, 4,4'-diphenylmethane diisocyanate, 4,4'-diphenyl-dimethylmethane diisocyanate, 4,4'-diphenylether diisocyanate, naphtalene-1,5-diisocyanate, 1,6-hexamethylene diisocyanate, 4,4'-cyclohexylene diisocyanate, 1,3-bis($\alpha,\alpha$-dimethylisocyanate-methyl)benzene, 1,4-bis-($\alpha$, $\alpha$-dimethylisocyanate-methyl)benzene, tetrachloro-m- and p-xylylene-diisocyanate, isophorone diisocyanate, etc. Preferably, use is made of diisocyanate compounds having benzene rings, in particular 4,4'-diphenylmethane diisocyanate.

After the intermediate polymer, that is, the urethane prepolymer, is synthesized, a chain extension reaction is performed by the urethane prepolymer having isocyanate groups at its two end groups and the bifunctional diamine compound to obtain the polyurethaneurea. At this time, sometimes a monofunctional amine compound is added and the molecular weight of the polymer is adjusted by an end terminating reaction so as to obtain the polyurethaneurea polymer. In this case, the equivalent amount of the amino reaction groups of the bifunctional diamine compound or the equivalent amount of the total amino reaction groups of the bifunctional diamine compound and monofunctional amine compound is substantially the same as the equivalent amount of the isocyanate groups in the urethane prepolymer or equivalent amount of the amino reaction groups is in excess.

Further, it is also possible to use an excess of the bifunctional diamine compound to the isocyanate groups so as to cause a reaction using the bifunctional diamine compound as a monofunctional amine compound. That is, in this case, the amino groups of the excess equivalent amount of the bifunctional amine compound remain unreacted in the polymer end groups as single-end amino groups and function as polymer molecular weight adjusters.

The reaction of the urethane prepolymer and amine compound is extremely fast. Therefore, to perform the reaction slowly, it is possible to use a low reaction temperature, so long as the temperature is above the melting point of the reaction solvent used and one where the prepolymer will not precipitate from the solvent.

The diaminourea compound having the formula (I) used in the process of production of the present invention may be used alone or used as a mixture of the diaminourea compounds having the formula (I) and also may be used mixed or together with another known bifunctional diamine compound. At this time, even when the molar ratio of the mixture of the diaminourea compound used in the present invention is small, the effect of a high heat resistance is exhibited. The ratio is preferably at least 10% and more preferably at least 20%, whereupon a greater effect is exhibited. As an example of the known bifunctional daimine compound in this case, there are known numerous compounds including the following (Nikkan Kogyo Shimbunsha, "Polyurethane Resin Handbook", page 517): for example, ethylenediamine, 1,2-propylenediamine, hexamethylenediamine, 1,4-cyclohexyldiamine, 1,4-tetrachloroxylenediamine, 1,3-cyclohexyldiamine, 1,3-tetrachloroxylenediamine, 1,4-xylylenediamine, 1,4-diaminopiperazine, etc. Particularly preferable are ethylenediamine, 1,2-propylenediamine, 1,3-cyclohexyldiamine, and 1,4-cyclohexyldiamine.

During the polymerization of the polyurethaneurea, when use is made of a monofunctional amine compound as a polymer molecular weight adjuster, mention may be made as examples of the monofunctional amine compound of diethylamine, dimethylamine, methylethylamine, methylisopropylamine, methyl-n-propylamine, diisopropylamine, methyl-n-butylamine, methylisobutylamine, methylisoamylamine etc. When use is made of a monofunctional amine compound, the reaction may be performed by adding the urethane prepolymer before the bifunctional diamine compound or the reaction may be performed by adding them simultaneously. The amount of the monofunctional amine compound used can be appropriately selected depending upon the molecular weight of the intended polyurethaneurea, it is suitably no more than 40 percent equivalent amount of the total amine equivalent amount supplied to the urethane prepolymer.

During the intermediate polymerization or during the reaction of the intermediate polymer with the amine compound, sometimes a solvent may be used. As examples of the solvent, mention may be made of dimethylformamide, dimethylacetoamide, dimethylpropionamide, dimethylsulfoxide, and N-methylpyrrolidone.

When a solvent is used, the concentration of the polymer solids is usually 15% by weight or more, preferably 20 to 40% by weight. The polymer entering the molding process may have further added to it a known antioxidant, coloring preventing agent, ultraviolet absorbant, or other stabilizing agent, pigments such as titanium oxide, antistatic agents, antifungal agents, and other additives and fillers (stearic acid metal salts, magnesium oxide, hydrotalcite, zinc oxide). This is then heat formed by a dry or wet type spinning machine or molding machine to make fibers, film, etc. In the case of fibers, the spun yarn is false-twisted and provided with an oil agent or lubricant stearic acid metal salt etc. The type of the oil agent is not particularly limited, but dimethylpolysiloxane, diorganopolysiloxane obtained by substituting another alkyl group or phenyl group for part of the methyl groups of dimethylpolysiloxane, organopolysiloxane of modified polysiloxane obtained by introducing amino groups, vinyl groups, epoxy groups, etc., and mineral oils are preferable.

The polyurethaneurea obtained in this way using the diaminourea compound of the present invention as a chain extender has characteristic features in the distribution of the hard segments. In the general process for production of polyurethaneurea, there is a large distribution seen in the molecular weight of the hard segments, with the smallest unit of hard segments being one with two urea groups (U2 hard), the next unit being one with four urea groups (U4 hard), and the next larger units having similarly more groups (U6 hard, U8 hard ...). This distribution differs depending on the design of the molecular weight of the hard segments, but in general the U2 hard account for the major part of the total number of moles of the hard segments, followed by the U4 hard, U6 hard, etc. in declining ratio. As opposed to this, if the diaminourea compound of the present invention is used for the chain extender, since there are already two urea groups in the chain extender, the distribution has the characteristic features.

To improve the heat resistance of polyurethaneurea, there is a method to enlarge the hard segment of polymer. However, even in the polymer having a hard segment having the same average molecular weight, the polyurethaneurea obtained by the present method, the peak corresponding to the minimum hard constitution unit U2 hard in the hard segment distribution can be made small and the peak corresponding to the U4 hard in the hard segment distribution can be made large, when compared with those obtained from known diamine compounds and diisocyanate compounds. Furthermore, in the distribution of the hard segment, it is confirmed by a high speed liquid chromatography analysis that the peaks corresponding to U6 hard component or more is small and the distribution becomes more sharp.

Accordingly, since the component corresponding to U2 hard of the polyurethaneurea of the present invention is small, the heat resistance is improved and since the distribution is more sharp, the viscosity stability of the polymer stock solution is good. The hard segment distribution in the polymer can be determined by decomposition by perchloric acid, obtaining of the hard segment portions, followed by determining with a high performance liquid chromatography.

By suitably selecting the treatment conditions in the perchloric acid decomposition, the urethane bonds, ether bonds, and ester bonds are broken with almost no breaking of the urea bonds. When a polyurethaneurea polymer is decomposed by perchloric acid, the hard segments comprised of the urea bonds remain as they are, while the soft segments comprised of the urethane bonds, ether bonds, or ester bonds are decomposed to the low molecular weight monomers Bulletin of the Chemical Society of Japan, H. Suzuki et al. 43, 682-6 (1970), Kogyo Kagaku Zasshi, 72, 7, 1593-7 (1969). The hard segments remaining after this can be precipitated by water and isolated. Specifically, approximately one part by weight of the polymer solids is immersed in 10 ml of 60% perchloric acid and treated by an oil bath of 60° C. for 34 hours with occasional agitation. The treatment solution is returned to room temperature, 100 ml of ion exchange water is added, and the hard segments are precipitated. The precipitate is filtered by a glass filter, then washed on the glass filter by 50 ml of ion exchange water and then 50 ml of 1N sodium hydroxide and then again with 50 ml of ion exchange water. After the washing, the precipitate is dried at 80° C. for 3 hours under reduced pressure to obtain a sample of the hard segments. The fact that the hard segments did not actually decompose was confirmed from the fact that the average molecular weight of the hard segments of the polyurethaneurea polymer before the decomposition, found by $H^1$-NMR, and the average molecular weight of the hard segments decomposed by the perchloric acid and separated matched.

When the hard segments obtained in this way is analyzed by a high speed liquid chromatography, the four main peaks appear. When these peaks are nominated as P1, P2, P3 and P4 from the slow retention time side, it is confirmed by mass spectrometric analysis that U2 hard, U4 hard, U6 hard and U8 hard correspond to P1, P2, P3 and P4 peaks respectively. For example, the parent peak of P2 peak in the MS spectrum is 819, which is derived from the U4 hard.

When the hard segments of various polyurethaneureas are analyzed and when the molecular weight distribution and physical properties of each hard segment are compared based upon the analysis results, it is confirmed that remarkable improvements in the physical properties are observed when the peak area ratio of P2 peak (i.e., corresponding to U4 hard) is at least 40%, more preferably at least 45%, based upon the total hard segments, by a vertical division method. Thus, the characteristics can be widely changed by controlling the distribution of each hard segment peak.

Further, the present inventors discovered a process for the production of a shaped article of a superior high molecular weight polyurethaneurea by using the diaminourea compound having the formula (I) having active hydrogens at the two end groups.

That is, the process of production of the present invention is a process for production of a shaped article of a polyurethaneurea polymer characterized by heat forming a mixture obtained by adding, in an amount satisfying the following relationship, a diaminourea compound having the formula (I) to a polyurethaneurea obtained by causing a reaction of an excess molar amount of an organic isocyanate with a polymer diol of a number average molecular weight of 500 to 100,000, synthesizing an intermediate polymer having an isocyanate group at its end, then causing a reaction of a bifunctional diamine compound and monofunctional amine compound with the intermediate polymer.

The preferable effective amount of the aromatic diaminourea compound having the formula (I) is the amount satisfying the following equation:

$$0.005 \leqq A/B \leqq 3$$

wherein, A is the molar amount added of the diaminourea compound having the above-mentioned formula (I) and B is the molar amount of the monofunctional amine used for the production of the polyurethaneurea polymer.

The preferred shaped article of the polyurethaneurea is a fiber or film.

The diaminourea compound having the formula (I) and used in the present invention differs from the known conventional compound having the formula (VIII) in that it is a compound having highly reactive active hydroxyl groups at its two ends. Therefore, an amine exchange reaction is caused with the highly reactive monofunctional amine constituting the end urea group used for the production of the polyurethaneurea at the time of the heat formation by a relatively low heat energy. That is, the two end urea groups of the polyurethaneurea and the two end urea groups having the highly reactive active hydroxyl groups of the diaminourea compound having the formula (I) and used in the present invention undergo an amino exchange reaction at the time of heat formation, and the polyurethane urea is easily made higher in molecular weight, it was learned. That is, compared with the case of production by the technique of using the known conventional, stable aromatic diurea compound having the formula (VIII), the effect of increasing the molecular weight of the polymer is larger and therefore the elastic characteristics and heat resistance of the elastomer obtained are superior. Further, in the process of the present invention, since the molecular weight is increased in a straight chain manner, it appears that there is no three-dimensional bonding reaction causing a three-dimensional cross-linking structure in the polyurethaneurea, caused in the known art, or if any are few in number, so there is little reduction of the strength during knotting. Further, the stringiness of the spinning stock solution does not decline and there is little yarn breakage in the spinning chimney during spinning.

The mixed composition of the polyurethaneurea obtained by adding and mixing the diaminourea compound having the formula (I) used in the present invention is excellent in the viscosity and other aspects of storage stability at a temperature of less than about 45° C. During heat formation, it increases in molecular weight for the first time.

The heat formation temperature required for increasing the molecular weight is 50° C. to 350° C. When a solvent is used and the formation is performed in a short period, generally a temperature greater than the boiling point of the solvent is used. The formation time may be shorter the higher the temperature. For example, in the case of producing fiber by dry spinning using hot air of close to 200° C. to 300° C., the time of residence in the spinning chimney for formation is sometimes less than one second. On the other hand, at a relatively low temperature, 10 odd seconds or sometimes several tends of seconds are required. Compared with the case of production by the conventional, known art using the stable aromatic diurea compound having the formula (VIII) of the known art, less heat energy is required.

The preferable molar amount (A moles) of the diaminourea compound having the formula (I), used in the present invention, added to the polyurethaneurea with respect to the molar amount (B moles) of the monofunctional amine used in the production of the polyurethaneurea added and mixed in may be found by the following equation, that is, $0.005 \leqq A/B \leqq 3.0$, preferably $0.05 \leqq A/B \leqq 2.0$, more preferably $0.1 \leqq A/B \leqq 1.0$.

Outside of this range, the effect is insufficient. That is, if the ratio of the molar amount (A moles) added of the diaminourea compound having the formula (I) to the molar amount (B moles) of the monofunctional amine used in the production of the polyurethaneurea added and mixed in is small (that is, $A/B < 0.005$), the effect of imparting a high molecular weight to the shaped article of polyurethaneurea is not sufficiently exhibited and the improvement in performance is small.

In the opposite case (that is, $A/B > 3$), since an excess of the diaminourea compound having the formula (I), the bifunctional diamine, functions as the end groups, so in the same way as above, the effect of imparting a high molecular weight to the shaped article of the polymer is not sufficiently exhibited and the improvement of the performance is small.

Further, if the added diaminourea compound having the formula (I) remains in an unreacted state in the mixed and added polyurethaneurea polymer, when a fiber is formed, there is bleeding, which causes fiber scum and causes trouble such as yarn breakage during knitting of fabrics etc. As examples of the polyurethaneurea polymer used in the present invention, mention may be made of those obtained by the method described above. The bifunctional diamine compound used during the polymerization of the polyurethaneurea may be a known one. The diaminourea compound of the present invention may be used alone or in a mixture.

EXAMPLES The present invention will now be further illustrated by, but is by no means limited to, the following Examples.

First, the process of production of the diaminourea compound of the present invention will be shown.

Note that the apparatuses and conditions of the measurement performed in the examples and reference examples are as follows:

1) Measurement of infrared absorption spectrum Apparatus: Perkin Elmer 1600 Method: KBr tablet method
2) NMR measurement Apparatus: Nihon Denshi JNM GX 400 Nuclear Magnetic Resonance Spectrometer Method: $^1$H-SGNON Accumulation: 100 times Measurement frequency: 4000 Hz Solvent: DMSO-$d_6$ Measurement temperature: 27° C., or Apparatus: Nihon Denshi JNM PMX-60 Standard substance: Tetramethylsilane (TMS) Measurement temperature: 37° C. Solvent: DMSO-$d_6$
3) Measurement of melting point Apparatus: Yanagimoto Seisakusho MP-500 Speed of temperature rise: 3+ to 4° C./min, melting point confirmed visually
4) FABMS measurement Apparatus: Nihon Denshi JMS-HX110 Acceleration voltage: 10 kV Scan range: 50 to 2000 Cycle time: 60 seconds Resolution: 1000 Matrix: Nitrobenzylalcohol:glycerine =6:4 Sampling: DMSO

Reference Example 1

Example of Synthesis of Compound (A) (having Formula (XIII))

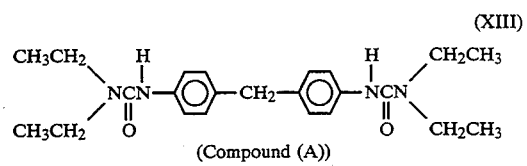

(Compound (A))

A mixture of 400 g of diethylamine (i.e., "DEA") and 500 ml of tetrahydrofuran (i.e., "THF") was agitated in a separable flask. Into this was slowly dropped at room temperature, by a dropping funnel, 200 g of methane diphenylene diisocyanate (i.e., "MDI") dissolved in 500 ml of tetrahydrofuran. Along with the dropwise addition, a precipitate was formed. After the end of the dropwise addition, the solution continued to be agitated for one hour at room temperature. The precipitate was filtered, then washed with tetrahydrofuran, and dried at room temperature under reduced pressure. Three hundred grams of a white powder, that is, compound (A), was obtained.

Yield: 95% Melting point: 179° to 181° C.

The infrared absorption spectrum of this compound is shown in FIG. 1.

Example 1

Example of Synthesis of Compound (1) (Formula (IX)) of Present Invention

Sixty grams of the compound (A) obtained in Reference Example 1 and 400 g of ethylenediamine (i.e., "EDA") (melting opint 116° C.) were agitated in a round bottom flask with a distillation tube and slowly heated. The compound (A) completely dissolved in the ethylenediamine, which then began to boil. After about 10 minutes, the temperature of the top of the distillation tube was 60° to 70° C., close to the boiling point temperature of the ethylenediamine, and a distillate began to run out. After 22.1 g of distillate, that is, the theoretical run-off of diethylamine, ran off, the top temperature became 114° to 118° C. (liquid temperature of 116° to 120° C.), near the boiling point of the diethylamine. At this time, the heating was stopped and the solution was sufficiently cooled, then the reaction solution was dried under reduced pressure at 60° C. (aspirator 12 Torr). The result was washed by tetrahydrofuran and filtered, then the result was dried under reduced pressure at room temperature by a vacuum pump, whereupon 48 g of the white powder of compound (1) was obtained.

Yield: 85% Melting point: 288° to 306° C.

Figure 2:
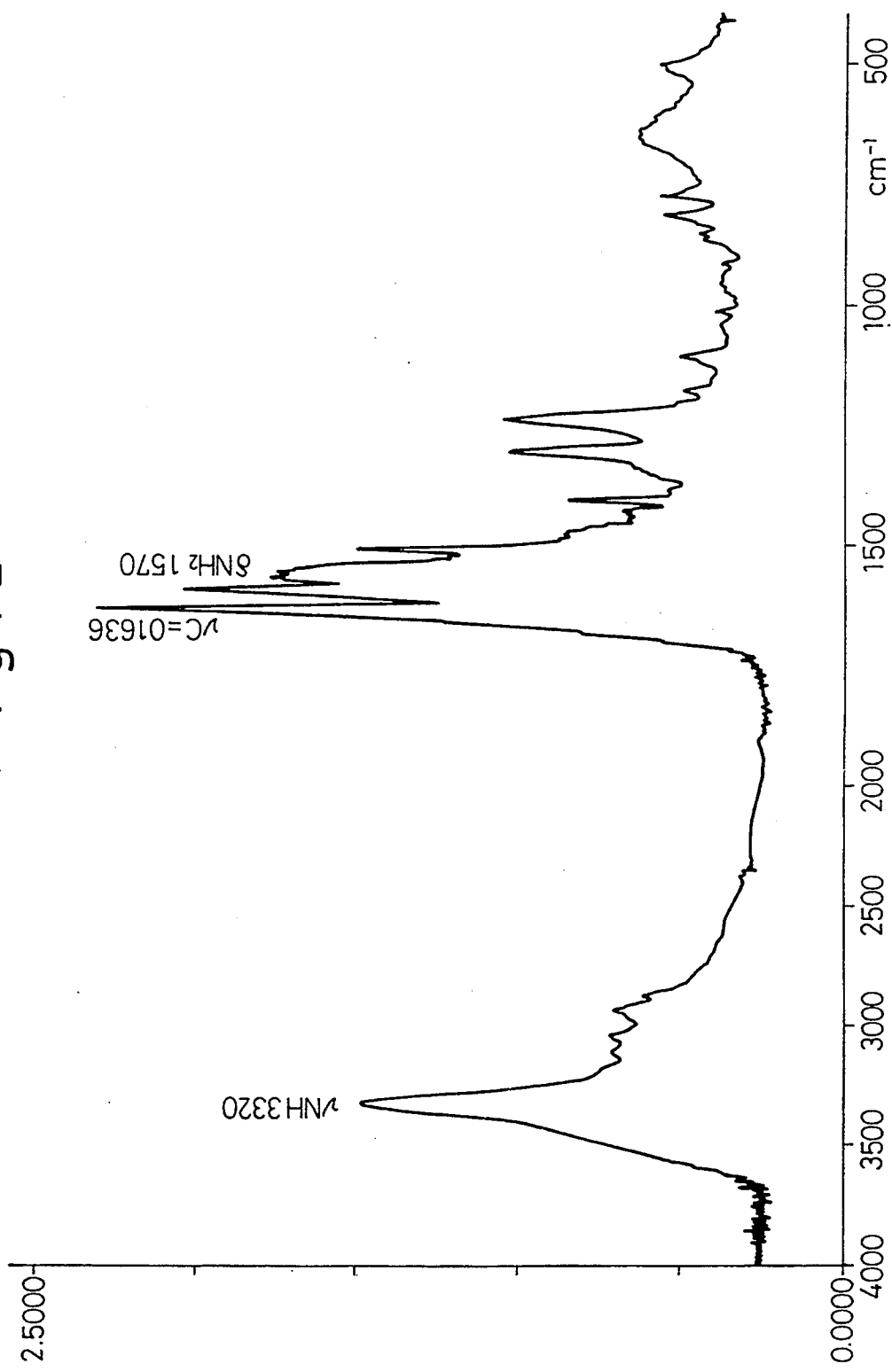
FIG. 2 is the infrared absorption spectrum of the compound (1)
Figure 3:
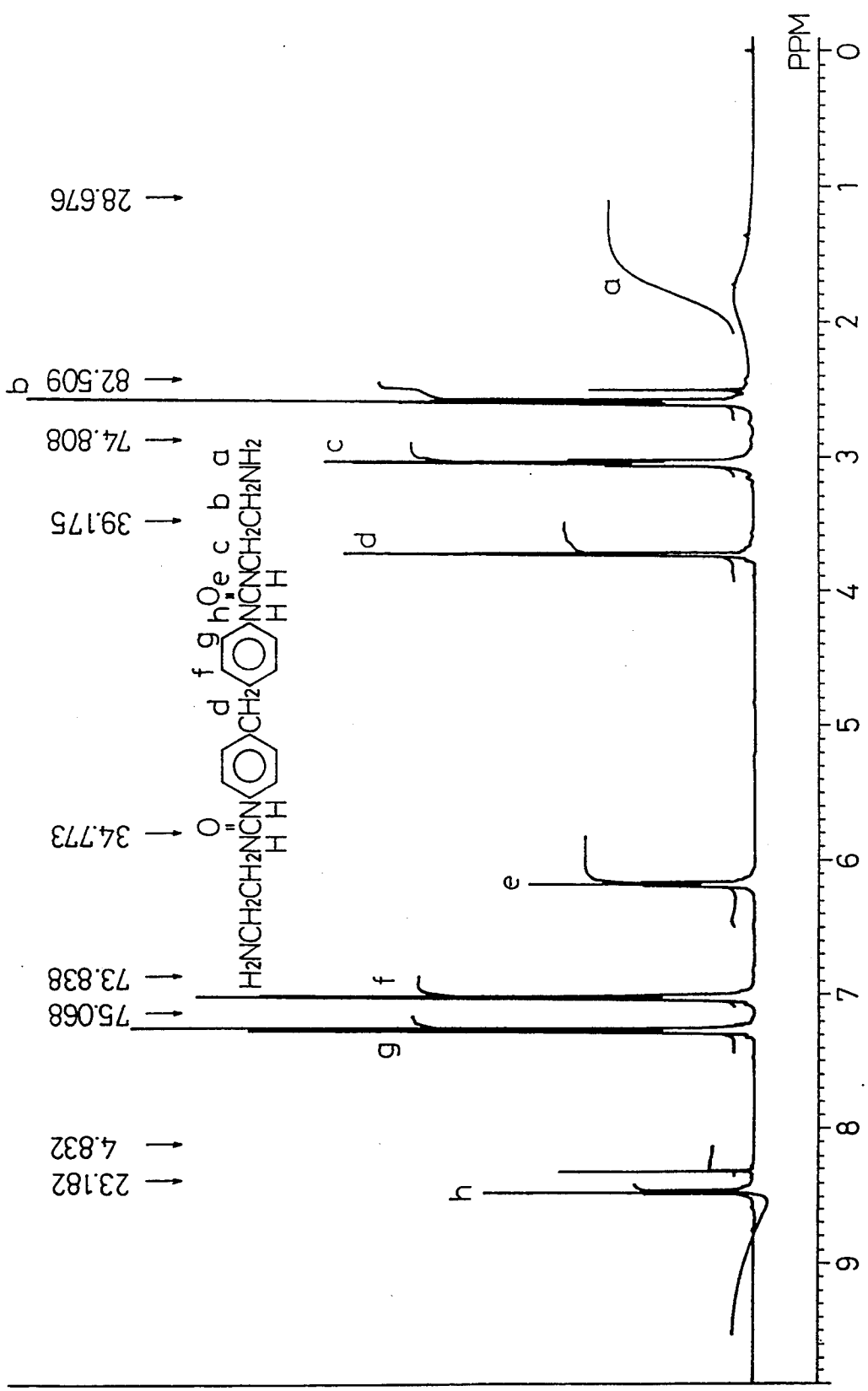
FIG. 3 is the $^1$H-NMR spectrum of the compound (1)
Figure 4:
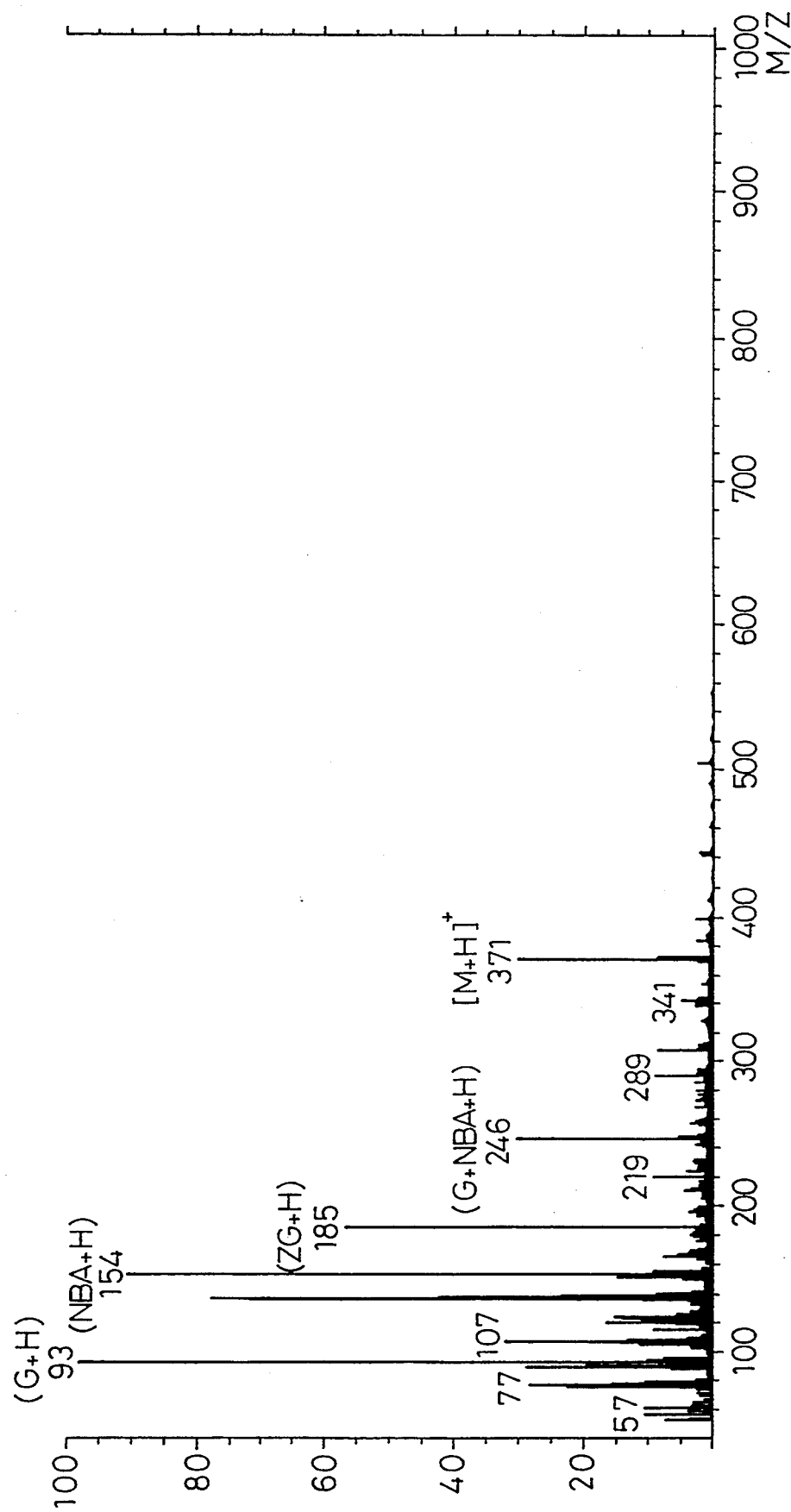
FIG. 4 is the MS spectrum of the compound (1)

The infrared absorption spectrum, the $^1$H-NMR spectrum, and the FABMS spectrum of this compound are shown in FIG. 2, FIG. 3, and FIG. 4, respectively. The measurement of the FABMS confirmed that the molecular weight was 370 (FIG. 4). Further, in the infrared absorption spectrum of FIG. 2, the absorption (1081, 1165 cm$^{-1}$) derived from the tertiary amine seen in the infrared absorption spectrum (FIG. 1) of the compound (A) disappeared due to the procedure of Example 1, the absorption (1570 cm$^{-1}$) derived from the primary amine appeared, and it was shown that the compound (1), a diaminourea compound, was produced. Further, in FIG. 3 too, as shown in the figure, signals of —CH$_2$—, —CH$_2$—, —NH— are seen at 2.6, 3.05, 3.74, and 6.19 ppm, showing the structure of a compound (1) with one amino group of EDA connected by urethane bonds.

Example 2

Example of Synthesis of Compound (2) (Previously Mentioned Chemical Formula (X))

Using the same method as in Example 1 but using 494 g of 1,2-propylenediamine instead of ethylenediamine, 44 g of the compound (2) was obtained.

Yield: 73% Melting point: 292° to 297° C.

Figure 5:
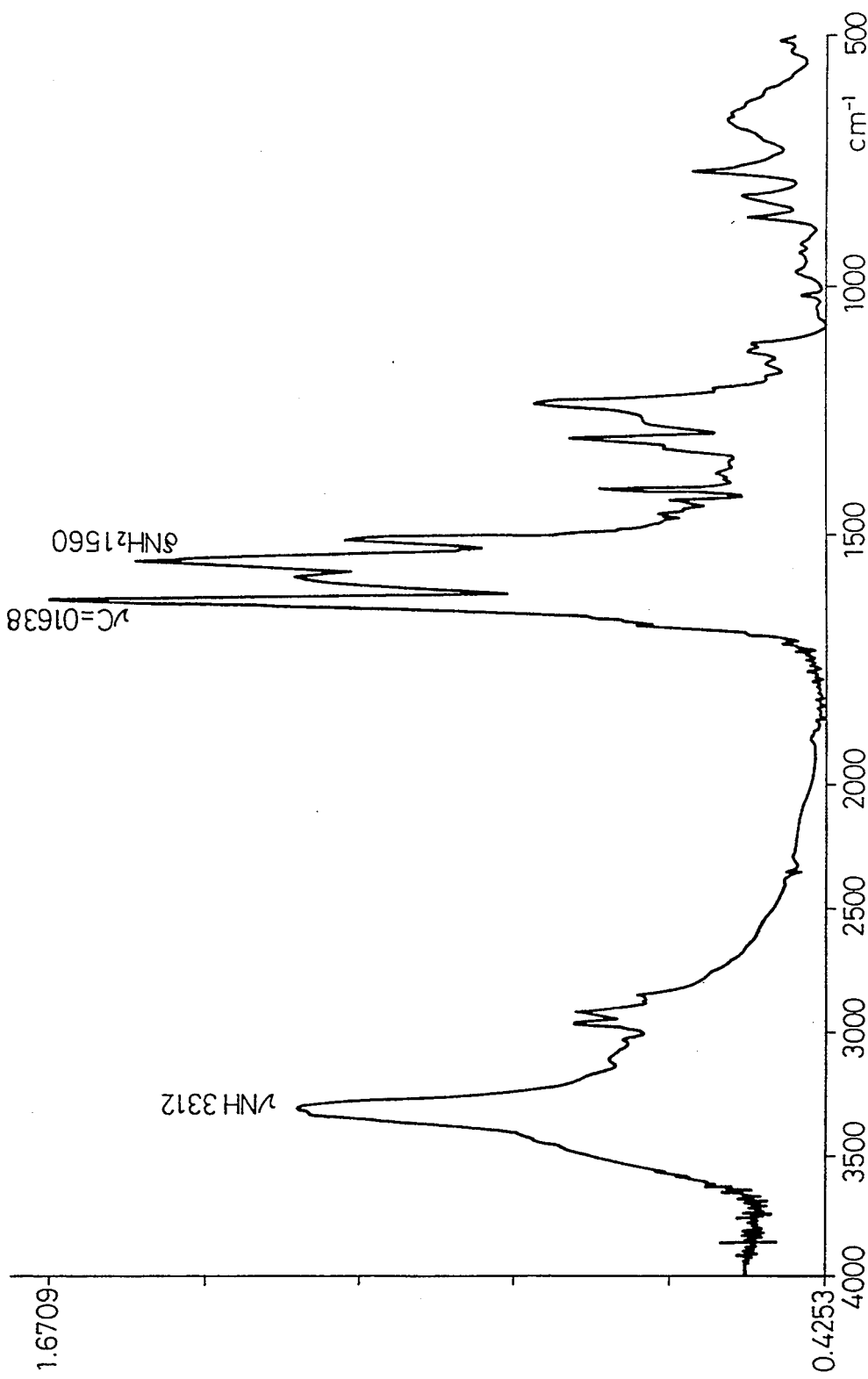
FIG. 5 is the infrared absorption spectrum of the compound (2)

FIG. 5 shows the infrared spectrum of this compound.

In the same way as with the infrared spectrum of the compound (1), the absorption of the tertiary amine disappeared along with the procedure of Example 2, absorption (1560 cm$^{-1}$) of the primary amine appeared, and the structure of the compound (2) was shown. Furthermore, the structure of the compound (2) was confirmed by observing the chemical shift of a methylene group next to an urea group at 2.9 ppm by an NMR determination.

Example 3

Example of Synthesis of Compound (3) (Previously Mentioned Chemical Formula (XI))

Ten grams of the compound (A) obtained in Reference Example 1 and 58.7 g of 1,6-hexamethylene-diamine were added to 200 g of xylene. In the same way as with Example 1, the solution was heated, cooled, and dried under reduced pressure, then the result was washed with water and tetrahydrofuran and filtered, then dried under reduced pressure to obtain 9.74 g of the compound (3).

Yield: 80% Melting point: 287° to 291° C.

Figure 6:
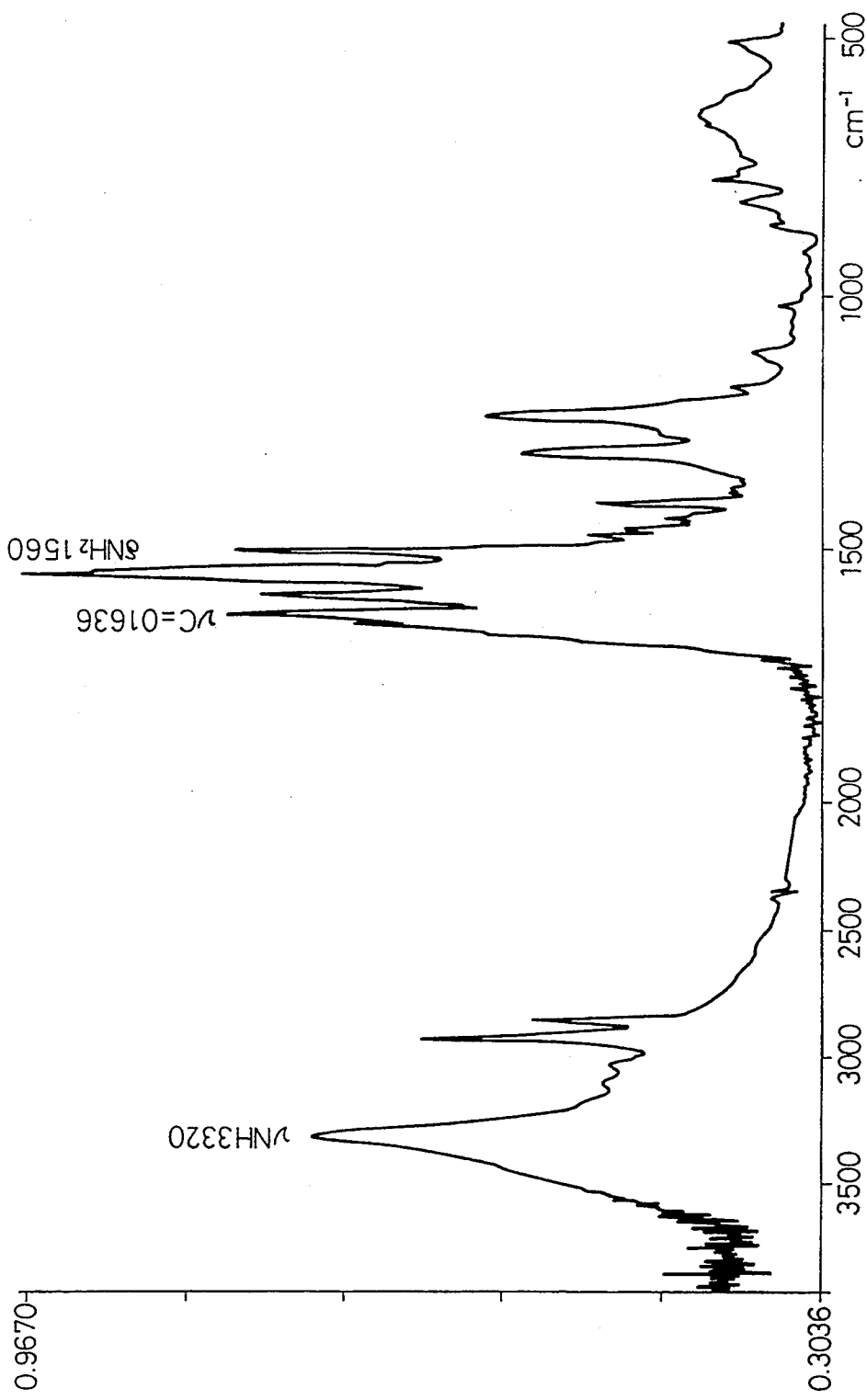
FIG. 6 is the infrared absorption spectrum of the compound (3)

FIG. 6 shows the infrared absorption spectrum of this compound.

In the same way as with the infrared spectrum (FIG. 2 of the compound (1), the absorption of the tertiary amine disappeared along with the procedure of Example 3, absorption (1560 cm$^{-1}$) of the primary amine appeared, and the structure of the compound (3) was shown.

Reference Example 2

Example of Synthesis of Compound (B) (Following Chemical Formula (XIV))

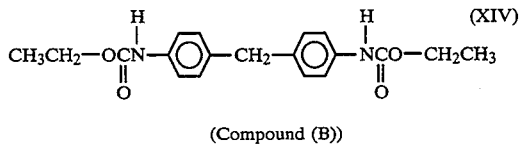

(Compound (B))

The same procedure was performed as in Reference Example 1, except that use was made of 307 g of ethyl alcohol instead of the diethylamine in Reference Example 1, thereby obtaining 255 g of the above-mentioned compound (B).

Figure 7:
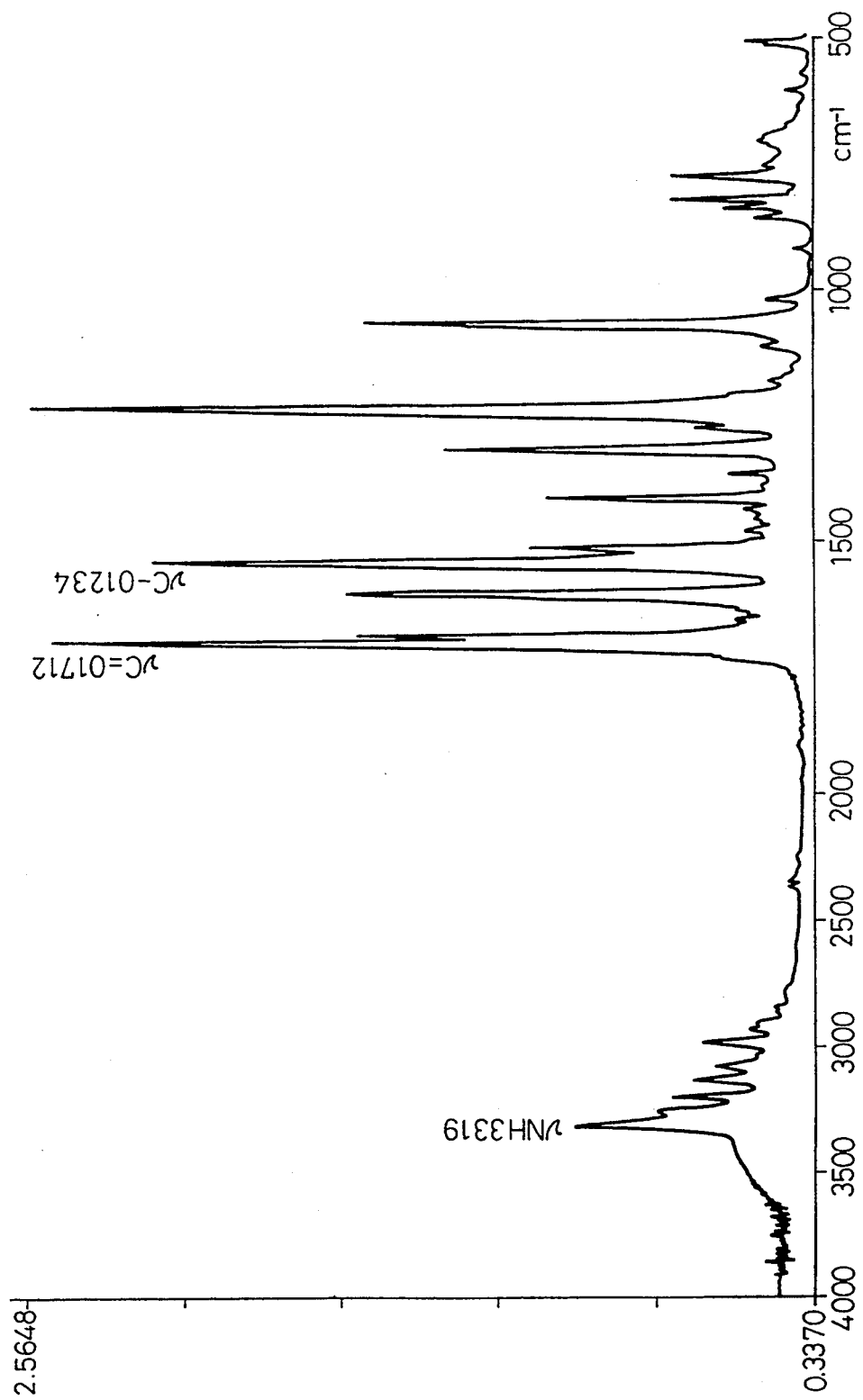
FIG. 7 is the infrared absorption spectrum of the compound (B)

Yield: 93% Melting point: 124° to 128° C. The infrared absorption spectrum of this compound is shown in FIG. 7.

Example 4

Example of Synthesis of Compound (1)

The same procedure was performed as in Example 1 except for use of 51.8 g of the compound (B) obtained in Reference Example 2 instead of the compound (A) in Example 1, thereby obtaining 37 g of the compound (1).

Yield: 66% Melting point: 290° to 309° C.

Figure 8:
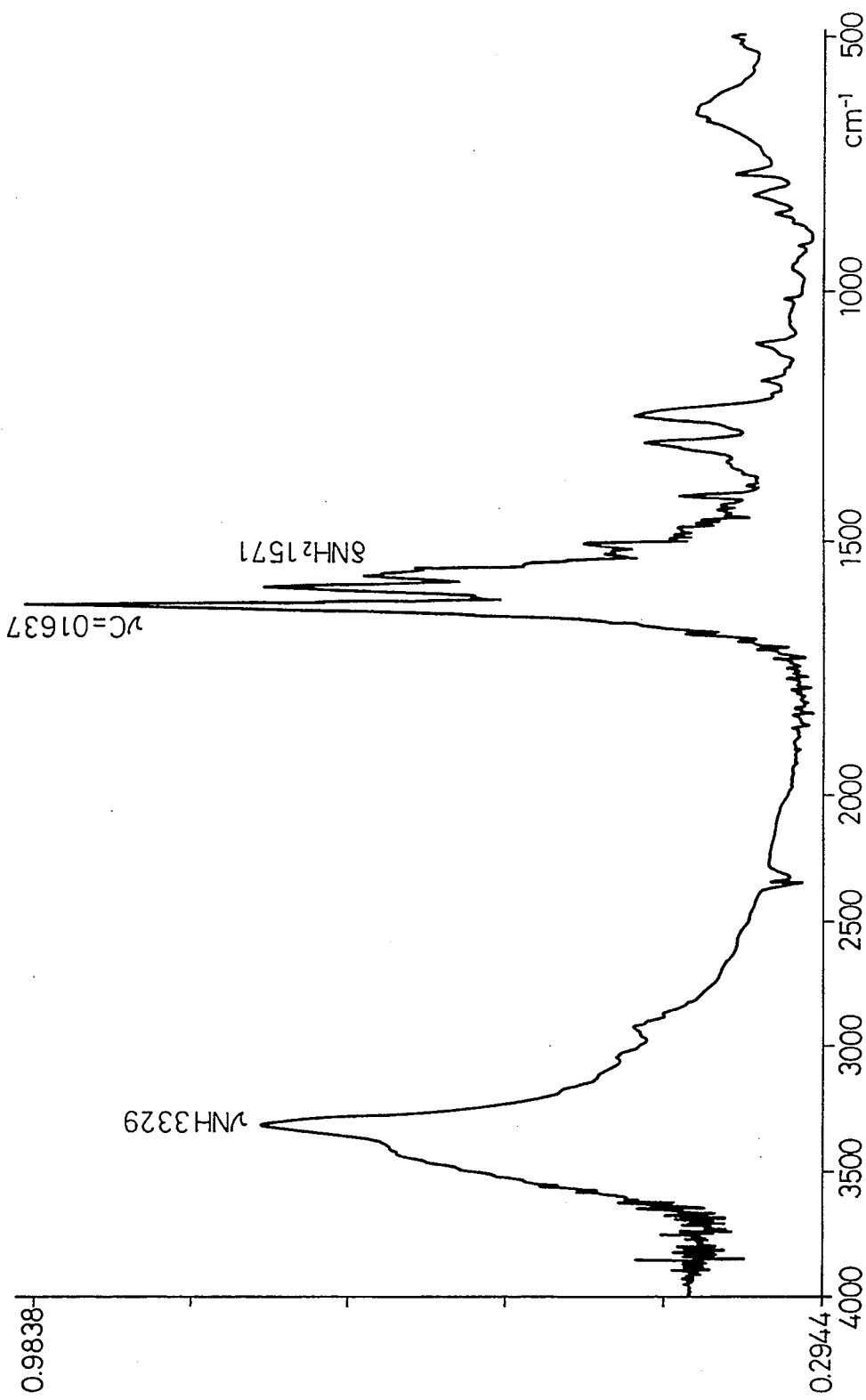
FIG. 8 is the infrared absorption spectrum of the compound (1) obtained in Example 4.

The infrared absorption spectrum of this compound is shown in FIG. 8.

In the infrared absorption spectrum of FIG. 8, the absorption (1234 cm$^{-1}$) derived from the urethane bonds seen in the infrared absorption spectrum (FIG. 7) of the compound (B) disappeared due to the procedure of Example 4, the absorption (1571 cm$^{-1}$) derived from the primary amine appeared, and it was shown that the compound (1), a diaminourea compound, was produced.

Reference Example 3

Example of Synthesis of Compound (C) (Following Chemical Formula (XV))

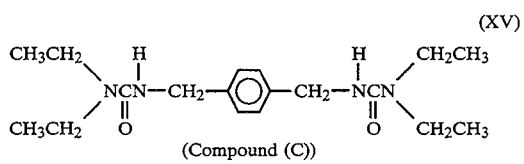
(Compound (C))

A mixture of 20 g of diethylamine and 20 ml of tetrahydrofuran was agitated in a 100 ml Erlenmeyer flask. Into this, 8.24 g of m-xylylene diisocyanate dissolved in 20 ml of tetrahydrofuran was added drop-wise slowly by a dropping funnel at room temperature. After the end of the dropwise addition, the solution continued to be agitated for one hour at room temperature. Thirty ml of tetrahydrofuran was added, the precipitate was filtered and was washed with tetrahydrofuran and then dried under reduced pressure at room temperature. A 8.11 g amount of the white powder of the compound (C) was obtained.

Yield: 57% Melting point: 129° to 130° C.

Figure 9:
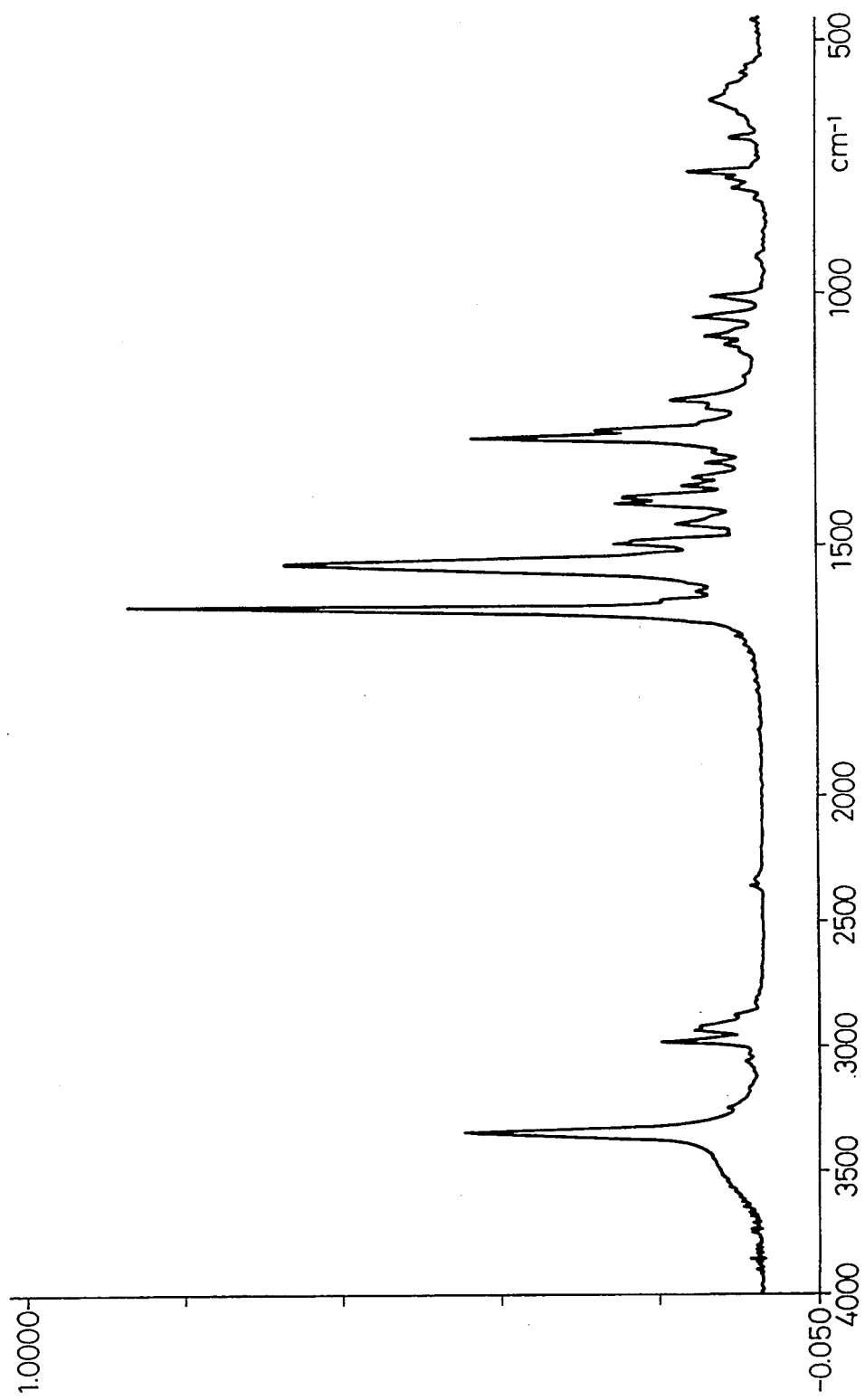
FIG. 9 is the infrared absorption spectrum of the compound (C)

The infrared absorption spectrum of this compound is shown in FIG. 9.

Reference Examples 4 and 5

Examples of Synthesis of Compound (D) and Compound (E) (Following Chemical Formulas XVI and XVII)

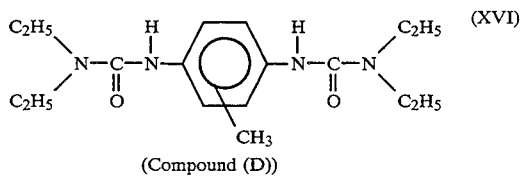
(Compound (D))

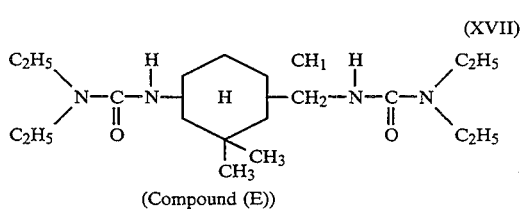
(Compound (E))

Instead of the 8.24 g of m-xylylene diisocyanate in Reference Example 3, use was made of 7.62 g of toluene-2,4-diisocyanate in Reference Example 4 and 9.72 g of isophorone diisocyanate in Reference Example 5. For the rest of the procedure, the same procedure as in Reference Example (3) was performed to obtain 10.81 g and 10.94 g of the white powders of compounds (D) and (E).

Compound (D) Yield: 77% Melting point: 164° to 167° C.

Compound (E) Yield: 67% Melting point: 156° to 157° C.

Figure 10:
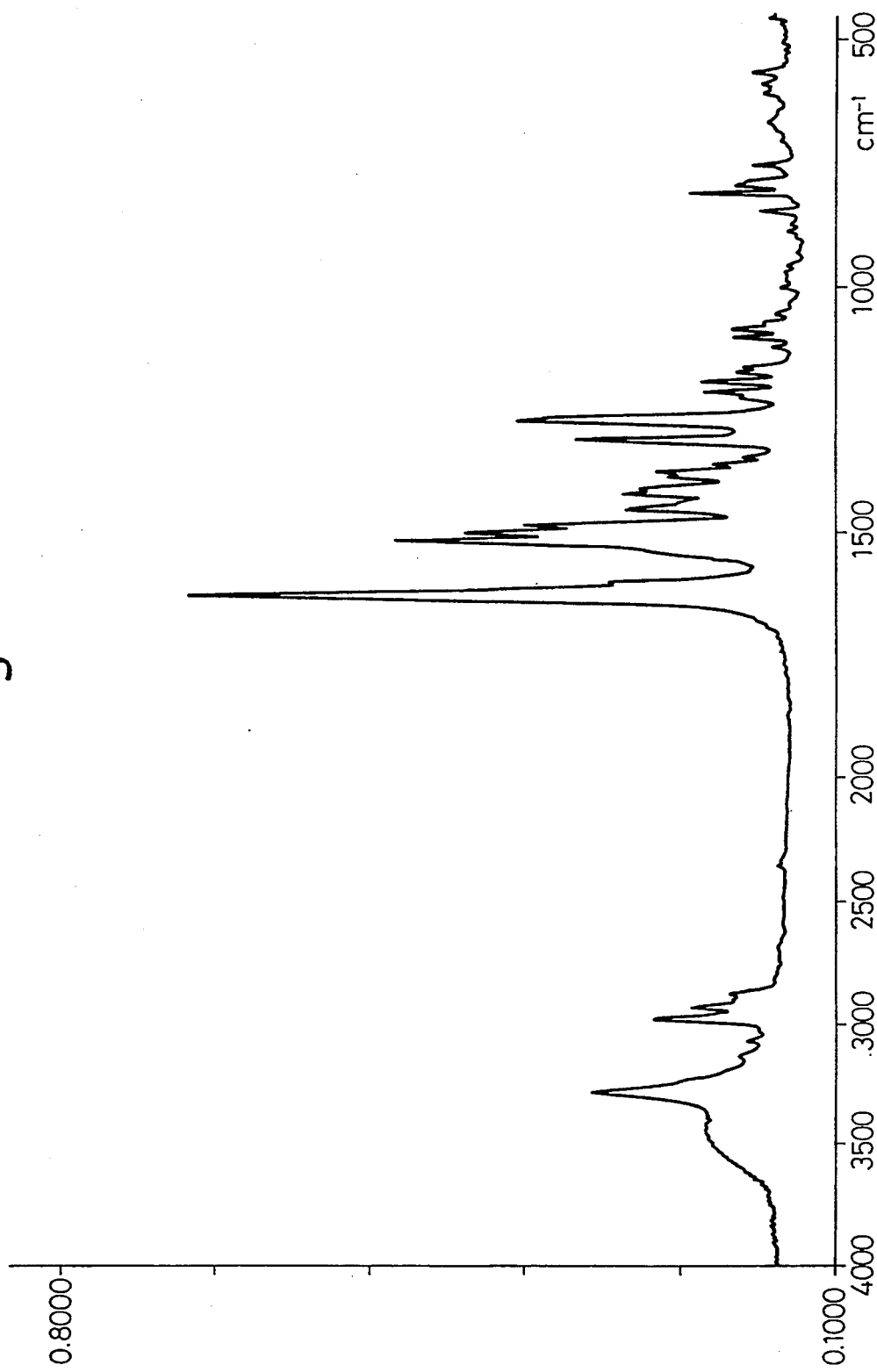
FIG. 10 is the infrared absorption spectrum of the compound (D)
Figure 11:
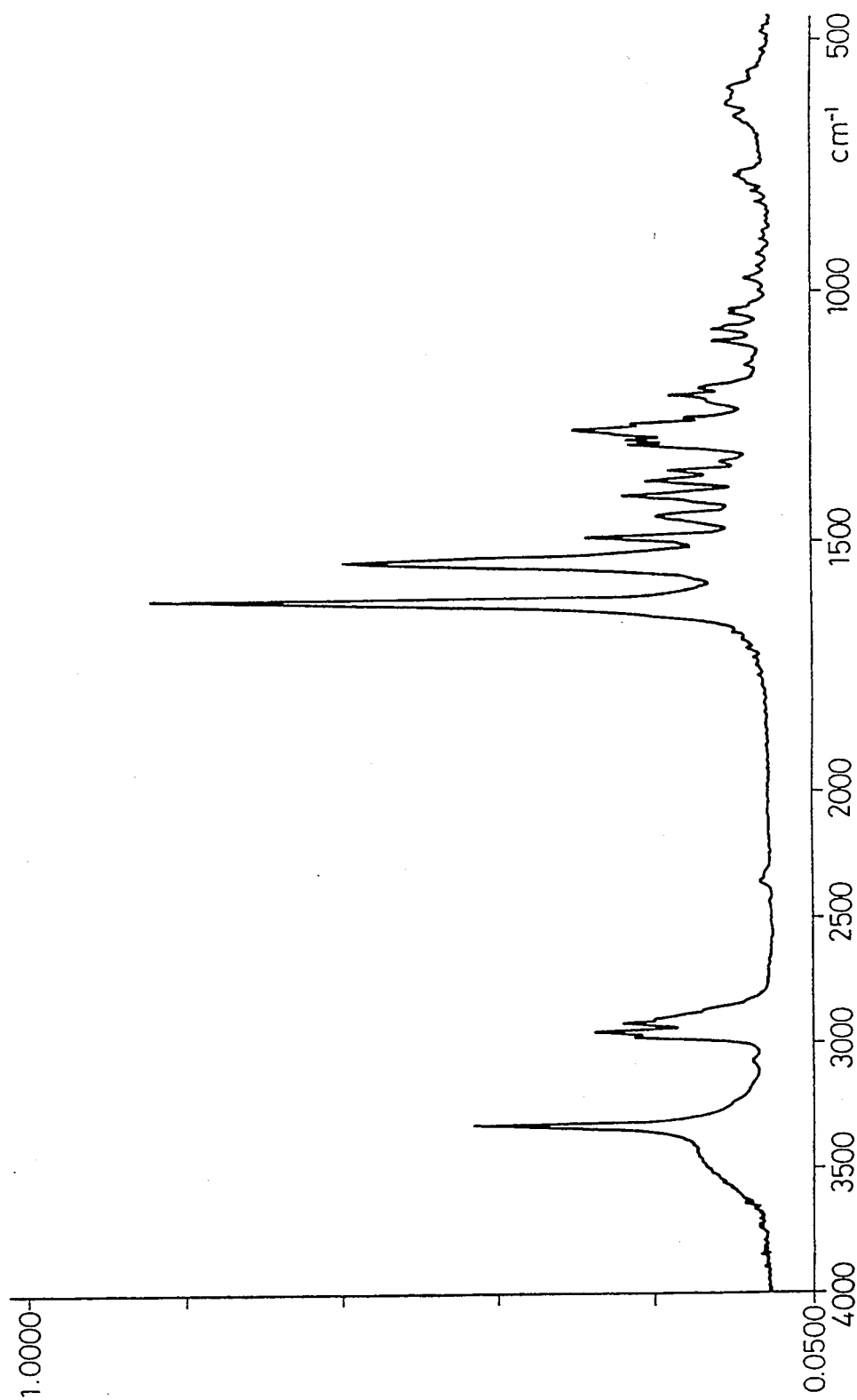
FIG. 11 is the infrared absorption spectrum of the compound (E).

The infrared absorption spectrums of these compounds are shown in FIG. 10 and FIG. 11.

Reference Example 6

Example of Synthesis of Compound (F) (Following Chemical Formula (XVIII))

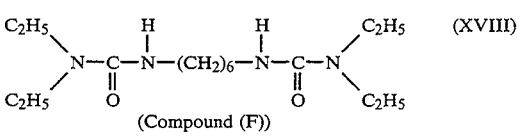
(Compound (F))

Instead of the 8.24 g of the m-xylylene diisocyanate in Reference Example 3, 8.00 g of hexamethylene diisocyanate was added. The rest of the procedure was the same as in Reference Example 3, but after the end of the agitation, agitation was performed for one hour at room temperature, then a temperature of 50° C. was applied by an evaporator to remove the unreacted diethylamine and tetrahydrofuran. A 15.00 g amount of white powder of the compound (F) was obtained.

Yield: 100% Melting point: 107° to 110° C.

Figure 12:
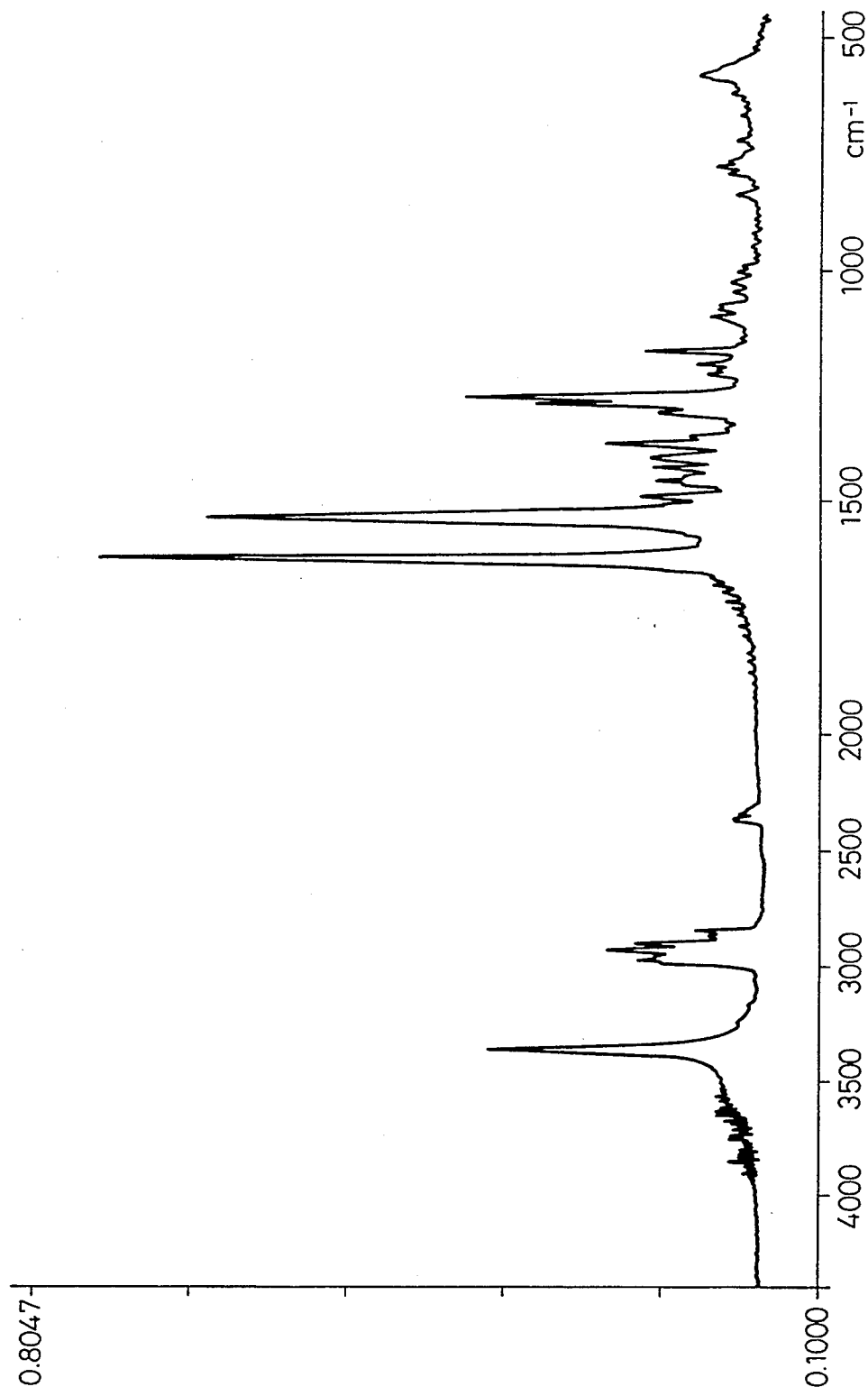
FIG. 12 is the infrared absorption spectrum of the compound (F).

The infrared spectrum of this compound is shown in FIG. 12.

Reference Example 7

Example of Synthesis of Compound (G) (Following Formulae (XIX))

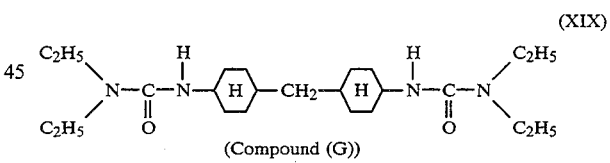
(Compound (G))

The same procedure was performed in Reference Example 3, except that 8.49 g of dicyclohexylmethane diisocyanate was used instead of 8.24 g of m-xylylene diisocylanate in Reference Example 3, thereby obtaining 7.84 g of the compound (G) in the state of white powder.

Yield: 55% Melting point: 150° to 157° C.

Figure 13:
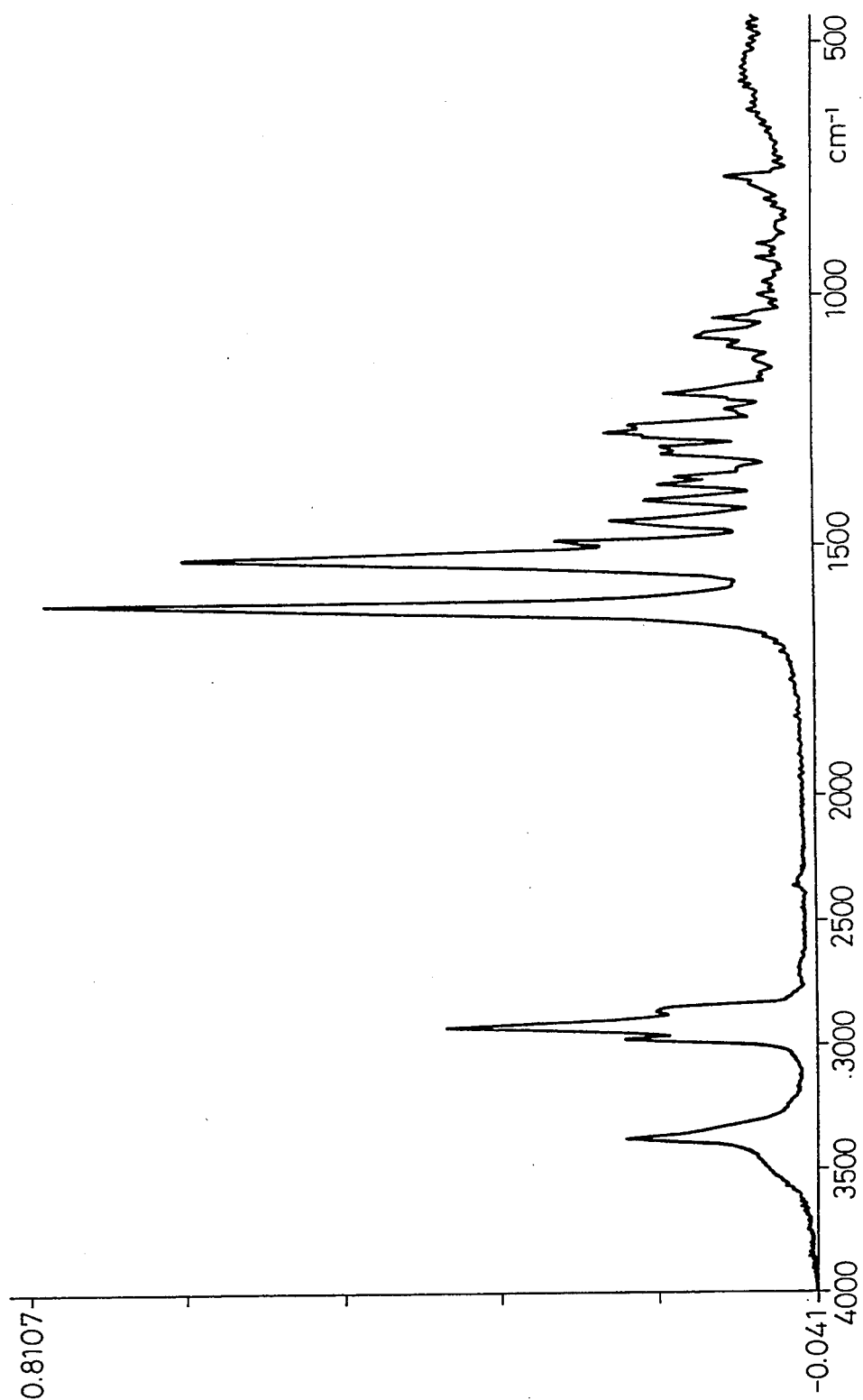
FIG. 13 is the infrared absorption spectrum of the compound (G).
Figure 14:
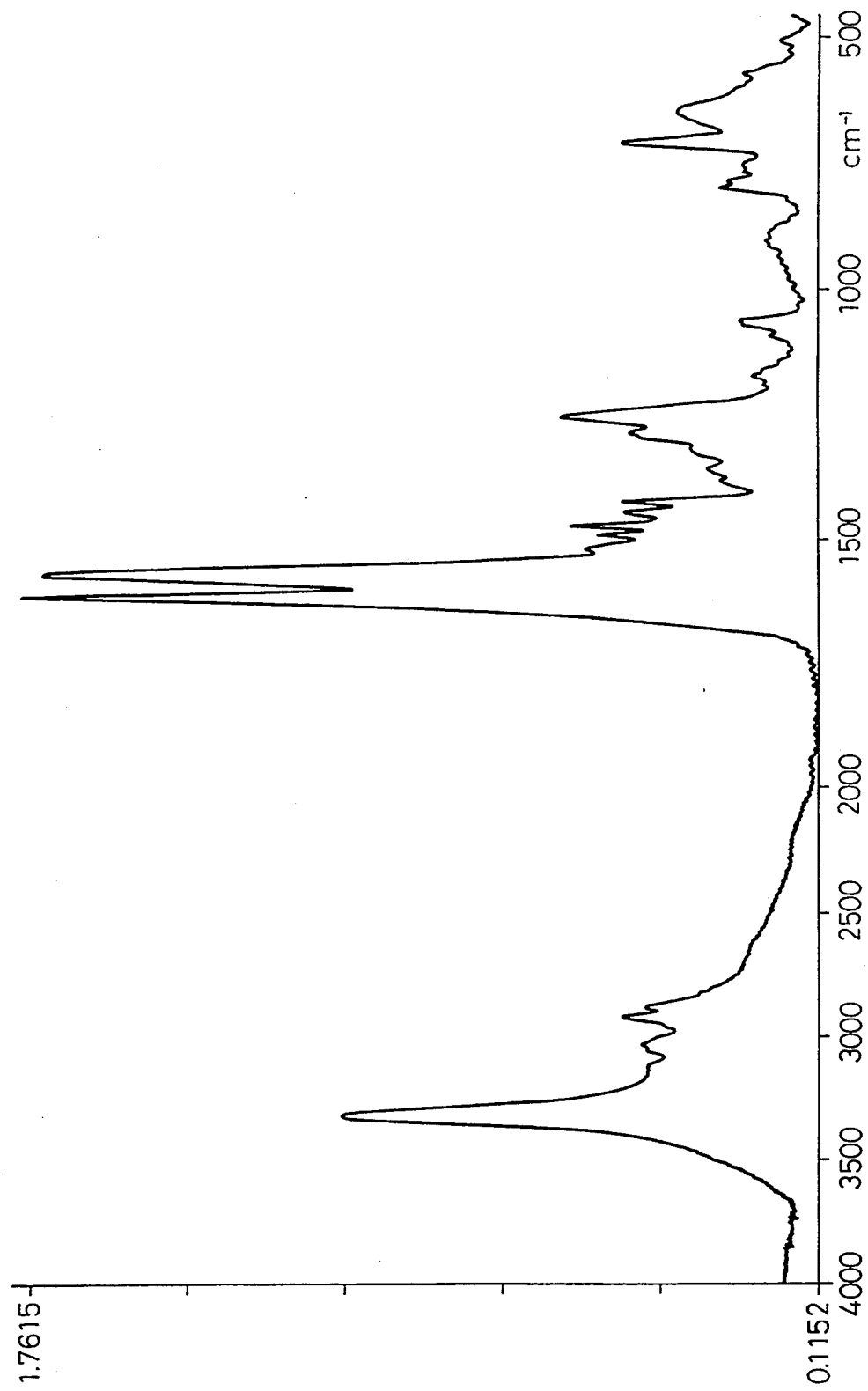
FIG. 14 is the infrared adsorption spectrum of the compound (4)
Figure 15:
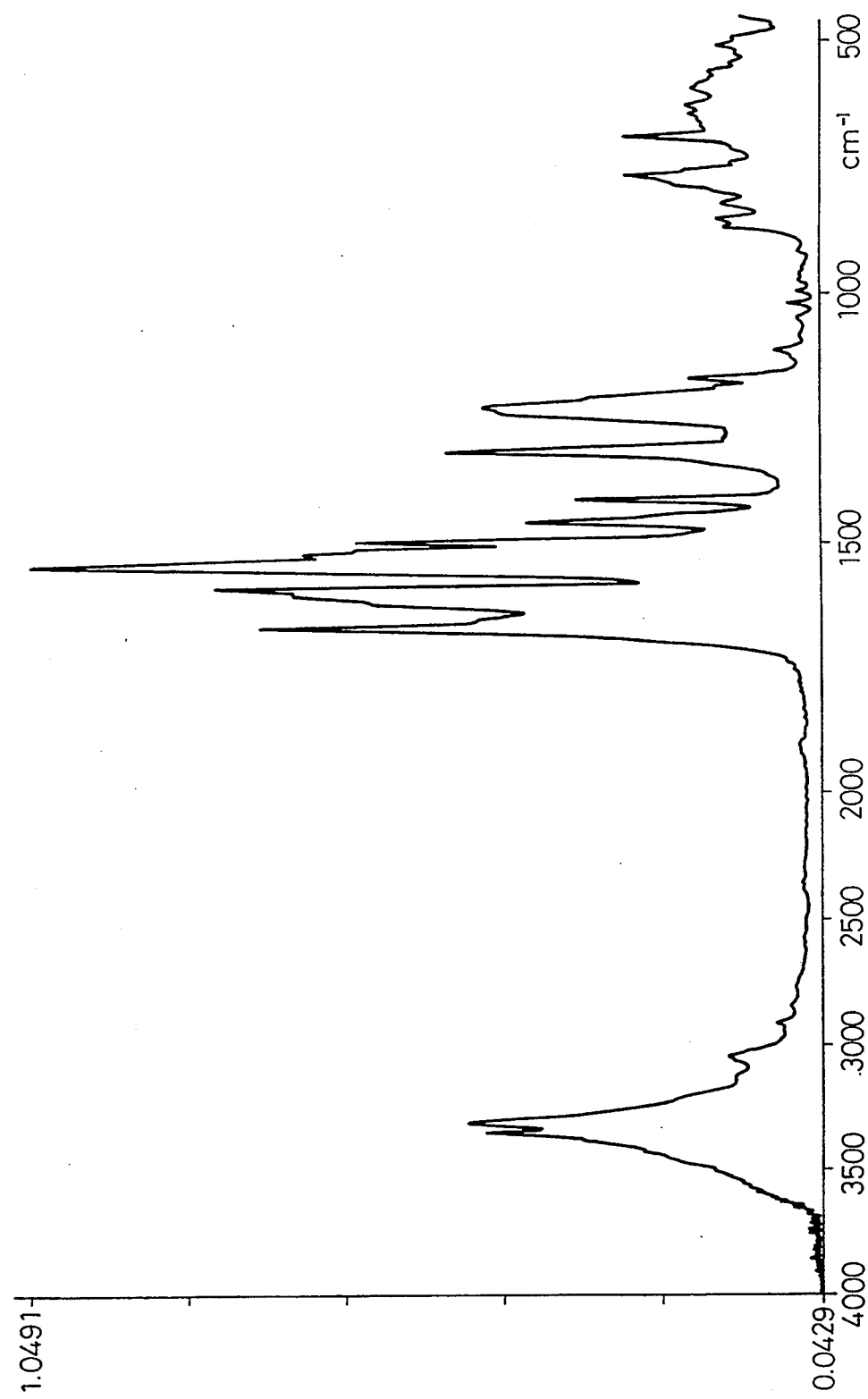
FIG. 15 is the infrared absorption spectrum of the compound (5)
Figure 16:
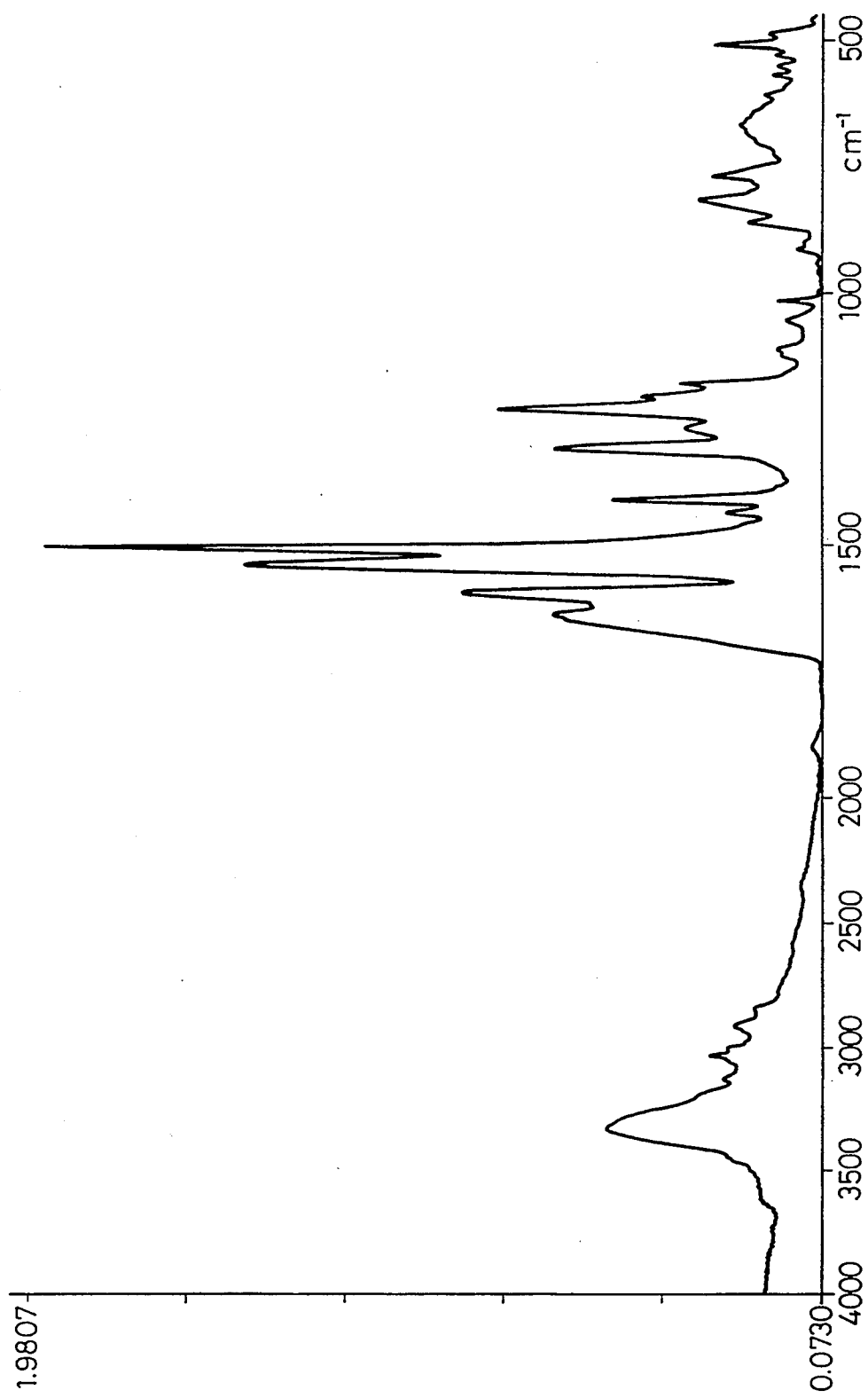
FIG. 16 is the infrared absorption spectrum of the compound (6)
Figure 17:
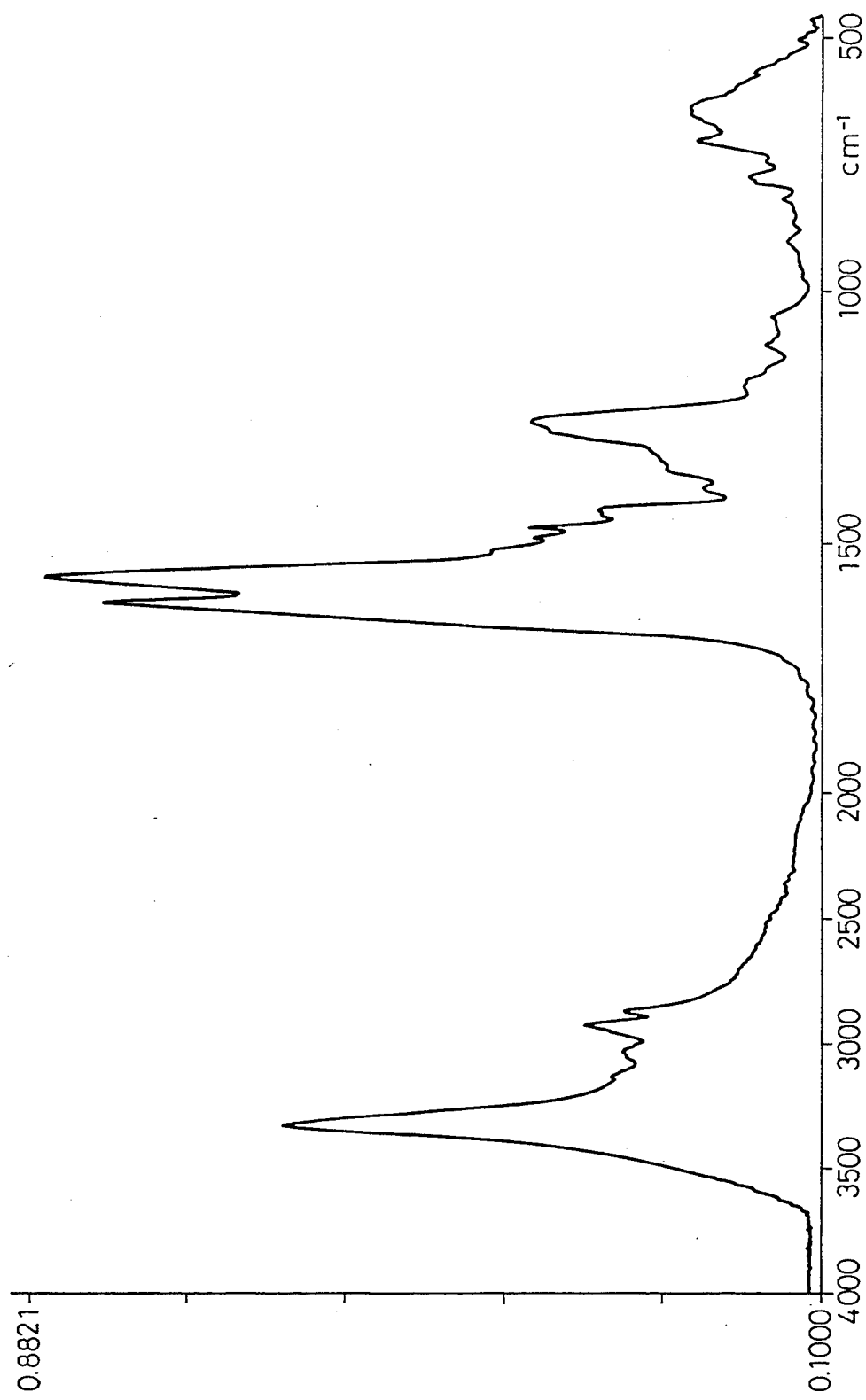
FIG. 17 is the infrared absorption spectrum of the compound (7).
Figure 18:
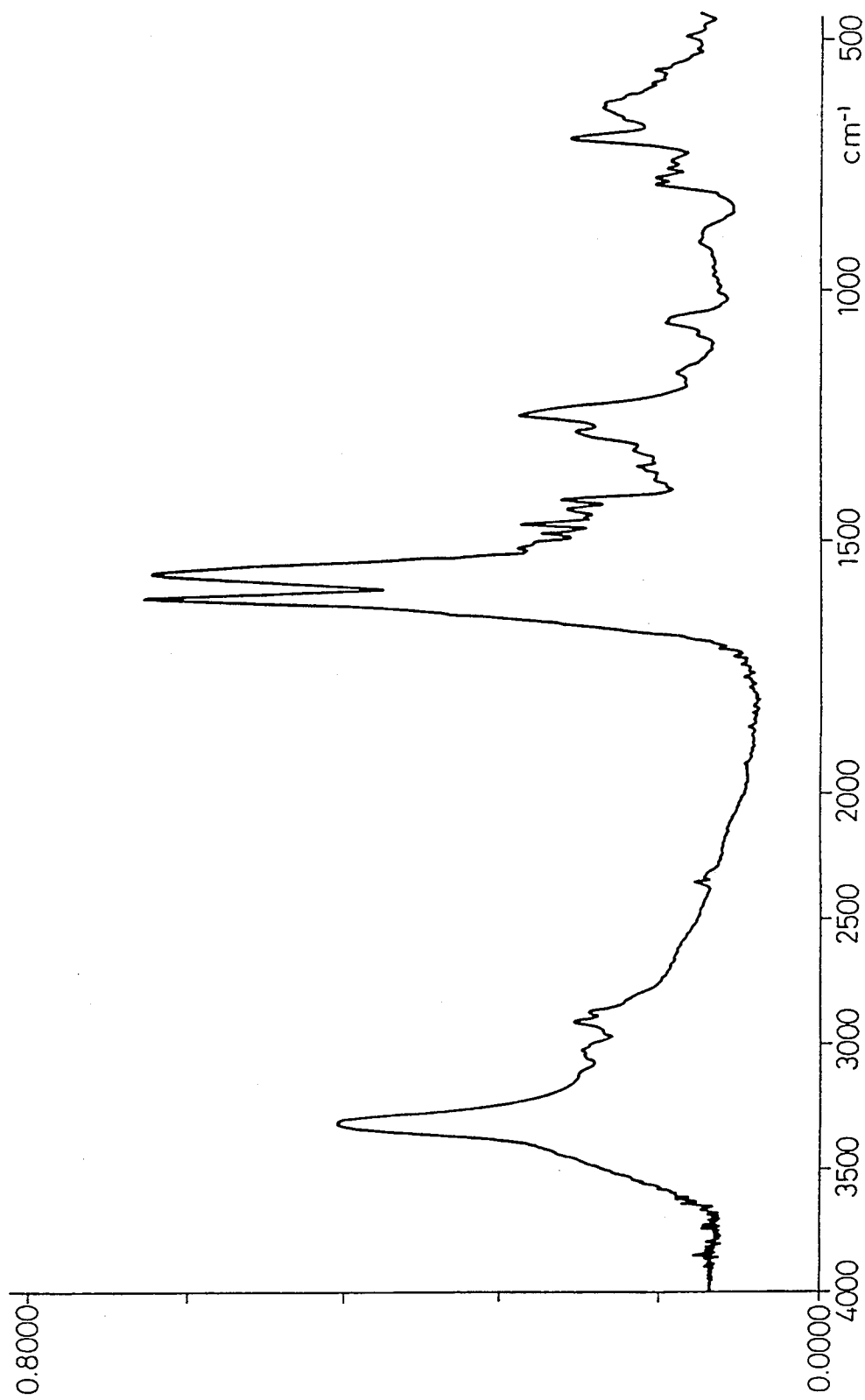
FIG. 18 is the infrared absorption spectrum of the compound (8).
Figure 19:
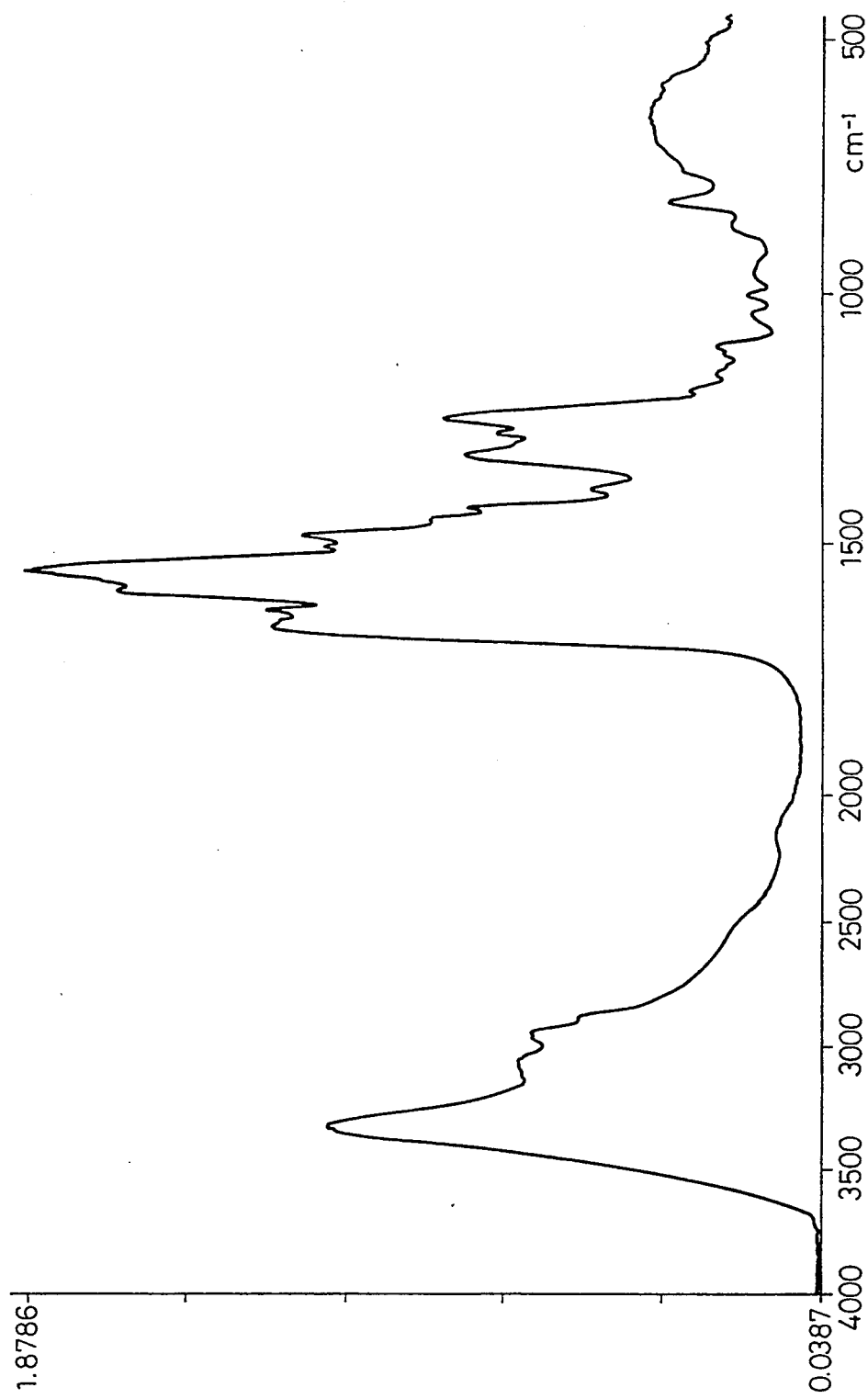
FIG. 19 is the infrared absorption spectrum of the compound (9)
Figure 20:
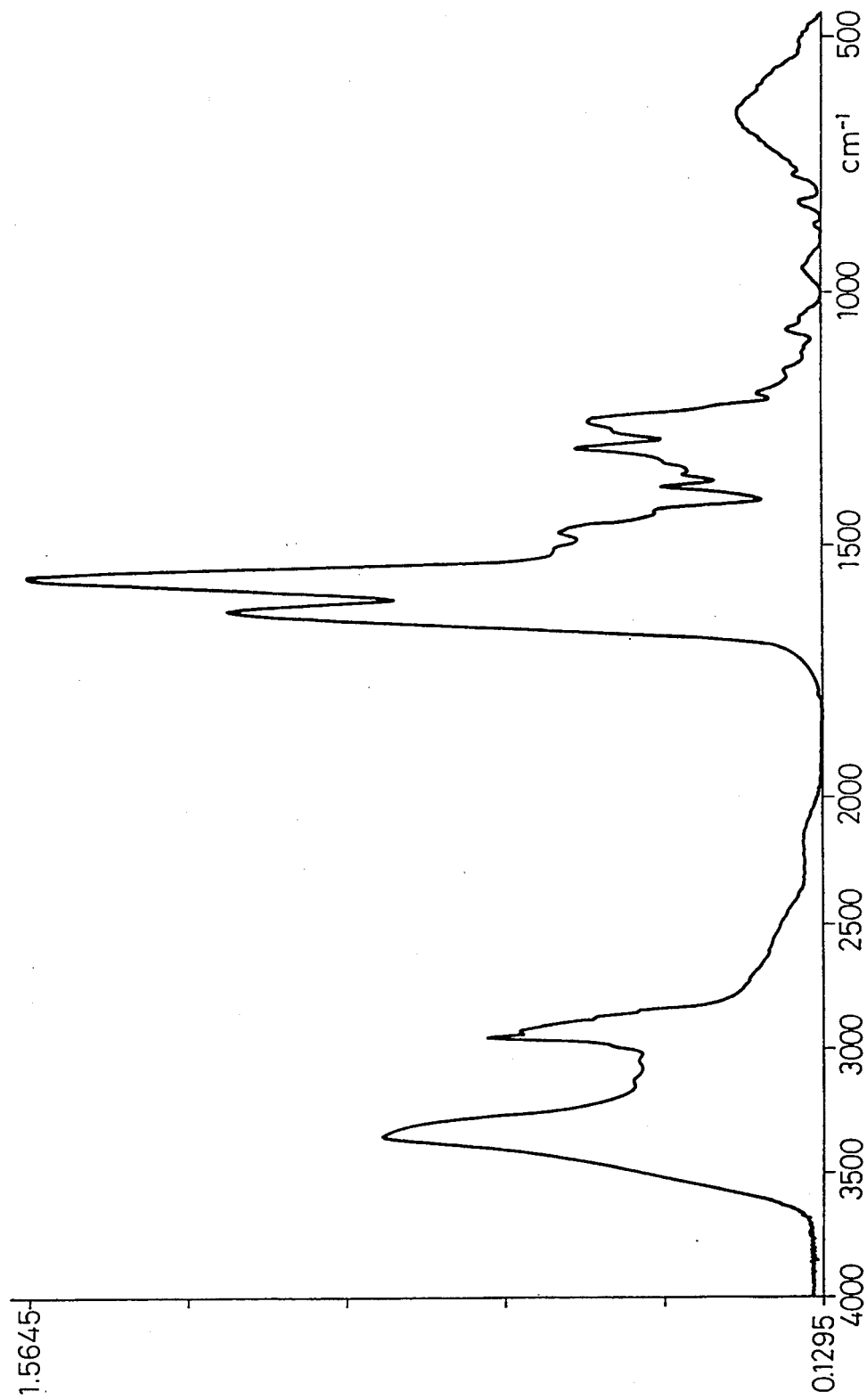
FIG. 20 is the infrared absorption spectrum of the compound (10).
Figure 21:
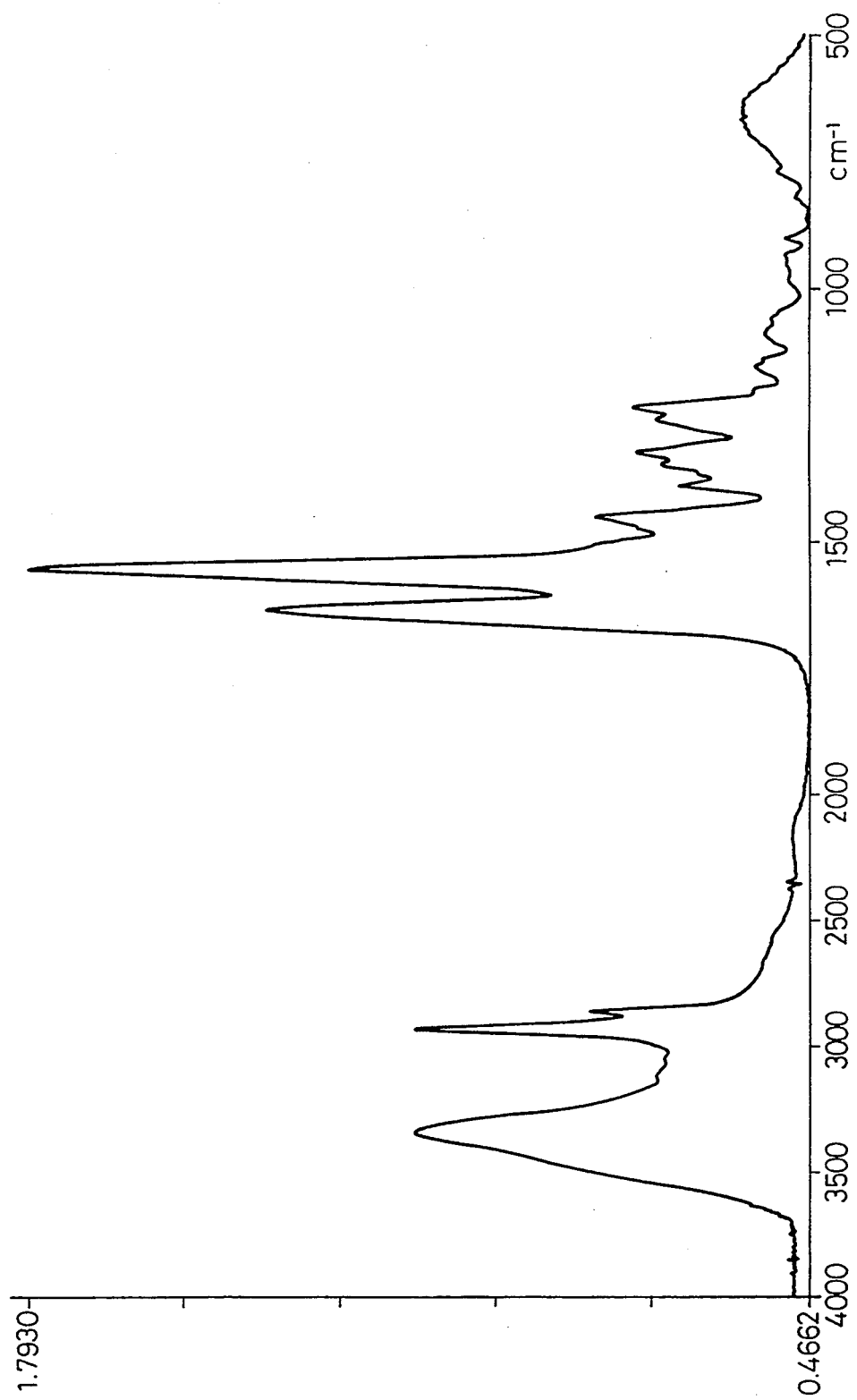
FIG. 21 is the infrared absorption spectrum of the compound (11).
Figure 22:
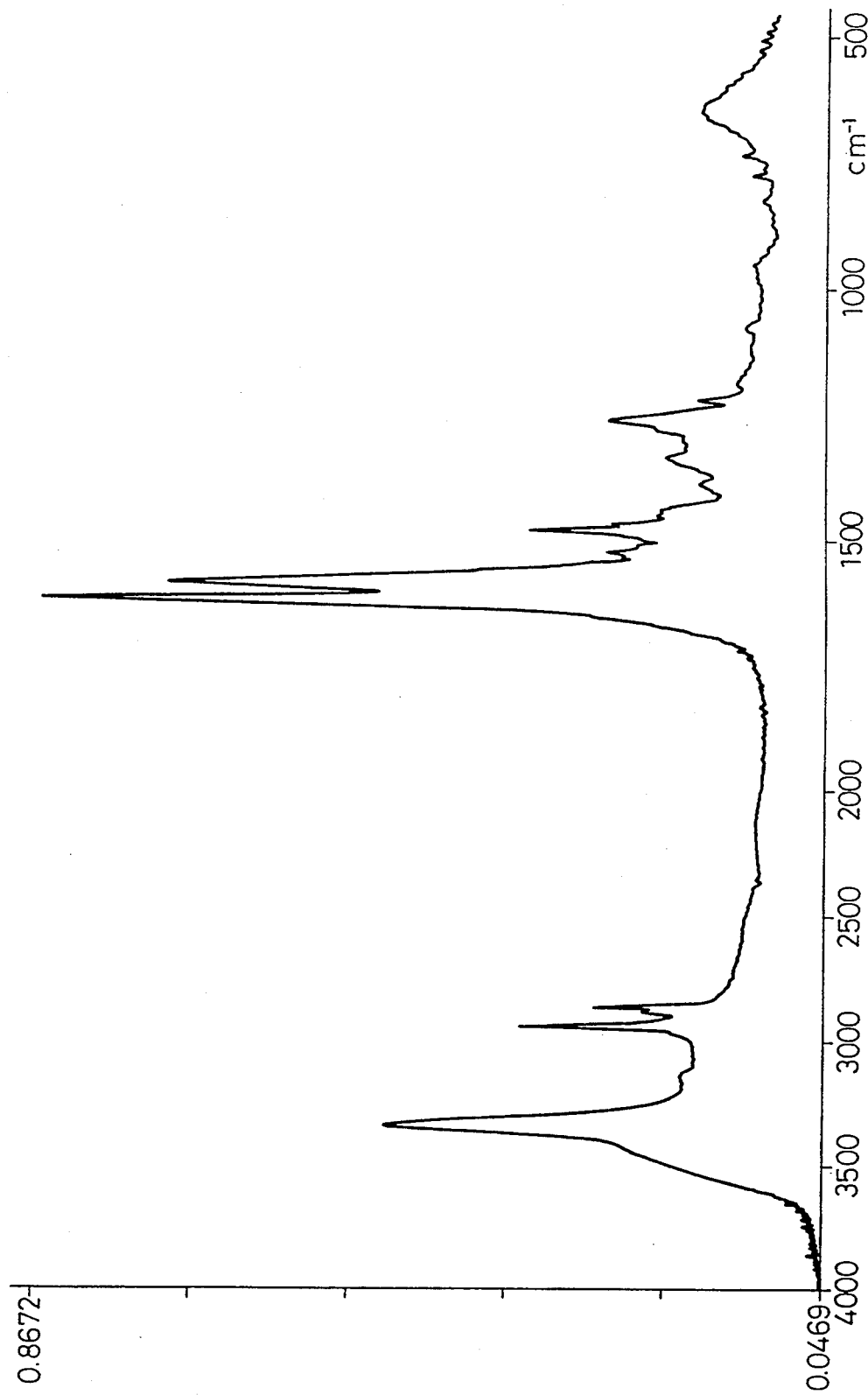
FIG. 22 is the infrared absorption spectrum of the compound (12)
Figure 23:
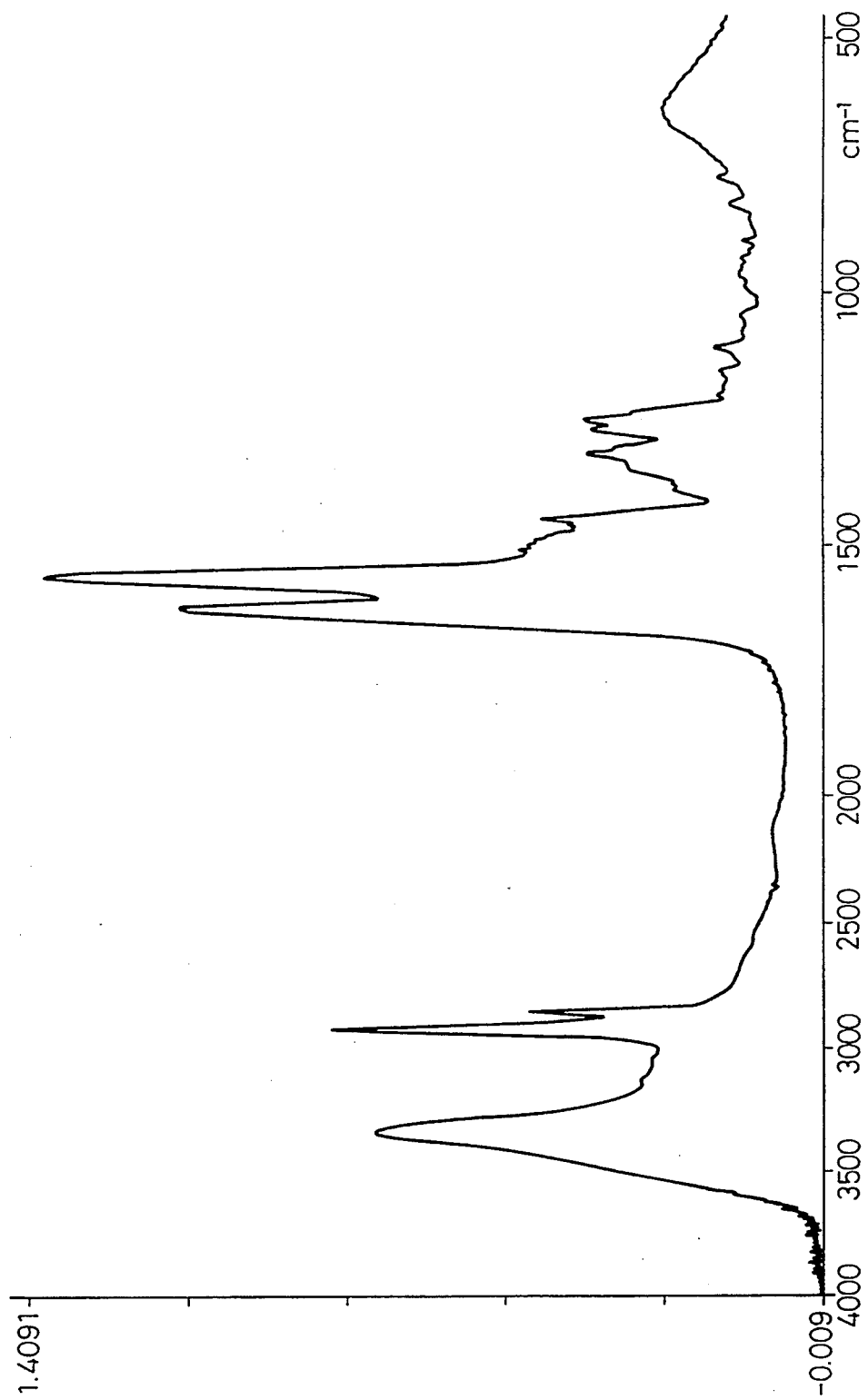
FIG. 23 is the infrared absorption spectrum of the compound (13)
Figure 24:
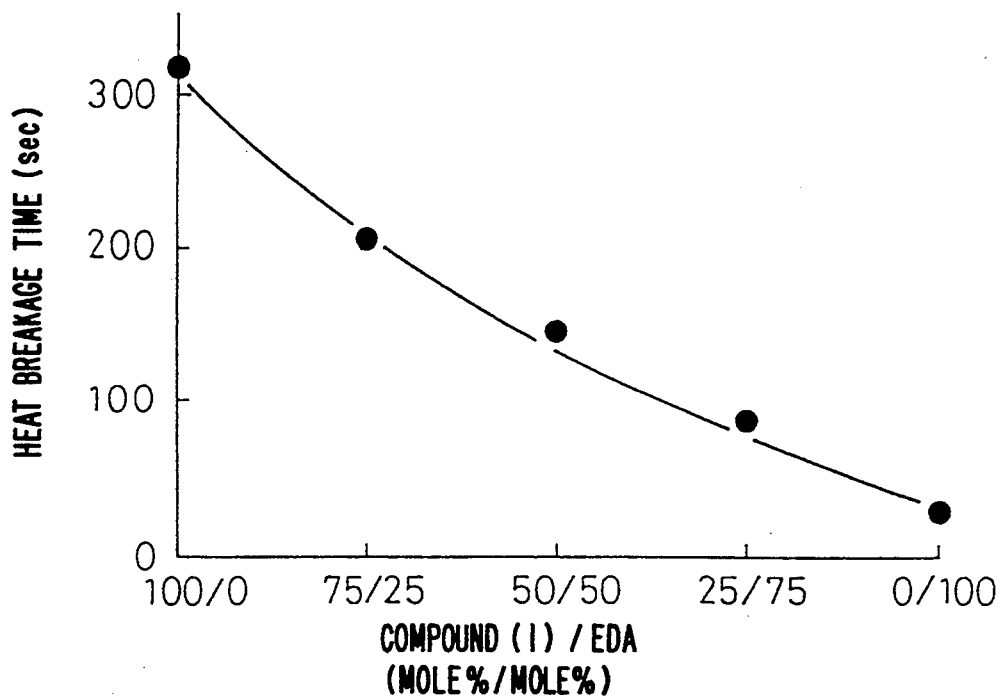
FIG. 24 is a view showing the relationship of the ratio of mixture of the compound (1) and the seconds of heat breakage of film.

The infrared spectrum of this compound (G) is shown in FIG. 13.

The diisocyanate compounds and secondary amines used as starting compounds for the compounds (A) to (G) synthesized in Reference Examples 1–7 are shown in Table 1.

TABLE 1

|  |  | Diisocyanate compound | Secondary amine |
|---|---|---|---|
| Reference Example 1 | Compound (A) | 4,4'-Diphenylmethane diisocyanate | ethylenediamine |
| Reference Example 2 | Compound (B) | " | ethyl alcohol |
| Reference Example 3 | Compound (C) | m-Xylylene diisocyanate | ethylenediamine |

TABLE 1-continued

|  |  | Diisocyanate compound | Secondary amine |
|---|---|---|---|
| Reference Example 4 | Compound (D) | Toluene-2,4-diisocyanate | " |
| Reference Example 5 | Compound (E) | Isoforone diisocyanate | " |
| Reference Example 6 | Compound (F) | Hexamethylene diisocyanate | " |
| Reference Example 7 | Compound (G) | Dicyclohexyl methane diisocyanate | " |

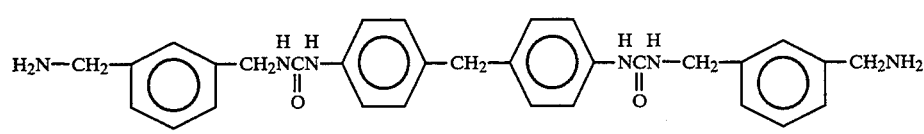

(Compound 4)     (XX)

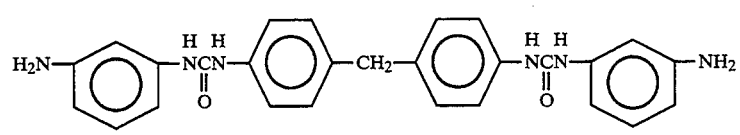

(Compound 5)     (XXI)

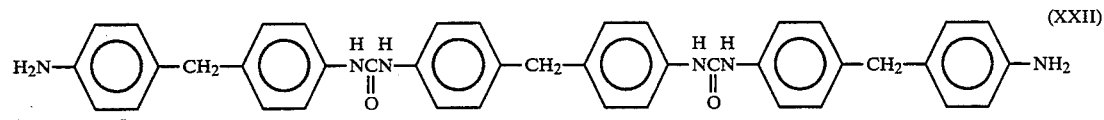

(Compound 6)     (XXII)

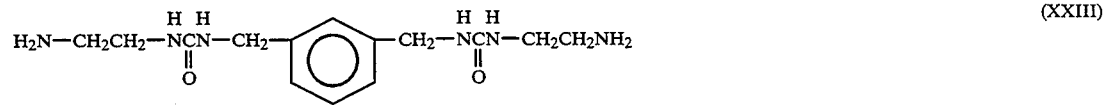

(Compound 7)     (XXIII)

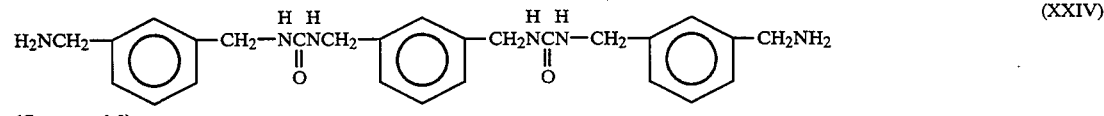

(Compound 8)     (XXIV)

(Compound 9)     (XXV)

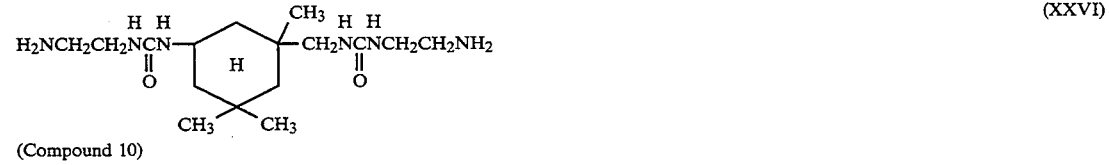

(Compound 10)     (XXVI)

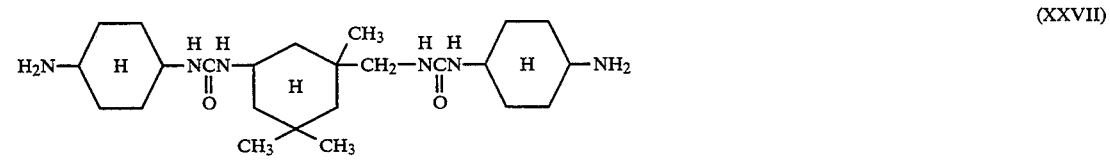

(Compound 11)     (XXVII)

(Compound 12)     (XXVIII)

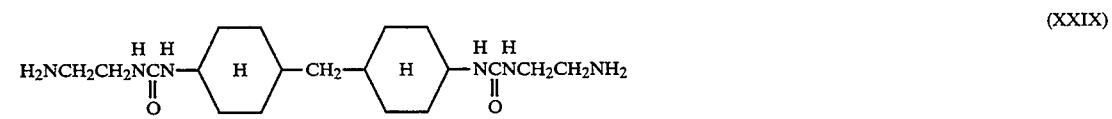

(XXIX)

(Compound 13)

The compounds (A) and (C) to (G) obtained in Reference Examples 1 and 3 to 6 and various types of dismines were charged into Erlenmeyer flasks with distillation tubes attached in the combinations and amounts shown in Table 2, then were slowly heated while agitating them. The compounds (A) and (C) to (G) dissolved in the dismines, which then began to boil. After about one hour, the heating was stopped, the solutions were sufficiently cooled, then 60 ml amounts of tetrahydrofuran were added to cause the reaction products to precipitate. These were washed and filtered with tetrahydrofuran, then dried under reduced pressure at room temperature by a vacuum pump, whereupon white powders of the compounds were obtained. The infrared absorption spectrums of the compounds are shown in FIG. 14 to FIG. 23.

value after heat treatment of the film, use was made of the value of the sectional area of the film before heat treatment.) In the case of a yarn, if one yarn is used for the measurement, the measurement value becomes too small, so five yarns were measured together and that value used as the measurement value. Further, when setting a test piece in the tester after heat treatment, the points 50 mm apart before the treatment are gripped as they are and the piece set at a 50 mm interval.

3) Heat Treatment

The heat treatment was performed by a high temperature high pressure dyeing machine (Nissen Corporation Type 12LMP-E). The 50 mm portion of the test yarn or 2 mm wide test film to be treated was elongated 80% to 90 mm, then immersed in ion exchange water in a pot in the dyeing machine and treated there. The

TABLE 2

|  |  |  | Amount added (g) | Diamine | Amount added (g) | Solvent | Yield (%) | M.P. (°C.) |
|---|---|---|---|---|---|---|---|---|
| Example 1 | Compound (1) | Compound (A) | 60 | Ethylenediamine | 400 | None | 85 | 288–306 |
| Example 2 | Compound (2) | " | 60 | 1,2-Propylenediamine | 494 | " | 73 | 292–297 |
| Example 3 | Compound (3) | " | 10 | Hexamethylenediamine | 58.7 | " | 80 | 287–291 |
| Example 5 | Compound (4) | " | 1.0 | m-Xylylenediamine | 10.0 | " | 70 | — *1) |
| " | Compound (5) | " | 1.0 | m-Phenylenediamine | 5.5 | Toluene | 83 | — *1) |
| " | Compound (6) | " | 1.0 | 4,4'-Diphenylmethanediamine | 10.0 | " | 83 | — *1) |
| " | Compound (7) | Compound (C) | 1.0 | Ethylenediamine | 5.0 | None | 78 | 153–154 |
| " | Compound (8) | " | 1.0 | m-Xylyenediamine | 8.16 | " | 74 | 174–179 |
| " | Compound (9) | Compound (D) | 1.0 | Ethylenediamine | 5.0 | " | 70 | 247–251 |
| " | Compound (10) | Compound (E) | 1.0 | " | 5.0 | " | 68 | 135–142 |
| " | Compound (11) | " | 0.6 | 1,4-Cyclohexanediamine | 1.86 | " | 72 | 175–180 |
| " | Compound (12) | Compound (F) | 1.0 | Ethylenediamine | 5.0 | " | 84 | 189–191 |
| " | Compound (13) | Compound (G) | 0.6 | " | 5.0 | " | 78 | 181–183 |

*1): No melting point was visually observed at 450° C. or less

Next, Examples of the use of the diaminourea compound of the present invention for a chain extender will be shown.

Note that the measurement of the physical properties described in the Examples was performed by the following methods:

1) Breaking Strength and Elongation at Break

These were measured by a tensile tester (Orientec Co. UTM-III-100) under conditions of a temperature of 20° C. and a humidity of 65 percent.

A test yarn or 2 mm wide test film was set in the tester gripped at an interval of 50 mm, then was pulled at a deformation speed of 1000 percent/minute until breaking to measure the stress at the break (strength) and the elongation (% with respect to original length). Note that the stress of the test film was corrected to the stress per sectional area. (For the correction of the measurement value after heat treatment of the film, use was made of the value of the sectional area of the film before heat treatment.)

2) Residual Strain and Tension At Recovery

Test pieces were set in the tester in the same way as with measurement of the breaking strength and the elongation at break, the pieces were pulled at a deformation speed of 1000%/minute, the elongation was stopped at 300%, then the pieces were allowed to recover immediately at a recovery speed of 1000%/minute. This was repeated three times, the stresses (tension) at elongations of 100% and 200% at the time of the third recovery were measured, and the residual strain at the time of a tension of 0 was measured. Note that the stress of the test film was corrected to the stress per sectional area. (For the correction of the measurement treatment conditions were an increase in temperature of 2.5° C./minute from an internal temperature of 70° C., holding at 130° C. for three hours, then cooling and reduction of pressure. The test pieces taken out from the dyeing machine were air-dried one day and night in an atmosphere of a temperature of 20° C. and a humidity of 65% and then the physical properties were measured.

4) Heat Set Rate

The strain caused by the heat treatment was measured and the ratio (%) with respect to the length of elongation (40 mm) before the heat treatment was used as the heat setting rate.

$$\text{Heat setting rate (\%)} = \{(I - I_0)/(I_1 - I_0)\} \times 100$$
$$= \{(I - 50)/40\} \times 100$$

$I_0$: length of sample after elongation (90 mm)
$I_1$: length of sample in relaxed state after heat treatment (mm)

5) Strength Retention Rate

The ratio (%) of the breaking strength after heat treatment to the breaking strength before heat treatment was used as the strength retention rate.

Strength retention rate (%)=(Tsa/Tsb)×100
Tsa: breaking strength after heat treatment (g)
Tsb: breaking strength before heat treatment (g)

6) Seconds of Heat Breakage

A 140 mm test portion of a test yarn or 2 mm wide test film was elongated 50% to 210 mm, then was pushed against a 180° C. heating element (approximately 10 mm contact portion) and the number of seconds until breakage was measured.

Example 6

Example of Production of Polyurethaneurea Using Diaminourea Compound Used in Present Invention (N,N'-(Methylenedi-4,1-Phenylene)Bis(2-(Ethylamino)-Urea)) (Hereinafter Referred to as Compound (1))

Four hundred parts by weight of a copolymer diol of tetrahydrofuran and neopentylglycol (hereinafter referred to as NPG) (NPG content of 10 molar%, number average molecular weight of 1780) and 80.8 parts by weight of MDI were caused to react in a nitrogen atmosphere at 70° C. for five hours with agitation to obtain an intermediate polymer having end isocyanate groups. Next, this was cooled to room temperature and dry dimethylacetoamide (hereinafter referred to as DMAc) was added to make a 40 percent by weight concentration intermediate polymer solution.

Next, a DMAc solution including 3.87 parts by weight of diethylamine (hereinafter referred to as DEA) was added and the result was agitated for a while, then the intermediate polymer solution was cooled to −20° C., a DMAc solution containing 26.5 parts by weight of the compound (1) used in the present invention was added to a vigorously agitated intermediate polymer solution, then a 30 percent by weight concentration polyurethaneurea solution was obtained.

Next, 5.1 parts by weight (corresponding to 1% by weight with respect to the polymer solids) of a condensation product of p-cresol and dicyclopentanediene and isobutene of a molecular weight of about 2300 (hereinafter referred to as the stabilizer A) was added as an antioxidant and mixed by agitation to obtain a spinning composition of 30% by weight concentration and a viscosity of 2700 poise/30° C.

This was supplied through an orifice to a dry type spinning machine with a hot air temperature of 270° C. to obtain a yarn of a 40 denier.

DMAc was further added to the 30% by weight concentration spinning composition to make the concentration 20% by weight, then this composition was deaerated and cast on a glass plate using a 0.600 mm applicator. This was dried at 70° C. for 16 hours to obtain a film of a thickness of about 100 μm. The film was cut into 2 mm widths for use as samples for measurement of the physical properties.

Table 3 shows the results of measurement of the physical properties of the obtained fiber.

Comparative Example 1

Example of Use of Conventional, Known Ethylenediamine (Hereinafter Referred to as EDA) Instead of Compound (1) Used in Present Invention The same procedure as in Example 6 was performed except that instead of the 26.5 parts by weight of the compound (1) in Example 6, the same molar amount of EDA, that is, 4.31 parts by weight, was added, whereby a yarn of 40 denier and a film of a thickness of about 100 μm were obtained.

Table 3 shows the results of the measurement of the physical properties of the obtained yarn.

TABLE 3

| | Physical properties of non-treated fiber | | | | | | Physical properties of Treated fiber | | | | | |
|---|---|---|---|---|---|---|---|---|---|---|---|---|
| | Seconds of heat breakage (sec) | Breakage | | Tension | | Residual strain (%) | Breakage strength (g) | Strength retention rate (%) | Tension | | Residual strain (%) | Heat setting rate (%) |
| | | Strength (g) | Elongation (%) | 100% (g) | 200% (g) | | | | 100% (g) | 200% (g) | | |
| Fiber of Example 6 | 1600 | 48 | 630 | 4.5 | 8.5 | 16 | 40 | 87 | 1.5 | 4.4 | 57 | 61 |
| Fiber of Comp. Ex. 1 | 200 | 65 | 610 | 3.1 | 5.5 | 23 | 34 | 52 | 0.7 | 3.2 | 82 | 90 |

1) Tension: Values obtained when fire years each having 40 denier are measured together As will be understood from Table 3, the polyurethaneurea using the diaminourea of the present invention as a chain extender is superior in the seconds of heat breakage, the strength retention rate after heat treatment, the tension, and the heat setting rate compared with the case of use of the conventional, known diamine (EDA).

Examples 7 to 9

Example of Use of Compound (1) Used in Present Invention and Known Diamine Mixed Together In Examples 7 to 9, use was made of a mixture of the compound (1) and the known bifunctional diamine, EDA as a chain extender and polymerization was performed with different ratios of mixture.

That is, instead of the 26.5 parts by weight of the compound (1) in Example 6, mixtures of the same molar amount of the compound (1) and EDA (amounts shown in Table 4) were added. Aside from this, the same procedure was performed as in Example 6, whereby films of thicknesses of about 100 μm were obtained.

Table 4 shows the results of measurement of the physical properties of the resultant films. Table 4 also shows the results of measurement of the physical properties of the films obtained in Example 6 and Comparative Example 1.

TABLE 4

| | Diamine mixing mol ratio Compound (1)/EDA (mol %/mol %) | Diamine amount | | Untreated film properties | | | | |
|---|---|---|---|---|---|---|---|---|
| | | Compound (1) (g) | EDA (g) | Seconds of heat breakage (sec) | Breakage | | Tension | | Residual strain (%) |
| | | | | | Strength kg/cm² | Elongation (%) | 100% kg/cm² | 200% kg/cm² | |
| Example 6 | 100/0 | 26.53 | 0 | 318 | 687 | 979 | 14.7 | 27.3 | 18 |
| Example 7 | 75/25 | 19.90 | 1.08 | 204 | 667 | 983 | 12.2 | 22.1 | 17 |
| Example 8 | 50/50 | 13.27 | 2.16 | 146 | 653 | 995 | 12.9 | 22.8 | 17 |
| Example 9 | 25/75 | 6.63 | 3.23 | 89 | 630 | 973 | 13.5 | 22.5 | 16 |
| Comp. Ex. 1 | 0/100 | 0 | 4.31 | 30 | 612 | 960 | 12.0 | 21.2 | 20 |

TABLE 4-continued

| | Diamine mixing mol ratio Compound (1)/EDA (mol %/mol %) | Diamine amount | | Heat treated film properties | | | | | |
|---|---|---|---|---|---|---|---|---|---|
| | | Compound (1) (g) | EDA (g) | Breakage strength (kg/cm²) | Strength retention rate (%) | Tension 100% kg/cm² | Tension 200% kg/cm² | Residual strain (%) | Heat set ratio (%) |
| Example 6 | 100/0 | 26.53 | 0 | 421 | 61 | 4.6 | 15.4 | 72 | 73 |
| Example 7 | 75/25 | 19.90 | 1.08 | 365 | 55 | 3.6 | 11.7 | 72 | 75 |
| Example 8 | 50/50 | 13.27 | 2.16 | 281 | 43 | 2.3 | 9.2 | 81 | 83 |
| Example 9 | 25/75 | 6.63 | 3.23 | 231 | 37 | 1.5 | 7.8 | 84 | 90 |
| Comp. Ex. 1 | 0/100 | 0 | 4.31 | 158 | 26 | 1.1 | 6.2 | 90 | 95 |

The diaminourea compound used in the present invention, whether used alone or together with a known diamine, results in the major effect of improvement of the heat resistance (seconds of heat breakage, strength retention rate, tension after heat treatment, heat setting rate).

Figure 25:
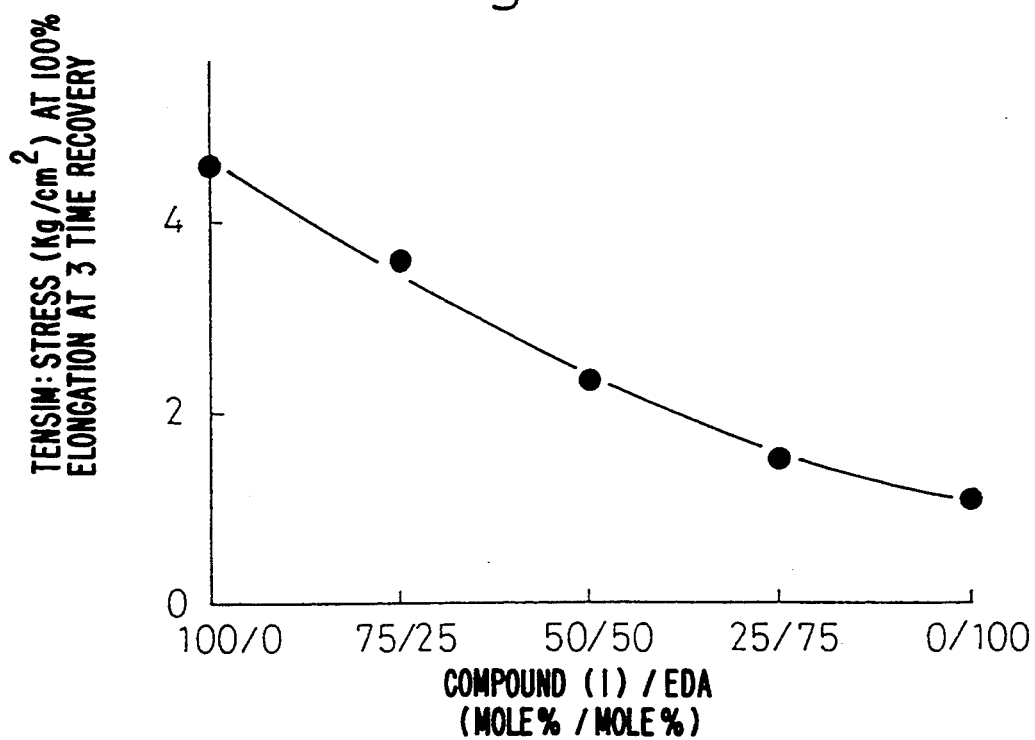
FIG. 25 is a view showing the relationship of the ratio of mixture of the compound (1) and the tension after heat treatment of the film.
Figure 26:
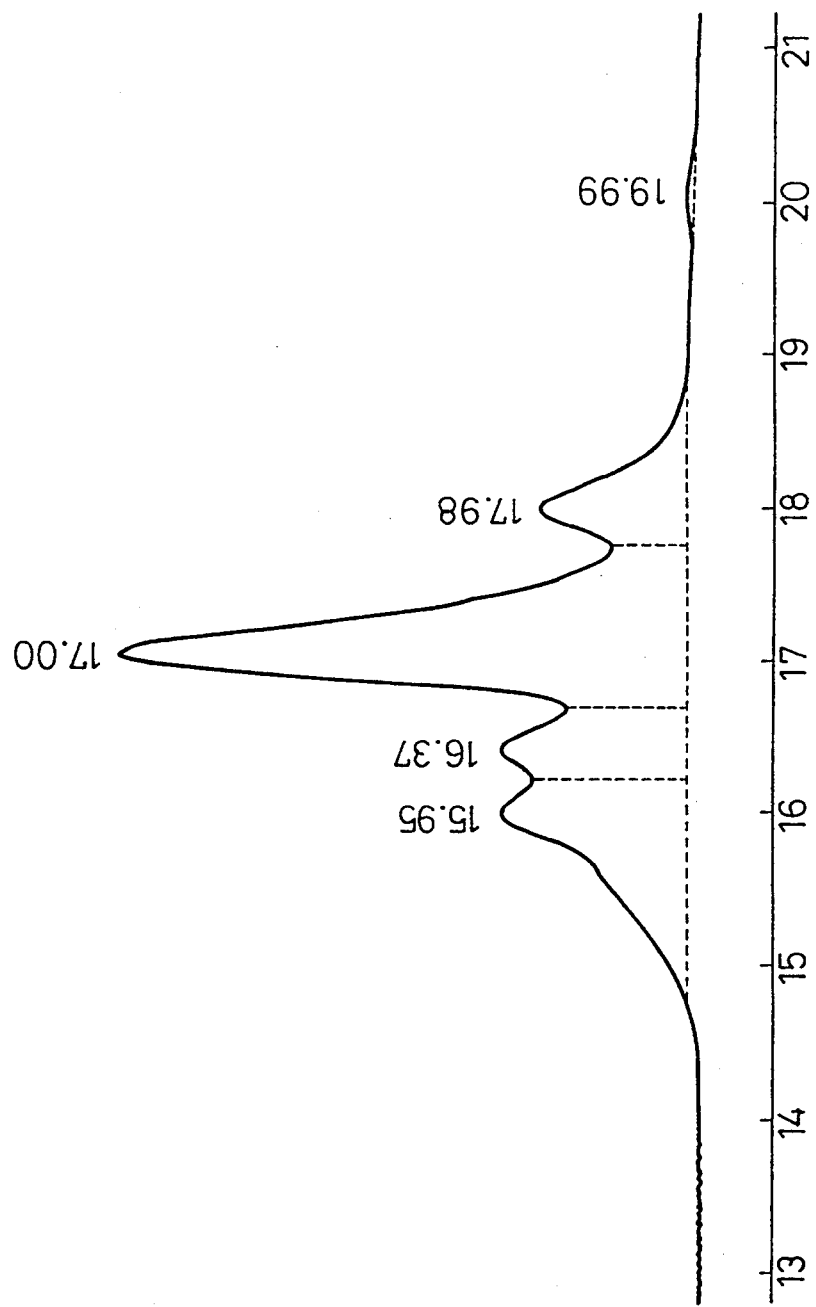
FIG. 26 is a hard segment liquid chromatogram of the polymer synthesized in Example 6.
Figure 27:
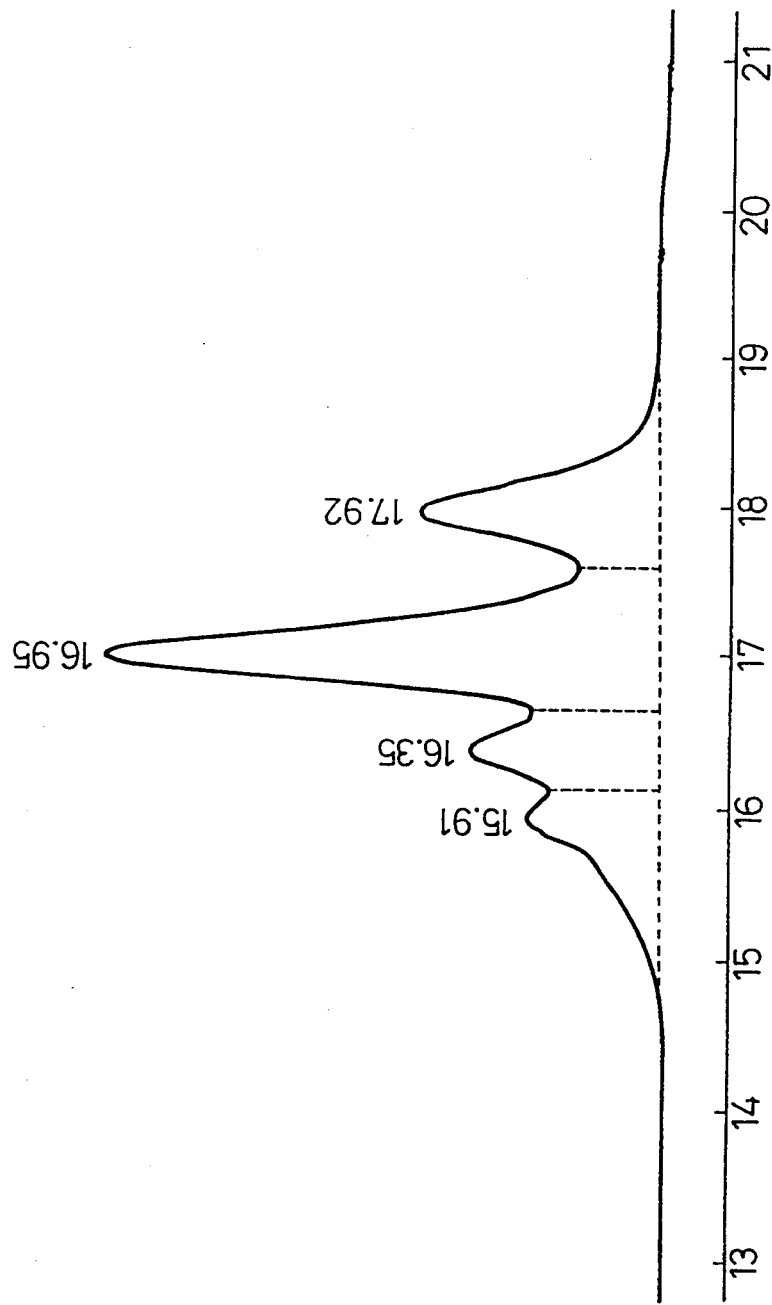
FIG. 27 is a hard segment liquid chromatogram of the polymer synthesized in Example 7.
Figure 28:
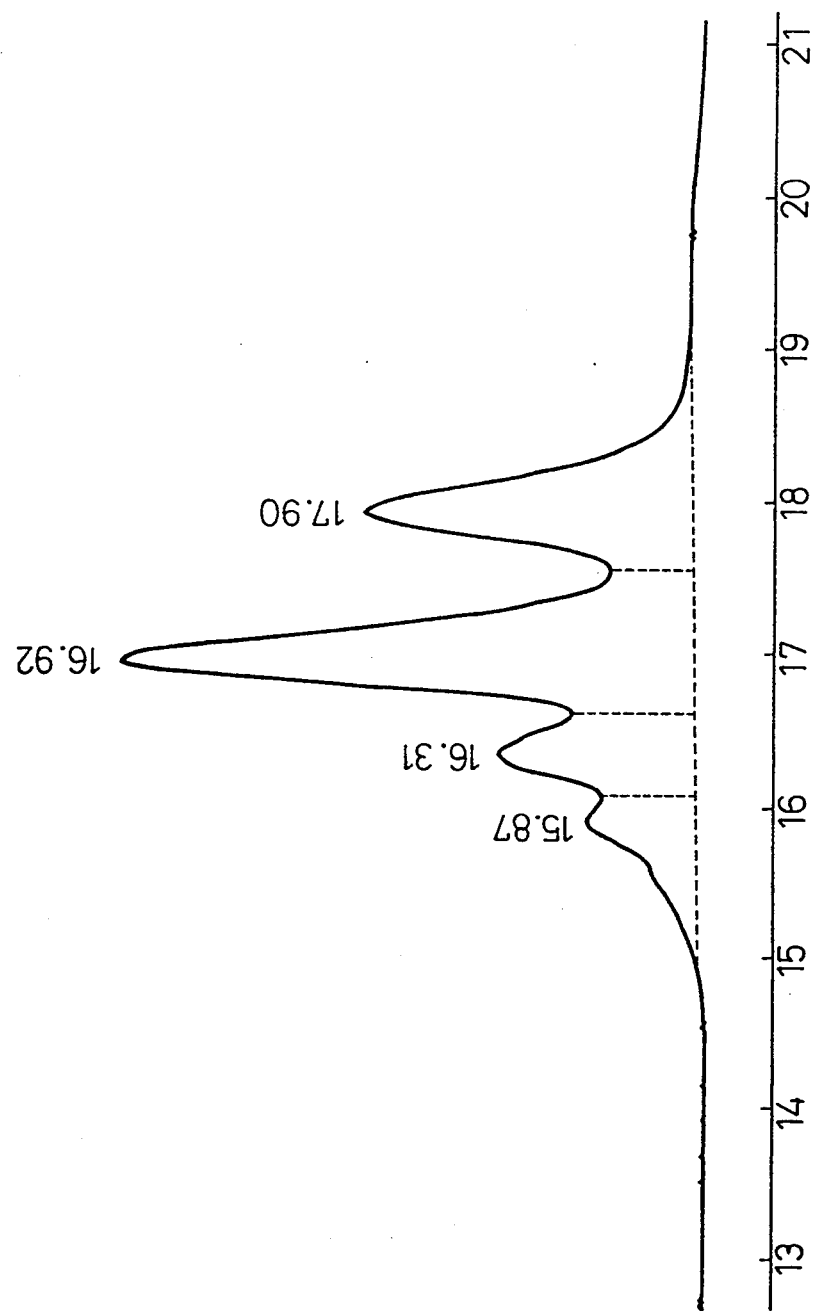
FIG. 28 is a hard segment liquid chromatogram of the polymer synthesized in Example 8.
Figure 29:
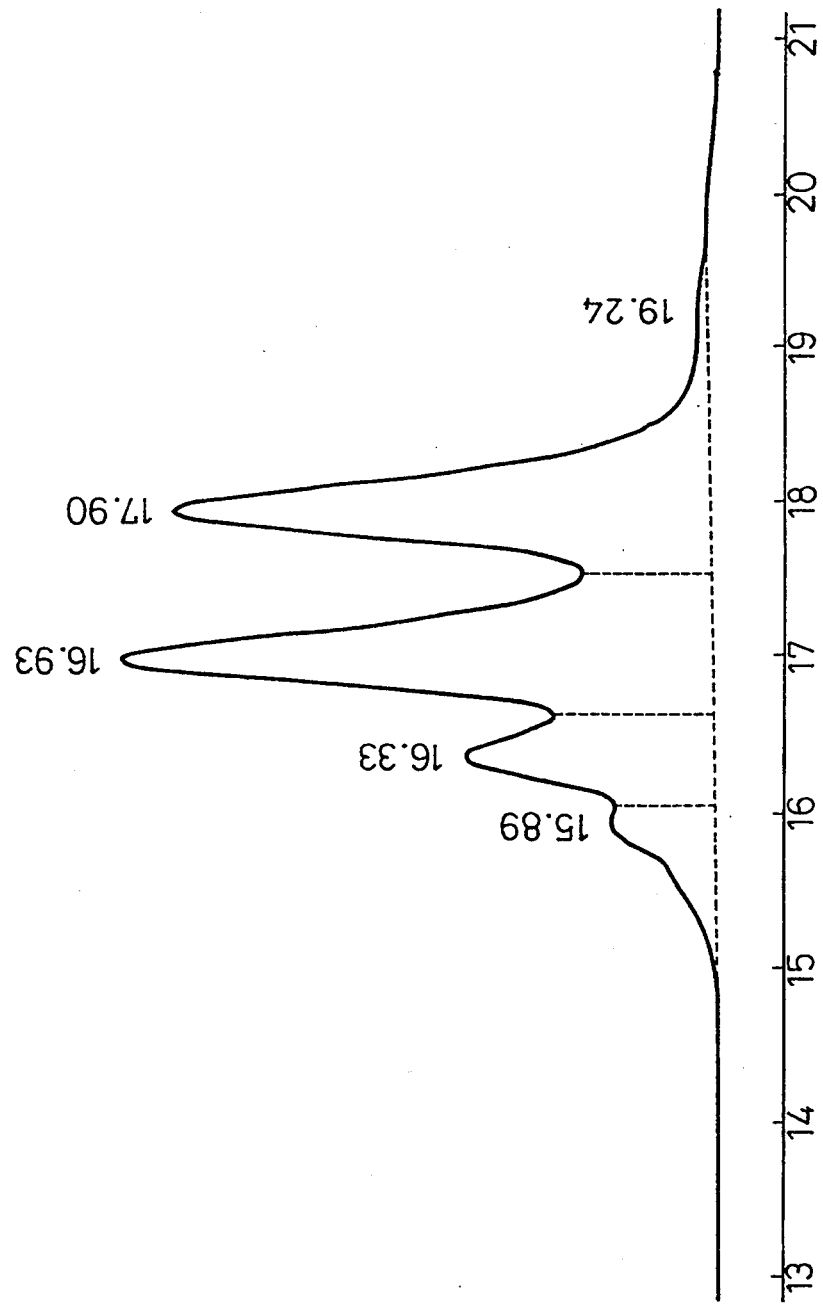
FIG. 29 is a hard segment liquid chromatogram of the polymer synthesized in Example 9.
Figure 30:
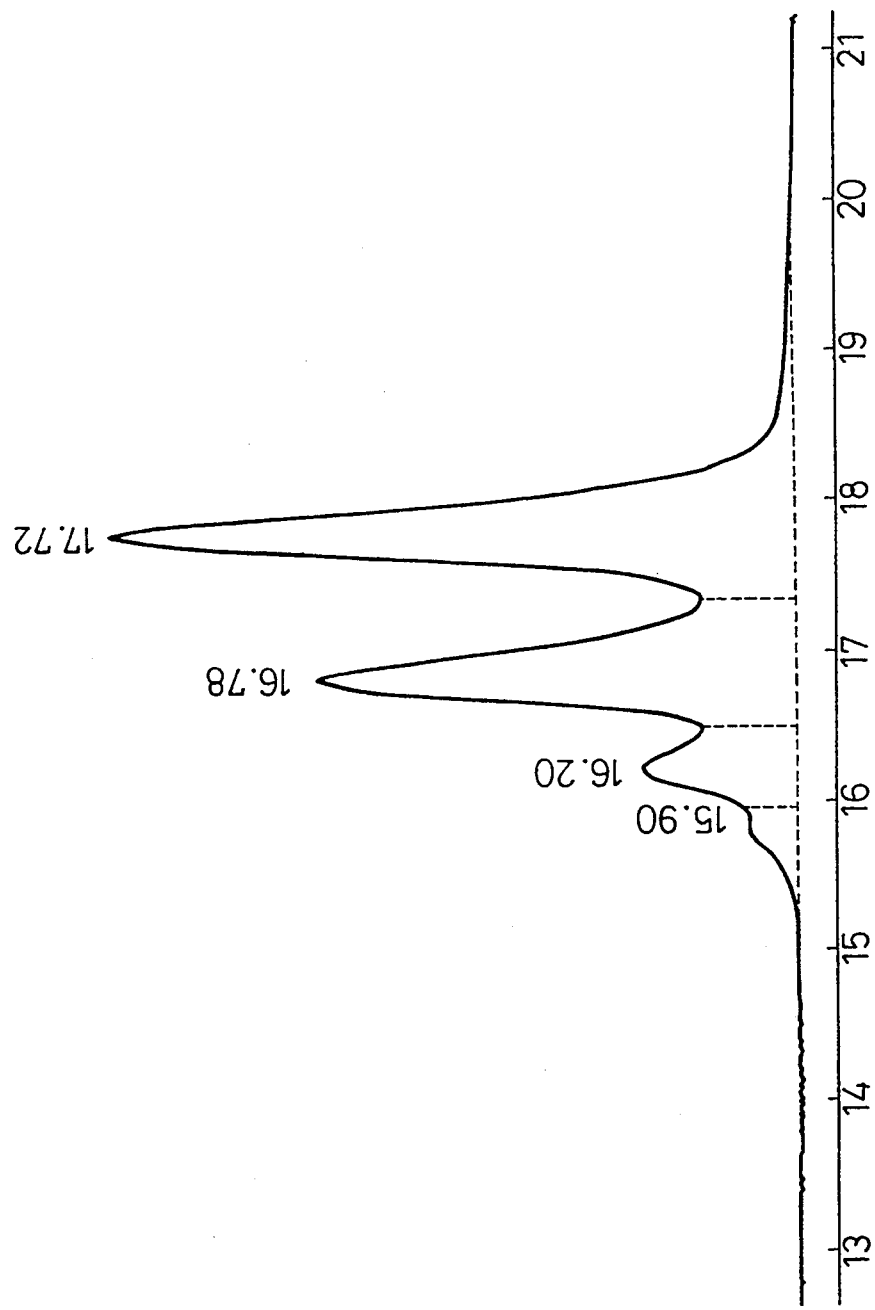
FIG. 30 is a hard segment liquid chromatogram of the polymer synthesized in Comparative Example 1.
Figure 31:
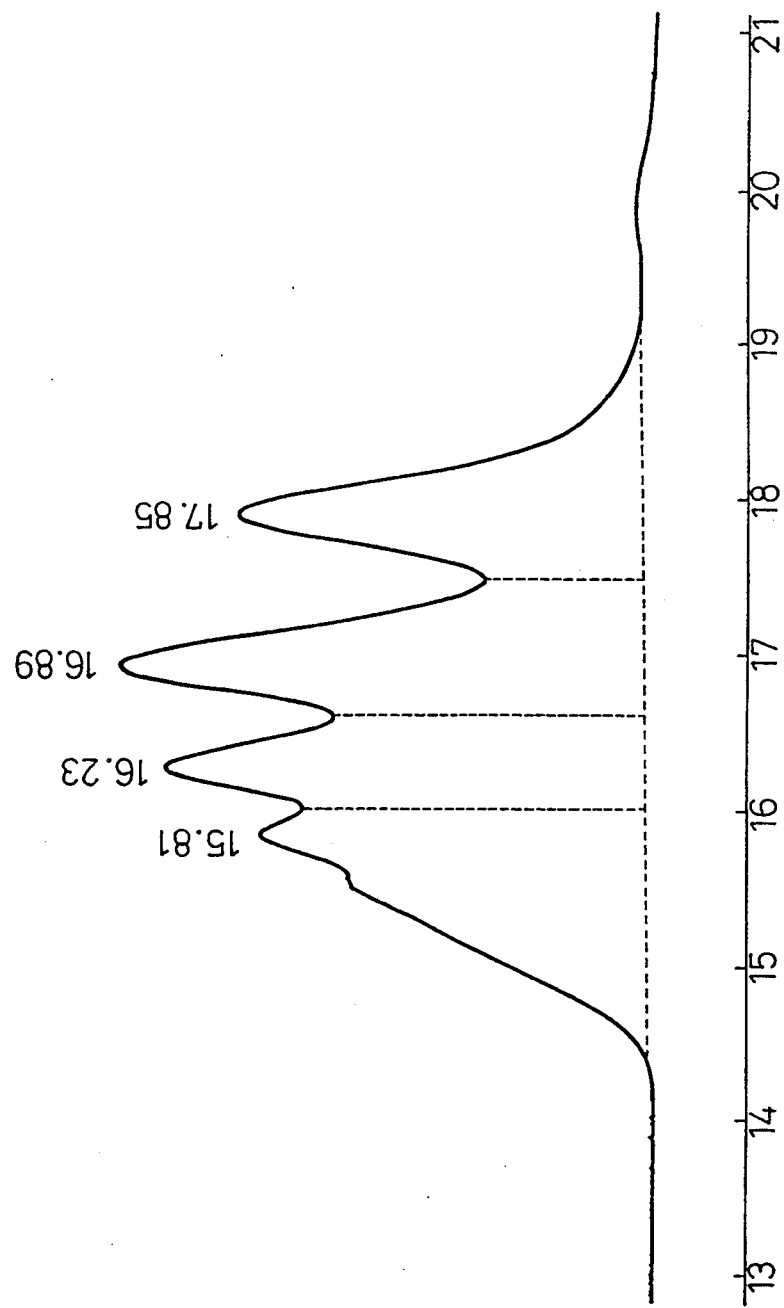
FIG. 31 is a hard segment liquid chromatogram of the polymer synthesized in Comparative Example 2.
Figure 32:
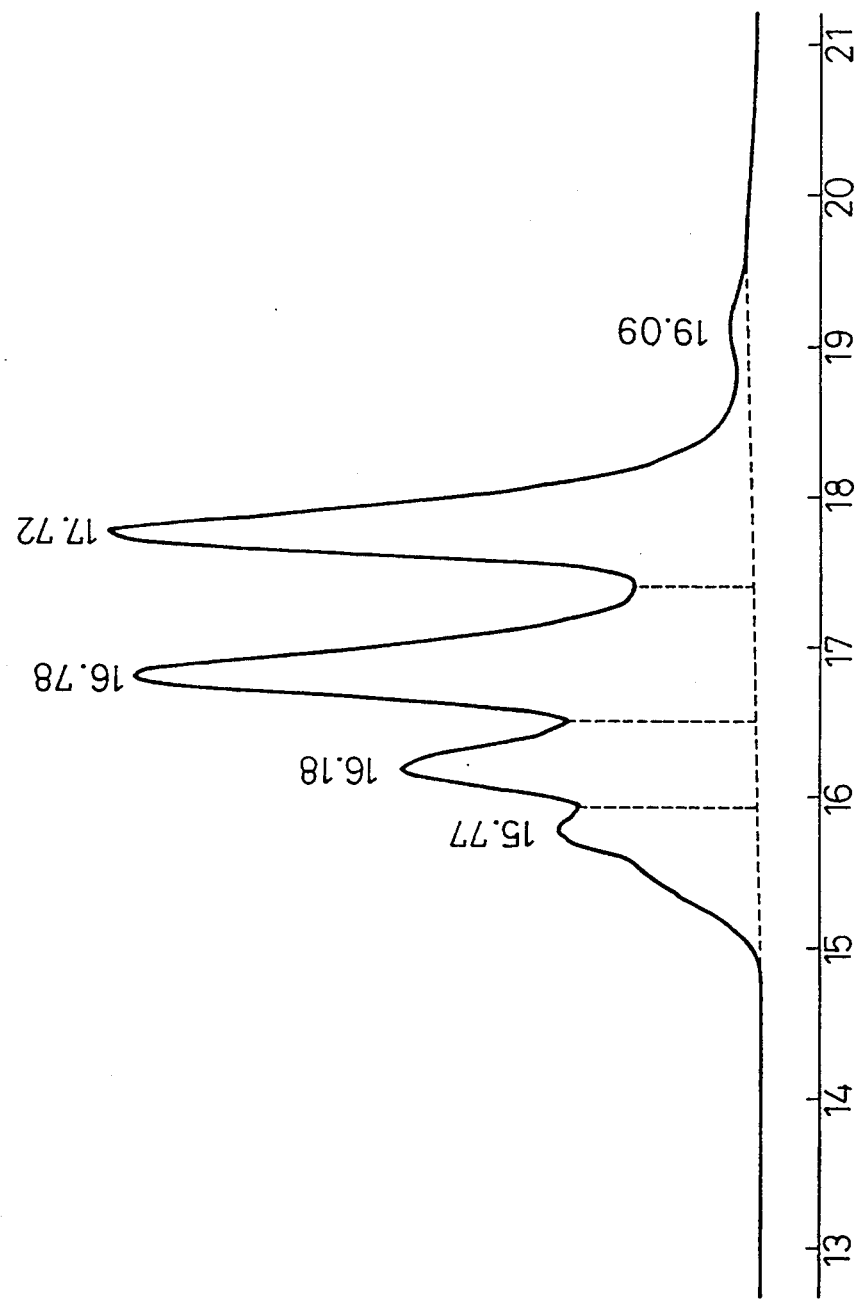
FIG. 32 is a hard segment liquid chromatogram of the polymer synthesized in Comparative Example 3.
Figure 33:
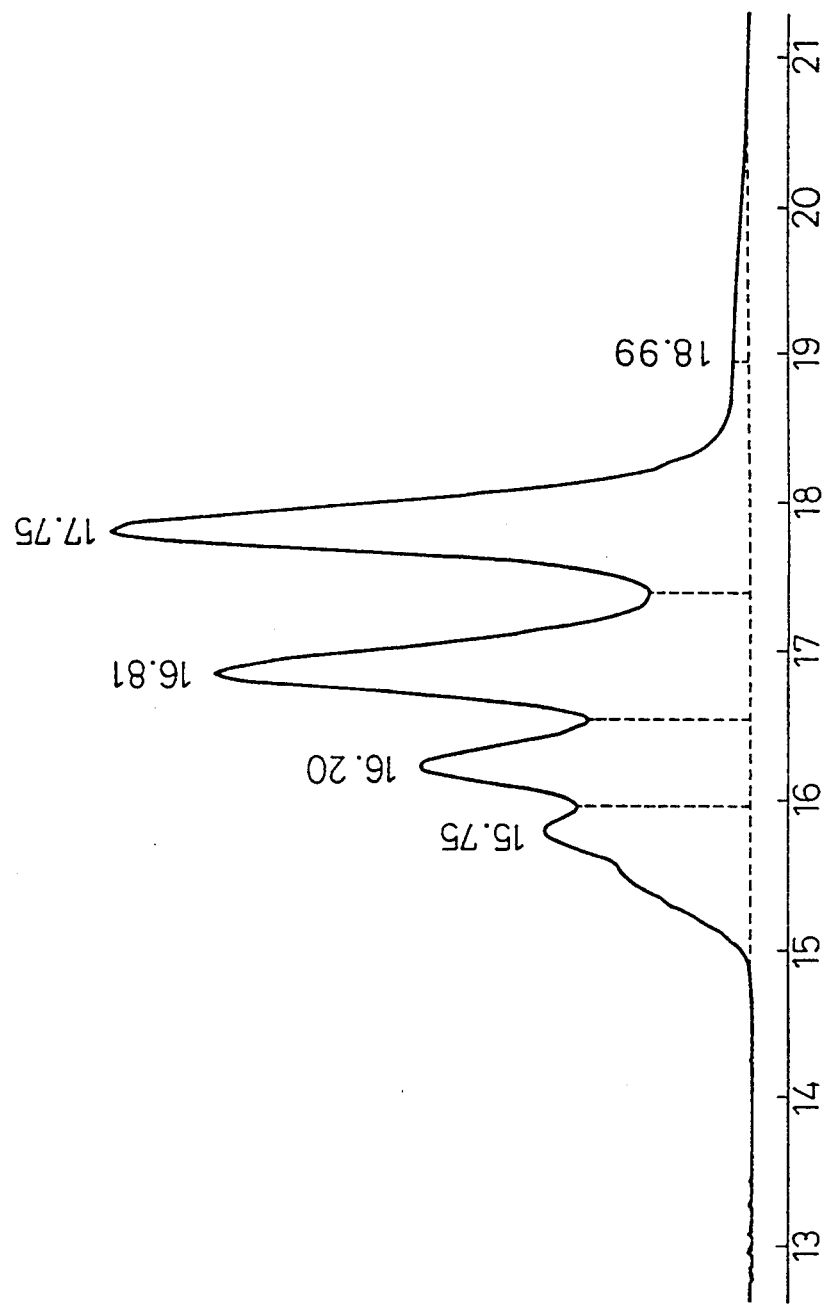
FIG. 33 is a hard segment liquid chromatogram of the polymer synthesized in Comparative Example 4.
Figure 34:
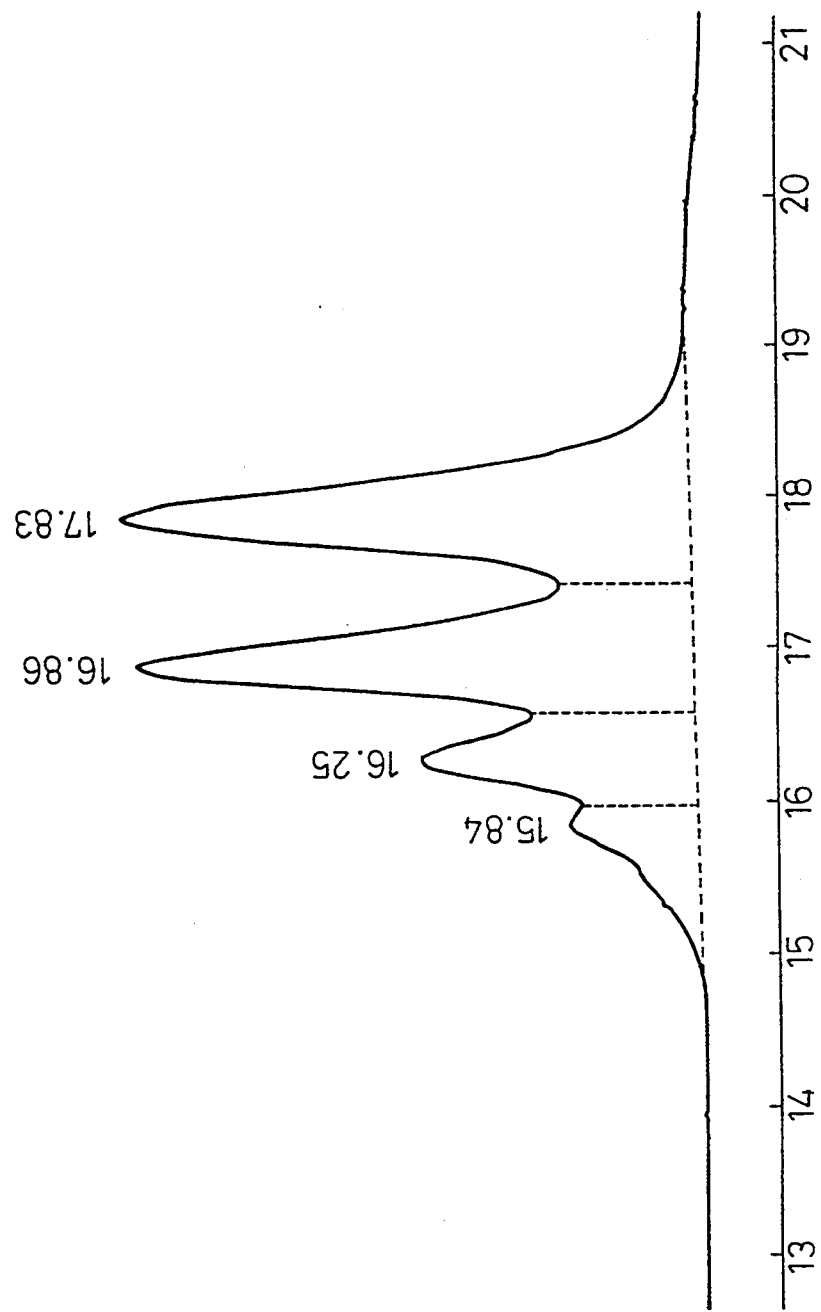
FIG. 34 is a hard segment liquid chromatogram of the polymer synthesized in Comparative Example 5.

FIG. 25 and FIG. 26 are graphs showing the seconds of heat breakage and tension in Table 4. From these graphs, it will be understood that even with a small molar ratio of mixture of the diaminourea compound, an effect is exhibited of improvement of the heat resistance, and with a preferable molar ratio of mixture of at least 10% and more preferably at least 20%, a greater effect is exhibited.

Comparative Examples 2 to 5

Examples of Use of Equal Molar Amounts of MDI and EDA Constituting compound (1) Instead of Compound (1)

Instead of the compound (1) in Examples 6 to 9, MDI and EDA, constituting the compound (1) (the compound (1) being comprised of one molecule of MDI and two molecules of EDA), were added as chain extuder corresponding to the amounts of the compound (1) used in Examples 6 to 9 so as to polymerize the polyurethaneurea.

That is, the amounts of MDI shown in Table 5 were additionally added and dissolved, as additionally added MDI, in 40 percent by weight concentration intermediate polymer solutions obtained by the same method as in Example 6, then DMAc solutions containing 3.87 parts by weight of DEA were added, the results were agitated for a while, then the intermediate polymer solutions were cooled to −20° C. and DMAc solutions including the amounts of EDA shown in Comparative Examples 2 to 5 of Table 5 were added to the vigorously agitated intermediate polymer solutions to obtain 30% by weight concentration polyurethaneurea solutions.

Next, amounts of the stabilizer A corresponding to 1% of the polymer solids were added and the mixtures were mixed with agitation.

These were used to prepare films in the same way as in Example 6, whereupon films of a thickness of about 100 μm were obtained. Table 5 shows the results of measurement of the physical properties of the obtained films are shown in Table 5.

TABLE 5

| | Diamine mixing mol ratio Compound (1)/EDA (mol %/mol %) | Amount of MDI additionally added to intermediate polymer solution (g) | Diamine amount | | Non-treated film Seconds of heat breakage (sec) | Heat treated film properties | | | | |
|---|---|---|---|---|---|---|---|---|---|---|
| | | | Compound (1) (g) | EDA (g) | | Breakage Strength kg/cm² | Strength retention rate % | Tension 100% kg/cm² | Tension 200% kg/cm² | Residual strain (%) |
| Example 6 | 100/0 | 0 | 26.53 | 0 | 318 | 421 | 61 | 4.6 | 15.4 | 72 |
| Comp. Ex. 2 | 0/100 | 17.94 | 0 | 8.59 | 70 | 210 | 33 | 1.8 | 9.6 | 86 |
| Example 7 | 75/25 | 0 | 19.90 | 1.08 | 204 | 365 | 55 | 3.6 | 11.7 | 72 |
| Comp. Ex. 3 | 0/100 | 13.46 | 0 | 7.52 | 43 | 204 | 32 | 1.7 | 8.2 | 85 |
| Example 8 | 50/50 | 0 | 13.27 | 2.16 | 146 | 281 | 43 | 2.3 | 9.4 | 81 |
| Comp. Ex. 4 | 0/100 | 8.97 | 0 | 6.46 | 48 | 199 | 34 | 1.5 | 8.1 | 87 |
| Example 9 | 25/75 | 0 | 6.63 | 3.23 | 89 | 231 | 37 | 1.5 | 7.8 | 84 |
| Comp. Ex. 5 | 0/100 | 4.49 | 0 | 5.37 | 35 | 189 | 34 | 1.3 | 7.4 | 87 |

From the viewpoint that one mole of the compound (1) corresponds to one mole of MDI and two moles of EDA, Comparative Examples 2 to 4 comprised amounts of MDI and EDA corresponding to the amounts of the compound (1) added in Examples 6 to 9. Further, Comparative Example 2 corresponded to Example 6, Comparative Example 3 to Example 7, Comparative Example 4 to Example 8, and Comparative Example 5 to Example 9. Comparing use of the compound (1) and use of MDI and EDA, the use of the diaminourea compound used in the present invention clearly improves the heat resistance (seconds of heat breakage, strength retention rate, tension after heat treatment).

Example 10

Example of Use of Polytetramethyleneglycol (Hereinafter Referred to as PTMG) for Polymer Diol Four hundred parts by weight of PTMG of a number average molecular weight of 1830 and 74.9 parts by weight of MDI were caused to react in a nitrogen gas atmosphere at 70° C. for 5 hours, with agitation, to obtain an intermediate polymer having end isocyanate groups. Next, the intermediate polymer was cooled to 10° C., then dry DMAc was added, to make an intermediate polymer solution of a concentration of 40% by weight.

Next, a DMAc solution containing 55.8 parts by weight of the compound (1) and 0.83 part by weight of DEA was added into a vigorously agitated intermediate polymer solution to obtain a polyurethaneurea solution of a concentration of 30% by weight and a viscosity of 3800 poise/30° C.

After the polymerization, the solution was diluted to a concentration of 20 percent, 5.3 parts by weight of the stabilizer A was added and agitated, then a film was prepared by the same procedure as in Example 6 to obtain film of a thickness of about 100 μm. Table 6 shows the results of the measurement of the physical properties of the resultant film.

Comparative Example 6

Example of Use of Equal Molar Amount of EDA Instead of Compound (1) Used in Present Invention in Example 10

The same procedure was performed as in Example 10 to obtain a film of a thickness of about 100 μm, except that instead of the 55.8 parts by weight of the compound (1) in Example 10, 9.06 parts by weight of EDA was added. The results of the measurement of the physical properties of the resultant film are shown in Table 6.

stock solution of a concentration of 30%. The viscosity of the stock solution at 30° C. was 4000 poise.

DMAc was immediately added to the stock solution to make the concentration 20%, then the stabilizer A was added in an amount of 1.24 g (1 percent with respect to polymer solids) as an antioxidant. A film was cast from this 20% stock solution using a 0.600 mm applicator, then was dried at 70° C. for 16 hours, to obtain a film of a thickness of about 100 μm.

Example 13

Example of Polymerization of High Heat Resistance Polyurethane

An 18.7 g amount of MDI and 100 g of PTMG (molecular weight of 1830) were caused to react in a separable flask in a nitrogen atmosphere at 70° C. for five hours, with agitation, to synthesize the prepolymer. After this, this was returned to room temperature and 178 g of DMAc was added to dissolve the same. Next, 6.41 g of the compound (1) and 0.28 g of DEA dissolved

TABLE 6

| | Untreated film properties | | | | | Heat treated film properties | | | | | |
|---|---|---|---|---|---|---|---|---|---|---|---|
| | Seconds of heat breakage (sec) | Breakage | | Tension | | Residual strain (%) | Breakage strength kg/cm² | Strength retention rate (%) | Tension | | Residual strain (%) | Heat set rate (%) |
| | | Strength kg/cm² | Elongation (%) | 100% kg/cm² | 200% kg/cm² | | | | 100% kg/cm² | 200% kg/cm² | | |
| Example 10 | 309 | 900 | 820 | 17.3 | 28.4 | 27 | 460 | 51 | 7.4 | 19.7 | 65 | 73 |
| Comp. Ex. 6 | 173 | 892 | 791 | 14.9 | 24.7 | 30 | 205 | 23 | 4.6 | 14.1 | 74 | 87 |

By using the diaminourea compound used in the present invention as a chain extender, it is possible to tremendously improve the heat resistance of the polyurethaneurea.

Examples 11 and 12

Examples of Use of Diaminourea Compounds Used in Present Invention (N,N'-(Methylenedi-4,1-Phenylene)-Bis(2-(2-Methylethylamino]-Urea) (Hereinafter Referred to as Compound (2)) and N,N'-(Methylenedi-4,1-Phenylene)Bis(6-(Hexylamino)-Urea) (Hereinafter Referred to as Compound (3))

Instead of the compound (1) in Example 6, the polymerizations were performed using the compound (2) in Example 11 and the compound (3) in Example 12. Otherwise, the same procedures were performed as in Example 6 to obtain films of a thickness of about 100 μm. The films were subjected to heat treatment and measured as to their physical properties in the same way as with the previous example, as a result of which the polyurethaneurea using the compound (2) or the compound (3) was found to show a superior heat resistance, in terms of the seconds of heat breakage, strength retention rate, and tension after heat treatment, to the polyurethaneurea using the conventional, known diamine EDA.

Comparative Example 7

Example of Polymerization of Polyurethane

An 18.7 g amount of MDI and 100 g of PTMG (molecular weight of 1830) were caused to react in a separable flask in a nitrogen atmosphere at 70° C. for five hours, with agitation, to synthesize the prepolymer. After this, this was returned to room temperature and 178 g of N,N-dimethylacetoamide (hereinafter referred to as DMAc) was added to dissolve the same. Next, 1.04 g of EDA and 0.28 g of DEA dissolved in 102 g of DMAc were quickly added to the vigorously agitated prepolymer for the polymerization to obtain a polymer in 102 g of DMAc were quickly added to the vigorously agitated prepolymer for the polymerization, thereby obtaining a polymer of a concentration of 30%. The viscosity of the stock solution at 30° C. was 3600 poise.

In the same way as Comparative Example 7, the stock solution was made 20% in concentration and 1.25 g of the stabilizer A, corresponding to 1% of the polymer solids, was added to prepare a film.

The films obtained in Comparative Example 7 and Example 13 were cut into 2 mm widths and used as samples for the heat resistance test. The heat resistance test was performed by evaluation of the seconds of heat breakage. The results are shown in Table 7.

Seconds of heat breakage: The time when the sample was pressed against a heating element of 180° C.* under an elongation of 50% until it broke was measured.

TABLE 7

| Sample | Seconds to heat breakage |
|---|---|
| High heat resistance polyurethane film of Example 13 | 383 seconds |
| Polyurethane film of Comparative Example 7 | 85 seconds |

Next, Examples will be shown of the case of use of the diaminourea compound of the present invention as a high molecular weight imparting additive.

Note that the measurement of the physical properties described in the Examples was performed by the following methods:

1) Ultimate Filament Denier

The stringiness of the spinning composition during spinning was evaluated by the ultimate filament denier. The ultimate filament denier was found in the following way. During dry spinning, a 40 denier/4 filament yarn was taken up once. The speed was fixed to 600 m/min for three minutes, then the takeup speed was gradually raised. When the takeup speed at the point when yarn breakage occurred in the spinning chimney was designated as X m/min, the ultimate filament denier per filament can be calculated by the following equation:

Ultimate filament denier = (40/4) × (600/X)

where, X is the takeup speed at the time of yarn breakage (m/min) The smaller the ultimate filament denier, the better the stringiness of the spinning composition.

2) Knot Strength

This was measured by a tensile tester (Orientec Co., UTM-III-100) under conditions of a temperature of 20° C. and a humidity of 65%.

A knot was made in the center of gripped portion of the sample gripped at an interval of 50 mm. This was pulled at a deformation speed of 1000%/minute until breaking to measure the stress (strength) at break. Note that the measured value was the average obtained by measuring test yarns knotted in the right direction and test yarns knotted in the left direction the same number of times (n=5 for each) and confirming the breakage at the knotted portions.

3) Breaking Strength, Elongation at Break, Residual Strain, Tension at Recovery

These were measured in the same ways as the previously explained methods.

4) Heat Setting Rate

A test yarn or 2 mm wide test film gripped at a 50 mm interval was elongated 80% to 90 mm, then immersed in boiling water for one hour, then was dry heat set as is at 80% elongation at 120° C. for one minute. The strain caused by the heat setting was measured and the ratio with respect to the length (40 mm) elongated before the heat treatment was used as the heat setting rate.

$$\text{Heat setting rate (\%)} = \{(I - I_0)/(I_1 - I_0)\} \times 100$$
$$= \{(I - 50)/40\} \times 100$$

where,
$I_0$: length of sample (50 mm)
$I_1$: length of sample after elongation (90 mm)
$I$: length of sample in relaxed state after heat treatment (mm)

5) Reduced Viscosity ($\eta sp/C$)

The reduced viscosity was measured as a way to evaluate the polymer molecular weight. That is, a test film was dissolved in DMAc at a concentration of 0.005 g/ml and the flow time of the solvent and the solution was measured by an Ostwald viscometer in a 25° C. constant temperature water tank. The reduced viscosity was found by the following equation:

$$(\eta sp/C) = \{(t - t_0)/t_0\} \cdot 1/C$$

where,
t: flow speed of solution (seconds)
$t_0$: flow speed of solvent (seconds)
C: concentration of polymer (g/ml)

Example 14

A 400 part by weight amount of PTMG of a number average molecular weight of 1830 and 87 parts by weight of MDI were caused to react in a nitrogen gas atmosphere at 70° C. for three hours with agitation to obtain an intermediate polymer having end isocyanate groups. Next, this was cooled to room temperature and dry DMAc was added to make an intermediate polymer solution of a concentration of 40% by weight.

Next, a DMAc solution including 7.28 parts by weight of EDA and 1.11 parts by weight of DEA was added to the vigorously agitated intermediate polymer solution to obtain a polyurethaneurea solution of a concentration of 30% by weight.

Next, 5.0 parts by weight (corresponding to 1% by weight of the polymer solids) of the stabilizer A was added as an antioxidant and agitated and mixed with the solution.

Further, a DMAc solution containing 2.81 parts by weight (A/B=0.5) of the compound (1), that is, the diaminourea compound used in the present invention, was added, mixed, and deaerated to obtain a spinning composition of a concentration of 30% by weight and a viscosity of 3400 poise/30° C. (In the text, A indicates the molar amount of diaminourea compound added, and B indicates the molar amount of the monofunctional amine used for the production of the polyurethaneurea polymer).

This was supplied through an orifice to a dry spinning machine with a hot air temperature held at 270° C. to obtain a yarn of 40 denier.

DMAc was added to the 30% by weight concentration spinning composition to make it 20% by weight in concentration. This composition was cast on a glass plate using a 0.600 mm applicator and was dried at 70° C. for 16 hours to obtain a film of a thickness of approximately 100 μm. The film was cut into 2 mm widths which were used as samples for measurement of the physical properties.

Table 8 shows the results of the measurement of the physical properties of the obtained yarn. Table 9 shows the results of the measurement of the physical properties of the film.

Examples 15 and 16

The same procedure was followed as in Example 14 except that instead of the 2.81 parts by weight of the compound (1) in Example 14, 3.02 parts by weight of the compound (2) (A/B=0.5) was added in Example 15 and 3.66 parts by weight of the compound (3) (A/B=0.5) was added in Example 16, whereby yarns of 40 denier and films having a thickness of about 100 μm were obtained. Table 8 shows the results of the measurement of the physical properties of the obtained yarn. Table 9 shows the results of the measurement of the physical properties of the film.

Comparative Example 8

Known Art: Example of Japanese Unexamined Patent Publication (Kokai) No. 59-129257

The same procedure was followed as in Example 14 except that instead of the 2.81 parts by weight of the compound (1) in Example 14, 3.01 g of the known compound expressed by the formula (VIII) was added, whereby a yarn of 40 denier and film having a thickness of about 100 μm were obtained. Table 8 shows the results of the measurement of the physical properties of the obtained yarn. Table 9 shows the results of the measurement of the physical properties of the film.

Comparative Example 9

Known Art: Example of Japanese Unexamined Patent Publication (Kokai) No. 1-170648

A DMAc solution containing 8.13 parts by weight of EDA and 0.93 part by weight of DEA was added under vigorous agitation to an intermediate polymer solution of a concentration of 40% by weight obtained in the same way as Example 14, whereby a polyurethaneurea solution of a concentration of 30% by weight, including free amino groups in the polymer ends, was obtained.

Next, 5.0 parts by weight of the stabilizer A was added and mixed with agitation.

Further, a DMAc solution including 2.52 parts by weight of the known compound expressed by chemical formula (VIII) was added and mixed with agitation, then was deaerated to obtain a spinning composition of a concentration of 30% by weight.

This was used for spinning and film-making in the same way as in Example 14 to obtain a yarn of 40 denier and a film of a thickness of about 100 μm. Table 8 shows the results of the measurement of the physical properties of the obtained yarn. Table 9 shows the results of the measurement of the physical properties of the film.

Comparative Example 10

Example of No Addition of Diaminourea Compound of Present Invention

A spinning composition of a concentration of 30% by weight obtained in the same way as in Example 14 except without the addition of the compound (1), that is, the diaminourea compound, was used in the same way as in Example 14 for spinning and film-making to obtain a yarn of 40 denier and a film of a thickness of about 100 μm. Table 8 shows the results of the measurement of the physical properties of the obtained yarn. Table 9 shows the results of the measurement of the physical properties of the film.

molecular weight of 2074) of tetrahydrofuran and NPG and 83 parts by weight of MDI were caused to react in a nitrogen gas atmosphere at 70° C. for five hours with agitation to obtain an intermediate polymer having end isocyanate groups. Next, this was cooled to room temperature and dry DMAc was added to make an intermediate polymer solution of a concentration of 40% by weight.

Next, a DMAc solution containing 7.91 parts by weight of EDA and 1.01 parts by weight of DEA was added to the vigorously agitated intermediate polymer solution to obtain a polyurethaneurea solution of a concentration of 30 percent by weight.

Next, 4.9 parts by weight of the stabilizer A was added and mixed with agitation.

Further, a DMAc solution containing 2.55 parts by weight (A/B=0.5) of the compound (1), that is, the diaminourea compound used in the present invention, was added, mixed, and deaerated to obtain a spinning composition of a concentration of 30% by weight and a viscosity of 3700 poise/30° C.

This was used for spinning in the same way as with Example 14 to obtain a yarn of 40 denier. Table 10 shows the results of the measurement of the physical properties of the obtained yarn.

Comparative Example 11

Known Art: Example of Addition of Known Aromatic Diurea Compound Similar to Compound of Present Invention The same procedure was followed as with Example 17 except that instead of the 2.55 parts by weight of the

TABLE 8

|  |  | Ultimate filament denier d | Knot strength g | Breakage | | Tension | | Residual strain % | Heat set rate % |
|---|---|---|---|---|---|---|---|---|---|
|  |  |  |  | Strength g | Elongation % | 100% g | 200% g |  |  |
| Present Invention | Fiber of Example 14 Diaminourea compd. (1) | 1.7 | 59.6 | 75.2 | 653 | 0.91 | 1.44 | 14 | 34 |
|  | Fiber of Example 15 Diaminourea compd. (2) | 1.8 | 58.3 | 73.6 | 644 | 0.88 | 1.41 | 16 | 36 |
|  | Fiber of Example 16 Diaminourea compd. (3) | 1.8 | 51.4 | 74.4 | 643 | 0.83 | 1.40 | 18 | 39 |
| Comparative Example | Fiber of Comp. Ex. 8 Ex. of JP-A-59-129257 | 3.5 | 39.9 | 68.5 | 639 | 0.77 | 1.25 | 26 | 44 |
|  | Fiber of Comp. Ex. 9 Ex. of JP-A-1-170648 | 2.7 | 41.2 | 70.8 | 640 | 0.75 | 1.26 | 25 | 42 |
|  | Fiber of Comp. Ex. 10 Ex. of no addition of diaminourea compd. | 2.0 | 49.3 | 69.3 | 641 | 0.73 | 1.24 | 27 | 48 |

TABLE 9

|  |  | Reduced viscosity ηsp/c | Breakage | | Tension | | Residual strain % | Heat set rate % |
|---|---|---|---|---|---|---|---|---|
|  |  |  | Strength kg/cm² | Elongation % | 100% kg/cm² | 200% kg/cm² |  |  |
| Present Invention | Film of Example 14 | 2.81 | 721 | 756 | 17.0 | 31.1 | 26 | 40 |
|  | Film of Example 15 | 2.38 | 718 | 741 | 16.3 | 29.4 | 28 | 44 |
|  | Film of Example 16 | 2.36 | 718 | 740 | 16.2 | 29.3 | 28 | 44 |
| Comparative Example | Film of Comp. Ex. 8 | 1.51 | 703 | 729 | 15.0 | 24.0 | 30 | 51 |
|  | Film of Comp. Ex. 9 | 1.63 | 715 | 738 | 15.2 | 25.6 | 29 | 49 |
|  | Film of Comp. Ex. 10 | 1.32 | 709 | 731 | 14.4 | 23.0 | 31 | 56 |

As will be understood from Tables 8 and 9, the yarn and film obtained by the present invention are tremendously improved in stringiness, knot strength, elastic characteristics, and heat resistance compared with the known art.

Example 17

A 400 part by weight amount of a copolymer diol (NPG content of 12 molar percent and number average compound (1) of the present invention in Example 17, 2.74 g of the known compound expressed by chemical formula (VIII) was added. Table 10 shows the results of the measurement of the physical properties of the obtained yarn.

Comparative Example 12

Example of NO Addition of Diaminourea Compound

The same procedure as in Example 17 was performed except without the addition of the compound (1), that is, the diaminourea compound, to obtain a spinning composition of a concentration of 30% by weight. This was used for spinning in the same way as in Example 14 to obtain a yarn of 40 denier.

The results of measurement of the physical properties of the obtained yarn are shown in Table 10.

| Apparatus: | Shimadzu LC-6A |
|---|---|
| Solution: | DMSO (LiCl 0.02M)/Liquid chromatography tetrahydrofuran 3:4 |
| Flow rate: | 0.6 ml/min |
| Column: | YMC AM-313 (ODS) × 3 |
| Column temperature: | 50° C. |
| UV measurement wavelength: | 290 nm |

TABLE 10

| | Ultimate filament denier d | Knot strength g | Breakage Strength g | Breakage Elongation % | Tension 100% g | Tension 200% g | Residual strain % | Heat set rate % |
|---|---|---|---|---|---|---|---|---|
| Fiber of Example 17 | 1.7 | 65.0 | 73.5 | 665 | 1.01 | 1.99 | 15 | 33 |
| Fiber of Comp. Ex. 11 | 3.7 | 47.5 | 69.9 | 640 | 0.81 | 1.68 | 19 | 39 |
| Fiber of Comp. Ex. 12 | 1.8 | 58.6 | 68.5 | 662 | 0.77 | 1.55 | 19 | 41 |

In this way, the present invention is sufficiently effective even when use is made of a copolymer diol of tetrahydrofuran and NPG as the material for the polyurethaneurea polymer.

Examples 18 to 22

5.0 part by weight amounts of the stabilizer A were added to 30 percent by weight concentration polyurethaneurea solutions obtained by the same method as in Example 14 and were mixed with agitation. Further, the amounts of the compound (1) shown in Table 11 were added, mixed in, and deaerated. The same procedure was performed as in Example 14 to obtain films having a thickness of about 100 μm. The results of the measurement of the physical properties of the films are shown in Table 11.

TABLE 11

| | | A/B | Reduced viscosity ηsp/c | Breakage Strength kg/cm² | Breakage Elongation % | Tension 100% kg/cm² | Tension 200% kg/cm² | Residual strain % | Heat set rate % |
|---|---|---|---|---|---|---|---|---|---|
| Present Method | Film of Example 18 | 0.005 | 1.93 | 717 | 740 | 16.1 | 27.2 | 28 | 46 |
| | Film of Example 19 | 0.05 | 2.15 | 718 | 750 | 16.4 | 28.6 | 27 | 43 |
| | Film of Example 20 | 0.5 | 2.81 | 721 | 756 | 17.0 | 31.1 | 26 | 40 |
| | Film of Example 21 | 2.0 | 1.82 | 718 | 740 | 16.3 | 28.1 | 27 | 44 |
| | Film of Example 22 | 3.0 | 1.80 | 717 | 740 | 16.3 | 28.0 | 29 | 46 |
| Comparative Example | Film of Comp. Ex. 8 | — | 1.51 | 703 | 729 | 15.0 | 24.0 | 30 | 51 |
| | Film of Comp. Ex. 9 | — | 1.65 | 715 | 738 | 15.2 | 25.6 | 29 | 49 |
| | Film of Comp. Ex. 10 | — | 1.32 | 709 | 731 | 14.4 | 23.0 | 31 | 56 |

In the formula, A indicates the molar amount of compound (1) added, and B indicates the molar amount of the monofunctional amine used for the production of the polyurethaneurea polymer which is added and mixed in.

As will be understood from Table 11, the desired effect is seen if the amount of the diaminourea compound added in the present invention is $0.005 \leq A/B \leq 3.0$, where the molar amount added is A moles and the molar amount of the monofunctional amine used in the production of the polyurethaneurea polymer added and mixed in is B moles.

Next, examples will be shown of the analysis of the distribution of the molecular weight of the hard segments of the polyurethaneurea using the diaminourea compound of the present invention as a chain extender.

Note that the measurement of the liquid chromatography described in the Examples was performed under the following conditions:

Example 23

A 30 g amount of DMAc was added to 5 g of polyurethaneurea solution of a concentration of 30% by weight obtained in Example 6. This was agitated and 90 g of methanol was added dropwise. The precipitate was filtered by a glass filter (3G4) and was washed on the filter by methanol. To remove the DMAc in the obtained solids, the solids were immersed a day and night in 150 g of methanol, then were filtered by a glass filter (3G4), washed with methanol, and vacuum dried at 80° C. for two hours, to obtain about 1.5 g of solids of polyurethaneurea.

A 0.8 g amount of the 1.5 g of the obtained solids was taken in an Erlenmeyer flask, 10 ml of 60% perchloric acid was added, and treatment was performed at 60° C. for 34 hours with occasional agitation.

When the treatment by the perchloric acid ended, the solution was cooled to room temperature and was flushed into a beaker by 150 ml of ion exchange water to precipitate the hard segments. The precipitate was filtered by a glass filter (3G4) and fully washed on the filter by ion exchange water. Further, it was washed by 50 ml of 1N sodium hydroxide aqueous solution and fully washed again by ion exchange water. The washed precipitate was vacuum dried at 80° C. for two hours and the hard segment portion of the polyurethaneurea polymer was obtained as a solid portion. The yield with respect to the theoretical value is 93%.

The average molecular weight of the hard segment was determined based upon the integrated intensity ratio of methylene group sandwiched by the benzene rings according to a ¹H-NMR measurement. As a result, the average molecular weight of the hard segment of the non-treated polymer was 935 and the average molecular weight of the hard segment of the treated polymer was 934.

The obtained solids were made a 0.1% solution using a DMSO-tetrahydrofuran solution which was passed through a 0.45 μm filter for use as a liquid chromatography sample. A 20 μl amount of this was injected by a microsyringe and the measurement was performed under the above-mentioned conditions.

The same measurement was performed for the polymers of Examples 6 to 9 and Comparative Examples 1 to 5 to obtain liquid chromatograms. The results of these measurements are shown in FIGS. 26 to 34. From these charts, the ratios of the hard segments with different molecular weights were found by vertical division. The results are shown in Table 12.

TABLE 12

| | | Example | | | | Comparative Example | | | |
|---|---|---|---|---|---|---|---|---|---|
| | | 6 | 7 | 8 | 9 | 1 | 2 | 3 | 4 | 5 |
| Compound (1)/EDA (mol %/mol %) | | 100/0 | 75/25 | 50/50 | 25/75 | 0/100 | | | | |
| Peak area ratio | P1 | 12% | 23 | 29 | 39 | 52 | 23 | 35 | 37 | 41 |
| | P2 | 53% | 49 | 48 | 41 | 35 | 28 | 34 | 31 | 36 |
| | P3 | 13% | 15 | 14 | 14 | 10 | 21 | 18 | 17 | 15 |
| | P4 | 22% | 13 | 9 | 6 | 3 | 28 | 12 | 14 | 8 |

From Table 12, it will be seen that along with an increase in the ratio of the compound (1) of the present invention in the chain extender when the compound (1) is used as the chain extender (an increase of the average molecular weight of the hard), the peak area ratio of P2 (corresponding to U4 hard) increases and the peak area ratio of P1 (corresponding to U2 hard) decreases. In a polymer synthesized by the corresponding EDA and MDI without the use of the compound (1), along with the increase in the average molecular weight of the hard segments, the peak area ratios P3 (corresponding to U6 hard) and P4 (corresponding to U8 hard) increase. That is, the distribution of the hard segments of the polymer using the compound (1) of the present invention is considerably sharper than the distribution of the polymer synthesized by EDA and MDI. Furthermore, the presence of the P1 and P3 in the peak area ratio of the hard segment analysis of polymer in Example 6 is considered to be due to the inclusion of a trace amount of EDA in the compound (1) added.

Figure 35:
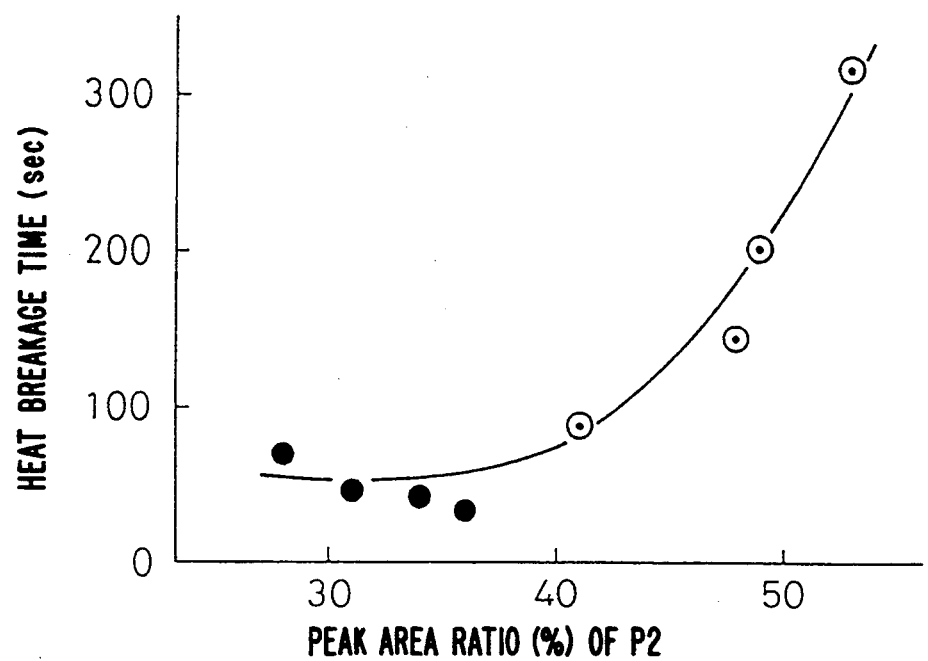
FIG. 35 is a view showing the relationship of the peak area ratio(%) of P2 and the seconds of heat breakage of film.
Figure 36:
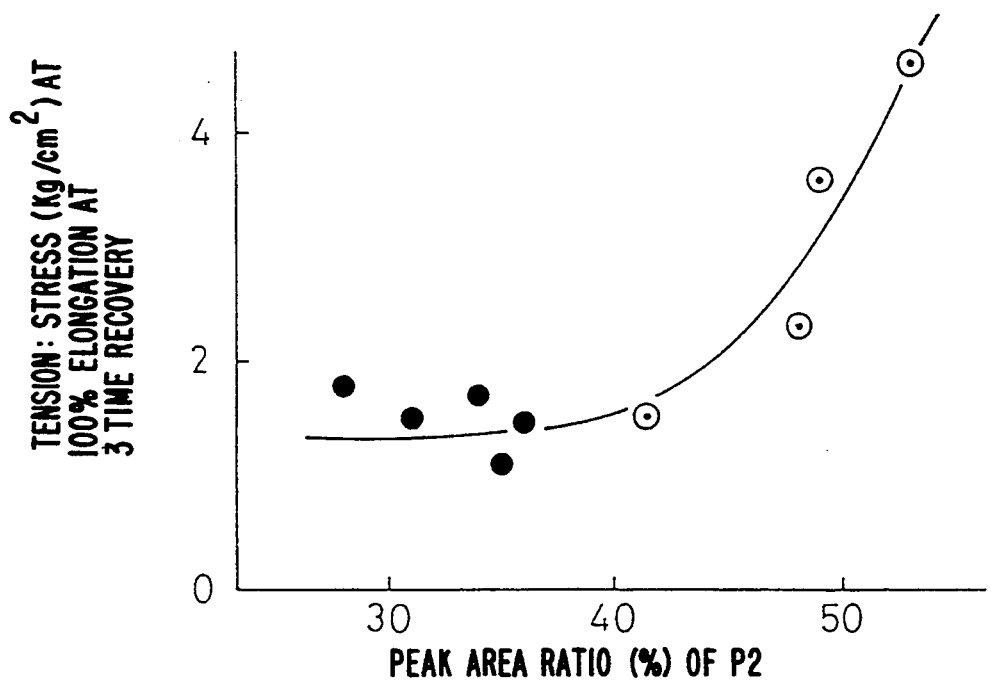
FIG. 36 is a view showing of the relationship of the peak area ratio(%) of P2 and the tension after heat treatment of the film.

Further, the physical properties corresponding to the polyurethaneurea polymers with the different area ratio of P2 of Table 12 (seconds of heat breakage and tension after heat treatment) are extracted from Table 4 and Table 5 and shown in FIGS. 35 and 36.

From these figures, it will be understood that the if the area ratio of P2 is more than 40 molar percent of the whole, superior physical properties (seconds to heat breakage and tension after heat treatment) are shown.

Example 24

The hard segment analysis data of polyurethaneurea elastic fibers now on the market are shown below.

Figure 37:
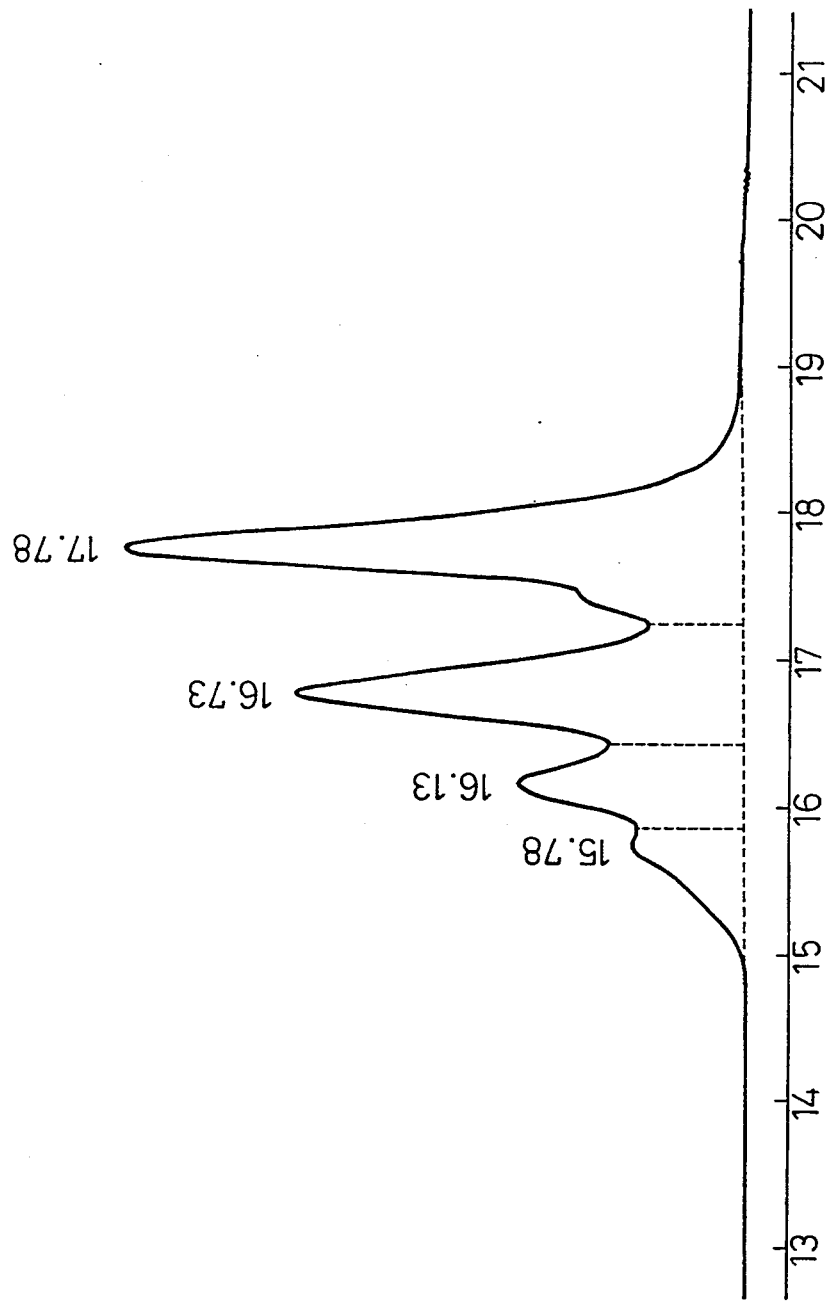
FIG. 37 is a hard segment liquid chromatogram of Lycra.
Figure 38:
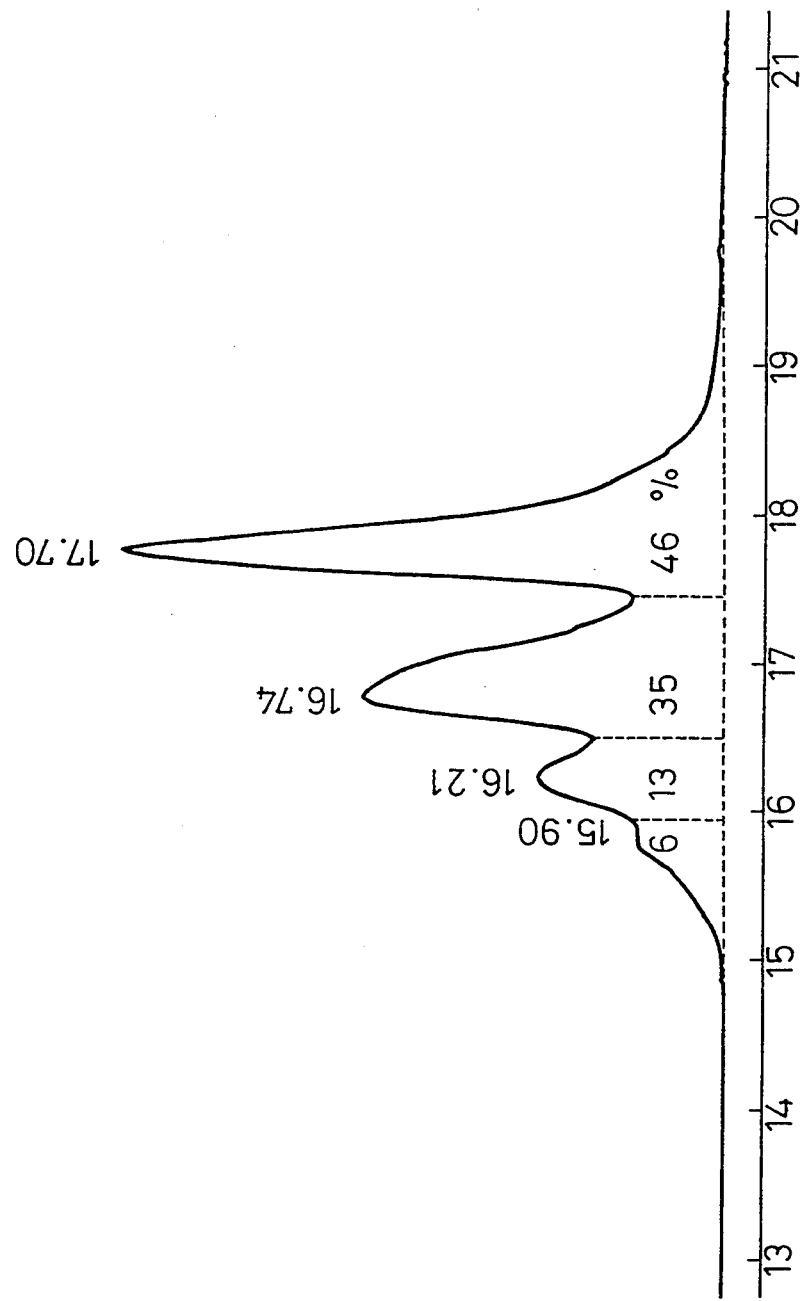
FIG. 38 is a hard segment liquid chromatogram of Opelon.
Figure 39:
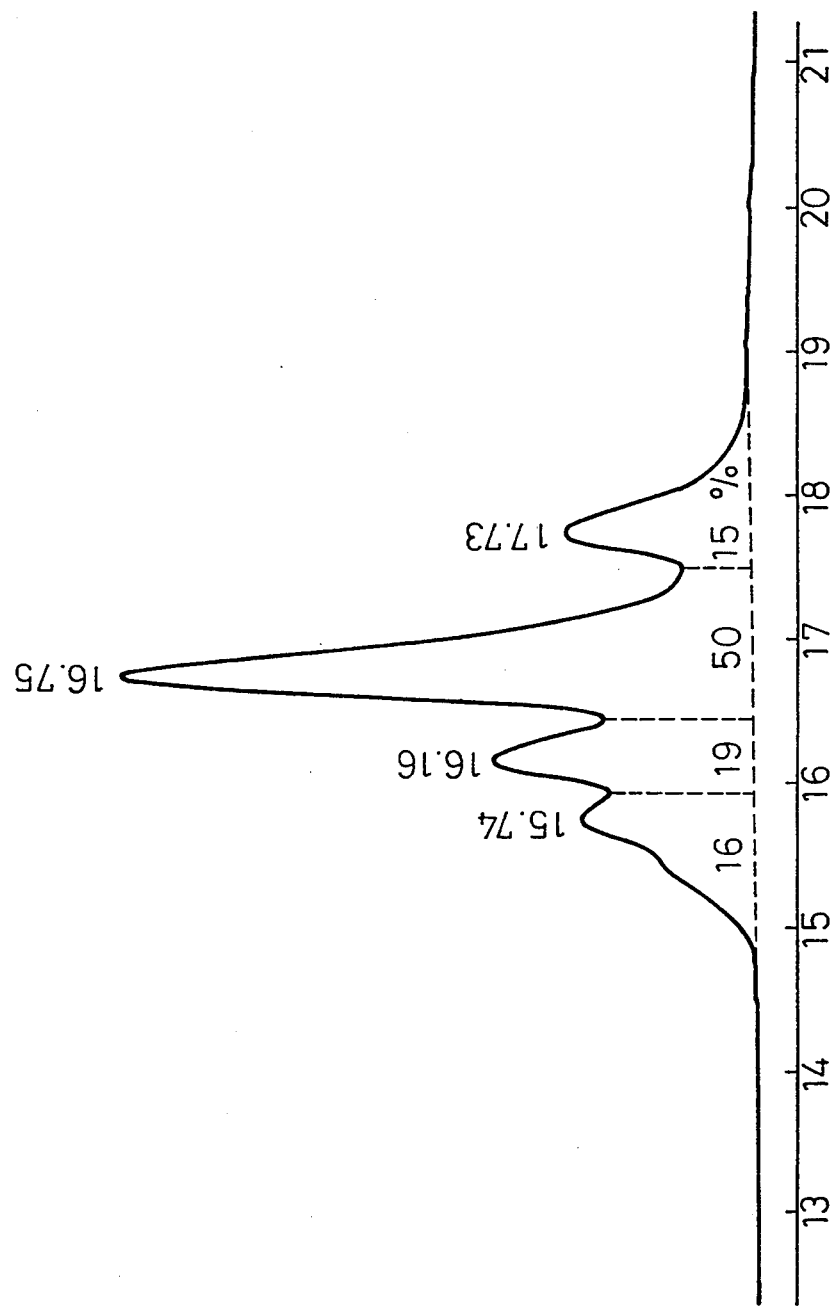
FIG. 39 is a hard segment liquid chromatogram of fiber of Example 6 according to the present invention.

The samples used are Lycra T-156C (DuPont) and Opelon T-127C (Toray.DuPont) and the samples were subjected to a pre-extract treatment with acetone and toluene in a Soxhlet extractor. Then, the treatment with the perchloric acid and the chromatography determination were carried out in the same manner as in Example 23. The results are shown in FIGS. 37 and 38. Furthermore, the determination results of the fiber obtained in the same manner as in Example 6 of the present invention are shown in FIG. 39.

As is clear from these results, the polyurethaneurea according to the present invention is definitely new type, because the P1 peak area ratio and P2 peak area ratio of conventional polyurethaneurea elastic fibers are 46–51% and 32–35%, respectively, whereas the P1 peak area ratio and P2 peak area ratio of the present invention are 15% and 50%, respectively.

Industrial Applicability

The compound of the present invention is useful as a diamine starting material for resins (polyurethaneureas, polyamides, polyimides, polyureas) and curing agents for epoxy resins. In particular, it is a novel diaminourea compound useful as a chain extender of a shaped article (for example, elastic fibers and film) of a high heat resistance polyurethaneurea resin. In accordance with the process for production of the present invention, it is possible to produce the compound at a high purity and high yield. Further, if the compound of the present invention is used as a chain extender, it is possible to control the distribution of molecular weight of the hard segments and the polyurethaneurea which is produced is vastly improved in the heat resistance. Since the polyurethaneurea elastic fiber according to the present invention has a high heat resistance, it is possible to knit with polyester fiber to be dyed under the polyester dyeing condition at 130° C.

We claim:

1. A diaminourea compound represented by the formula (I);

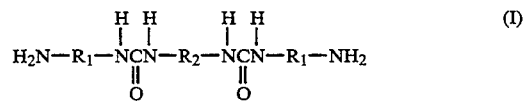

wherein $R_1$ is a straight or branched chain alkylene group having to 2 to 8 carbon atoms and $R_2$ is a methane diphenylene group.

2. A process for the production of a diaminourea compound represented by formula (I);

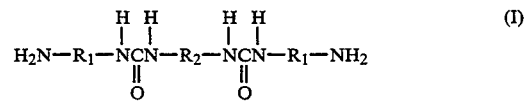

wherein $R_1$ is a straight or branched chain alkylene group having 2 to 8 carbon atoms $R_2$ is a methane diphenylene group comprising reacting a diurea compound represented by the formula (II);

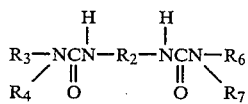 (II)
wherein $R_3$, $R_4$, $R_6$, and $R_7$ independently represent a straight or branched chain alkyl group having 1 to 4 carbon atoms;
with a diamine compound represented by formula (III);
$$H_2N-R_1-NH_2 \qquad (III)$$
wherein $R_1$, is previously defined.
* * * * *